(12) United States Patent
Cope et al.

(10) Patent No.: US 8,662,425 B2
(45) Date of Patent: Mar. 4, 2014

(54) HIGH-THROUGHPUT, SEED SAMPLING AND COLLECTION SYSTEM AND METHOD

(71) Applicant: Pioneer Hi-Bred International, Inc., Johnston, IA (US)

(72) Inventors: Jason M. Cope, Ankeny, IA (US); Gary L. Jaehnel, Des Moines, IA (US); Joshua L. Mongan, Saint Charles, IA (US)

(73) Assignee: Pioneer Hi Bred International Inc, Johnston, IA (US)

(*) Notice: Subject to any disclaimer, the term of this patent is extended or adjusted under 35 U.S.C. 154(b) by 0 days.

(21) Appl. No.: 13/652,981

(22) Filed: Oct. 16, 2012

(65) Prior Publication Data
US 2013/0037636 A1 Feb. 14, 2013

Related U.S. Application Data

(62) Division of application No. 12/726,874, filed on Mar. 18, 2010, now Pat. No. 8,313,053.

(60) Provisional application No. 61/162,039, filed on Mar. 20, 2009.

(51) Int. Cl.
*B02C 7/18* (2006.01)
(52) U.S. Cl.
USPC ............................................. 241/6; 241/270
(58) Field of Classification Search
USPC ....................................................... 241/6–13
See application file for complete search history.

(56) References Cited

U.S. PATENT DOCUMENTS

| | | | |
|---|---|---|---|
| 1,355,777 A | 10/1920 | Pinckney | |
| 3,195,485 A | 7/1965 | Reynolds | |
| 3,530,372 A | 9/1970 | Laukien | |
| 3,572,548 A | 3/1971 | Fuchs et al. | |

(Continued)

FOREIGN PATENT DOCUMENTS

| DE | 196 16 216 A1 | 10/1997 |
|---|---|---|
| DE | 10048643 | 5/2001 |

(Continued)

OTHER PUBLICATIONS

DE-STA-CO: Material Handling Clamps; retrieved on Dec. 19, 2012 from <http://www.destaco.com/clamps.html>.

(Continued)

*Primary Examiner* — Faye Francis
(74) *Attorney, Agent, or Firm* — Pioneer Hi-Bred Int'l, Inc.

(57) ABSTRACT

A system and method for preparing a sample of seeds or representative seed portions are provided. In various embodiments, the system and method include a force applying member and a seed container that includes at least one compartment containing a seed. The force applying member is configured to apply a force to the seed so as to break the seed into two or more seed particles, which in some embodiments may be collected in a seed particle collector. The present invention improves on the prior art by greatly reducing (and in some embodiments eliminating) the manual processes typically involved in generating tissue samples from seeds and preparing the tissue for genetic analysis. Additionally, the present invention is scaleable, and can be configured to generate samples from many seeds in a short period of time. The present invention also minimizes the risk of contamination and cross-contamination of the seed particles.

16 Claims, 41 Drawing Sheets

(56) References Cited

U.S. PATENT DOCUMENTS

| | | | |
|---|---|---|---|
| 4,230,983 A | 10/1980 | Steere et al. | |
| 4,466,554 A | 8/1984 | Hanacek et al. | |
| 4,602,716 A | 7/1986 | Barla-Szabo et al. | |
| 4,694,996 A | 9/1987 | Siegel | |
| 5,677,474 A | 10/1997 | Rogers | |
| 5,934,188 A | 8/1999 | Johnson et al. | |
| 6,307,123 B1 | 10/2001 | Kriz et al. | |
| 6,537,826 B1 | 3/2003 | Horigane | |
| 6,616,075 B1* | 9/2003 | Millerd | 241/168 |
| 6,706,989 B2 | 3/2004 | Hunter et al. | |
| 6,809,819 B1 | 10/2004 | Vinjamoori et al. | |
| 6,865,556 B2 | 3/2005 | Penner et al. | |
| 6,959,617 B2 | 11/2005 | Deppermann | |
| 7,044,306 B2 | 5/2006 | Deppermann et al. | |
| 7,048,216 B2* | 5/2006 | Ng | 241/169.1 |
| 7,067,834 B2 | 6/2006 | Horigane et al. | |
| 7,134,351 B2 | 11/2006 | Deppermann | |
| 7,229,034 B2 | 6/2007 | Feazel et al. | |
| 7,290,665 B2 | 11/2007 | Hunter et al. | |
| 7,367,155 B2 | 5/2008 | Kotyk et al. | |
| 7,454,989 B2 | 11/2008 | Deppermann | |
| 7,502,113 B2 | 3/2009 | Deppermann et al. | |
| 7,588,151 B2 | 9/2009 | Hunter et al. | |
| 7,591,101 B2 | 9/2009 | Deppermann et al. | |
| 7,591,374 B2 | 9/2009 | Hunter et al. | |
| 7,600,642 B2 | 10/2009 | Deppermann et al. | |
| 7,611,842 B2 | 11/2009 | Deppermann et al. | |
| 7,685,768 B2 | 3/2010 | Deppermann et al. | |
| 7,703,238 B2 | 4/2010 | Deppermann et al. | |
| 7,707,883 B2 | 5/2010 | DiFoggio | |
| 7,767,883 B2 | 8/2010 | Deppermann et al. | |
| 7,830,516 B2 | 11/2010 | Deppermann et al. | |
| 7,832,143 B2 | 11/2010 | Deppermann et al. | |
| 7,849,632 B2 | 12/2010 | Deppermann et al. | |
| 7,877,926 B2 | 2/2011 | Deppermann et al. | |
| 7,905,050 B2 | 3/2011 | Hunter et al. | |
| 7,934,600 B2 | 5/2011 | Deppermann et al. | |
| 7,941,969 B2 | 5/2011 | Deppermann et al. | |
| 7,998,669 B2 | 8/2011 | Deppermann et al. | |
| 8,028,469 B2 | 10/2011 | Deppermann et al. | |
| 8,071,845 B2 | 12/2011 | Deppermann et al. | |
| 8,076,076 B2 | 12/2011 | Osborn et al. | |
| 8,221,968 B2 | 7/2012 | Becker et al. | |
| 8,245,439 B2 | 8/2012 | Deppermann et al. | |
| 8,281,935 B2 | 10/2012 | Deppermann et al. | |
| 8,313,053 B2 | 11/2012 | Cope et al. | |
| 2004/0267457 A1 | 12/2004 | Timmis et al. | |
| 2006/0046244 A1 | 3/2006 | Deppermann et al. | |
| 2007/0048872 A1 | 3/2007 | Deppermann et al. | |
| 2008/0113367 A1 | 5/2008 | Becker et al. | |
| 2011/0081716 A1 | 4/2011 | Deppermann et al. | |
| 2011/0088570 A1* | 4/2011 | Johnson et al. | 99/549 |
| 2011/0129836 A1 | 6/2011 | Deppermann et al. | |
| 2011/0217700 A1 | 9/2011 | Deppermann et al. | |
| 2011/0296930 A1 | 12/2011 | Deppermann et al. | |
| 2012/0079629 A1 | 3/2012 | Deppermann et al. | |
| 2012/0180386 A1 | 7/2012 | Deppermann et al. | |

FOREIGN PATENT DOCUMENTS

| | | |
|---|---|---|
| EP | 1 346 206 B1 | 9/2003 |
| EP | 1 391 713 A2 | 2/2004 |
| GB | 2 293 744 A | 4/1996 |
| KR | 10-2000-0022775 | 11/2001 |
| KR | 339689 B | 6/2002 |
| RU | 1805835 A3 | 3/1993 |
| RU | 2187919 C2 | 8/2002 |
| WO | WO 03/084847 A2 | 10/2003 |
| WO | WO 2006/026466 A2 | 3/2006 |
| WO | WO 2006/026467 A2 | 3/2006 |
| WO | WO 2007/025250 A2 | 3/2007 |
| WO | WO 2007/103769 A2 | 9/2007 |
| WO | WO 2007/103786 A2 | 9/2007 |
| WO | WO 2008/150798 A1 | 12/2008 |
| WO | WO 2009/032741 A2 | 3/2009 |

OTHER PUBLICATIONS

Professional Plastics: The Global Leader in High Performance Plastics; Plastic Sheets; retrieved on Dec. 19, 2012 from <http://www.professionalplastics.com/PLASTIC-SHEETS>, <http://www.professionalplastics.com/cgi-bin/main/co_disp/displcurpage/16/carfnbr/118>, and <http://www.professionalplastics.com/cgi-bin/main/co_disp/displ/curpage/17/carfnbr/118>.

Sangtong, V., et al.; "Serial Extraction of Endosperm Drillings (SEED)—A Method for Detecting Transgenes and Proteins in Single Viable Maize Kernels;" Plant Molecular Biology Reporter; vol. 19; pp. 151-158; dated Jun. 2001; retrieved on Dec. 19, 2012 from <http://www.google.com/url?sa=t&rct=j&q=&esrc=s&frm=1&source=web&cd=1&cad=rja&ved=0CDsQFjAA&url=http%3A%2F%2Fagron.iastate.edu%2Fscottlab%2Fwebpages%2FPublications%2520and%2520Presentations%2FSEED.pdf&ei=AgbSUMi8MMnL0AG2_oDgBg&usg=AFQjCNHa-U2wlj50WP1bhLlhaquwubbV5g&sig2=8xfpCZ7rurLKB7zEH0d9Jw&bvm=bv.1355534169,d.dmQ>.

Aitken-Christie, J. et al., *Automation in Plant Tissue Culture*, Automation and Environmental Control in Plant tissue Culture (1995) 1-18.

Casady, W. W. et al., *An Automated Kernel Positioning Device for Computer Vision Analysis of Grain*, American Society of Agricultural Engineers, vol. 32(5) (1989) 1821-1826.

Chunwongse, J. et al., *Pre-Germation Genotypic Screening Using PCR Amplification of Half-Seeds*, Theor Appl Genet, 86 (1993) 694-698.

Churchill, D. B. et al., *Rotating Table for Measuring Seed Physical Properties*, Transactions of the ASAE, vol. 34(4) (1991) 1842-1845.

Dekkers, J. C. M. et al., *The Use of Molecular Genetics in the Improvement of Agricultural Populations*, Nature Reviews | Genetics, vol. 3, (2002) 22-32.

Gasvoda, D. et al., *Whiteback Pine Seed Scarifier*, United States Department of Agriculture Food Service, Technology & Development Program, Timber Tech Tips, 0224-2332-MTDC (2002) pp. 1-6.

Hahnen, S. et al., *Automated DNA Preparation from Maize Tissues and Food Samples Suitable for Real-time PCR Dectection of Native Genes*, European Food Research Technology, vol. 215 (2002) 443-446.

Higley, P.M., et al., *Effects of Non-Destructive Tissue Extraction on the Viability of Corn, Soybean and Bean Seeds*, Seed Sci. & Technol., 22 (1994) 245-252.

Horigane, A. et al., *Evaluation of Color Characteristics of Cross-Sectioned Wheat Kernels*, Food Sci. Technol. Res., 9:4 (2003), 327-331.

Horigane, A. et al., *Measurement of Brightness of Cross-Sectioned Wheat Kernels*, Japanese Journal of Crop Science, vol. 72, (attachment No. 1) (2003) 176-177.

Horigane, A. et al., *Two-Dimensional Analysis of Kernels Using a New Sample Preparation Method*, Chemistry and Biology, vol. 41, No. 6 (2003) 398-402.

Kamiya, M. et al., *Rapid DNA Extraction Method from Soybean Seeds*, Breeding Science 53 (2003) 277-279.

Kang, H.W. et al., *A Rapid DNA Extraction Method for RFLP and PCR Analysis from a Single Dry Seed*, Plant Molecular Biology Reporter, 16:90 (1998) 1pg.

Kerk, N.M. et al., *Laser Capture Microdissection of Cells from Plant Tissues*, Plant Physiology, vol. 132 (2003) 27-35.

Krysan, P., *Ice-Cap. A High-Throughput Method for Capturing Plant Tissue Samples for Genotype Analysis*, Plant Physiology, vol. 135 (2004) 1162-1169.

Liu, W. et al., *Highly Efficient Doubled-Haploid Production in Wheat via Induced Microsphere Embryogenesis*, Crop Science, vol. 42 (2002) 686-692.

McCarthy, P. L. et al., *Rapid Identification of Transformed Wheat Using a Half-Seed PCR Assay*, BioTechniques 32 (2002) 560-564.

(56) References Cited

OTHER PUBLICATIONS

Pearson, T.C. et al., *Reduction of Aflatoxin and Fumonisin Contamination in Yellow Corn by High-Speed Dual-Wavelength Sorting*, Cereal Chem. 81 (4), (2004) 490-498.

Peterhansel, C. et al., *Quantitative Detection of Transgenic and Endogenous DNA Sequences in Seeds After Automated DNA Preparation*, Biomed. Eng. Appl. Basis Commun. 16 (2004) 1-6.

Rafalkski, J. A., *Genetic Diagnostics in Plant Breading: RAPDs Microsatellites & Machines*, TIG, vol. 9, No. 8 (Aug. 1993) 275-280.

Sangtong, V. et al., *Serial Extraction of Endosperm Drillings (SEED)—A Method for Detecting Transgenes and Proteins in Single Viable Maize Kernels*, Plant Molecular Biology Reporter 19 (2001) 151-158.

Skinner, D. Z. et al., *Segregation and Conditioning Probability Association of Molecular Markers With Traits in Autotetraploid Alfalfa*, Molecular Breading, vol. 5 (2000) 295-306.

Smith, J. S. C. et al., *Genetic Purity and Testing Technologies for Seed Quality: A Company Perspective*, Seed Science Research 8 (1998) 285-293.

Sweeney, P. et al., *Random Amplified Polymorphic DNA Analysis of Dry Turfgrass Seed*, HortScience 31(3), (1996) 400-401.

Turner, N.A., et al., *Sampling and Analysis for Determining Relationship of Calcium Concentration to Bitter Pit in Apple Fruit*, New Zealand Journal of Agricultural Research 20:4 (1977) 525-532.

Von Post, R. et al., *A High-throughput DNA Extraction Method for Barley Seed*, Euphytica, 130 (2003) 255-260.

Wang, G.L., et al., *PCR Amplification from Single Seeds, Facilitating DNA Marker-Assisted Breeding*, Nucleic Acids Research 21(10), (1993) 2527.

Wenxue, Z., et al., *PCR Analysis of Half-Seeds of Cereal Crops and Its Application in Marker-assisted Selection and Breeding*, Chinese Journal of Biotechnology, 12:4 (1997) 249-255.

Xu, Y., *Developing Marker-Assisted Selection Strategies for Breeding Hybrid Rice*, Plant Breeding Review, 23 (2003) 73-174.

Yang, W, et al., *A Preliminary Study of Non-Lethal Specific Sampling of Corn Embryo and Endosperm and Feasibility of Automating the Seed Selection Process Utilizing the Specific Sampling Technique*, Pioneer Hi-Bred (2002) 1-41.

Wang, J. et al., *Identification of Parents of F1 Hybrids Through SSR Profiling of Material and Hybrid Tissue*, Euphytica, vol. 124 (2002) 29-34.

Yao, Y. et al., *Single Kernel Sampling Method for Maize Starch Analysis While Maintaining Kernel Vitality*, Cereal Chem. 79:6 (2002) 757-762.

DuPont CoatingSolutions [online] [retrieved Apr. 4, 2013]. Retrieved from the Internet: <URL: www.ccaiweb.com/PDF/MembersOnly/annualpres08/DuPontCoatingSolutions—Corporate Member Presentation.pdf>. (undated) 12 pages.

200 watt CO2 laser from Synrad provides the best cost per delivered watt available in today . . . [online] [retrieved Dec. 18, 2012]. Retrieved from the Internet: <URL: http://www.synrad.com/fseries/f201.htm>. (2011) 2 pages.

Skinner, D. Z. et al., *Segregation and Conditioning Probability Association of Molecular Markers With Traits in Autotetraploid Alfalfa*, Molecular Breading, vol. 6 (2000) 295-306.

\* cited by examiner

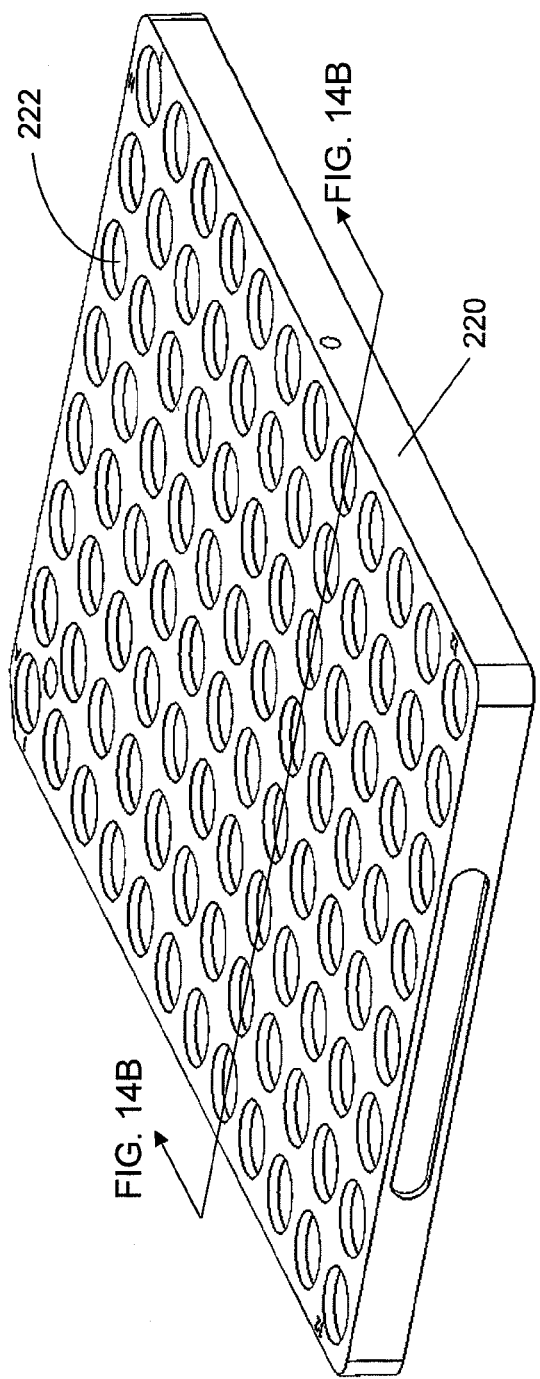
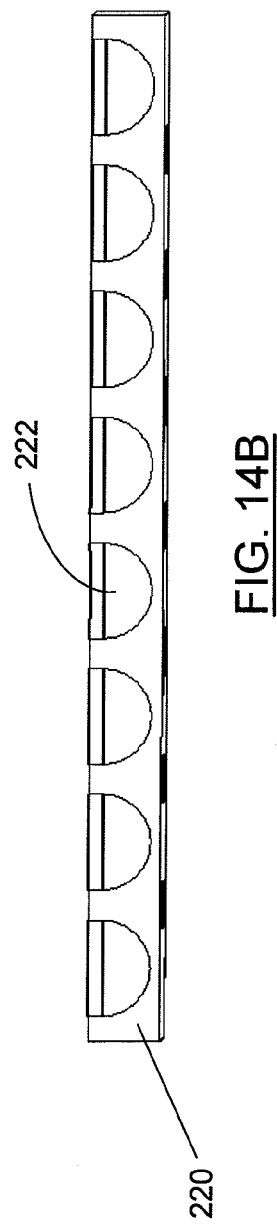
FIG. 14A
FIG. 14B

HIGH-THROUGHPUT, SEED SAMPLING AND COLLECTION SYSTEM AND METHOD

CROSS-REFERENCE TO RELATED APPLICATIONS

This application is a divisional application of U.S. patent application Ser. No. 12/726,874, filed on Mar. 18, 2010, patented as U.S. Pat. No. 8,313,053, which claims priority to U.S. Provisional Application No. 61/162,039, filed Mar. 20, 2009, each of which is hereby incorporated herein in its entirety by reference.

FIELD OF THE INVENTION

The present invention relates generally to systems and methods for obtaining and preparing seeds and samples of seeds for analysis, such as genetic analysis. More specifically, the present invention provides a system and method for obtaining tissue samples from one or more individual seeds.

BACKGROUND OF THE INVENTION

It is conventional practice in plant breeding or plant advancement experiments to grow plants from seeds of known parentage. The seeds are planted in experimental plots, growth chambers, greenhouses, or other growing environments in which they are either cross-pollinated with other plants of known parentage or self-pollinated. The resulting seeds are the offspring of the two parent plants or the self-pollinated plant and are harvested, processed, and planted to continue the plant breeding cycle. Specific laboratory or field-based tests may be performed on the plants, plant tissues, seeds or seed tissues in order to aid in the breeding or advancement selection process.

Generations of plants based on known crosses or self-pollinations are planted and then tested, such as through trait purity tests, to see if these lines or varieties are moving toward characteristics that are desirable in the marketplace. Examples of desirable traits include, but are not limited to, increased yield, increased homozygosity, improved or newly conferred resistance and/or tolerance to specific herbicides and/or pests and pathogens, increased oil content, altered starch content, nutraceutical composition, drought tolerance, and specific morphological based trait enhancements.

Often, seeds having desirable characteristics are produced commercially for sale in the marketplace. In such instances, quality control tests, such as genetic and trait purity tests, may be conducted to determine that the seeds indeed comprise the advertised genetic composition. In many instances, a certain number of seeds may be sampled from each bag of seeds produced. For example, it is not uncommon to test approximately one hundred seeds from each production bag in order to verify the genetic composition of the seeds from the bag. For some seed types, such as those in large production, this can translate to over one million individual seeds to be sampled, prepared, and genetically tested.

In order to test the genetic composition of the seeds, the whole seed, representative samples of the individual seeds themselves, or representative samples of the plants that develop from the seeds are gathered. For example, according to one method for acquiring a prepared representative sample, a hole is drilled in a small location on the seed and the debris from the seed is removed. The debris is then transferred to a test tube or other container and analyzed. Another method is described in V. Sangtong, E. C. Mottel, M. J. Long, M. Lee, and M. P. Scott, *Serial Extraction of Endosperm Drillings (SEED)—A Method for Detecting Transgenes and Proteins in Single Viable Maize Kernels*, Plant Molecular Biology Reporter 19: 151-158, June 2001, in which a hand-held rotary grinder is used to grind off so-called "drillings" from each kernel so that the drillings may be analyzed.

In another method of obtaining a representative seed sample, the seeds to be sampled may be grown out, such as by placing a number of individual seeds on a paper towel that is then rolled up and placed in a growth chamber for a certain period of time. Once the immature plants have emerged, samples of the coleoptiles are taken. Another method involves obtaining an unprepared sample, such as a leaf tissue sample, a portion of grown out coleoptiles, a laser cut sample, or a sample cut by clippers, and placing the unprepared sample in corresponding vials that are placed in a laboratory grinder, such as the Geno/Grinder 2000 available from SPEX Certiprep of Methuchen, N.J. Ball bearings are used crush up the seeds into a powder which can then be tested. U.S. Patent Publication No. 2008/0113367, which is assigned to the assignee of the present application, and which is incorporated herein by reference in its entirety, describes yet another method of obtaining a representative sample of seeds through removal and collection of tissue using a hand-held and manually-operated tool having one or more cutting edges.

The above methods of obtaining seeds samples and processing them for genetic analysis are extremely time consuming, expensive, and involve numerous manual processes. In addition, extreme care and diligence must be employed in order to avoid contamination and cross-contamination of the samples. Also, in many instances the success and effectiveness of these methods depend heavily on the attention and accuracy of the technician. Furthermore, the above methods are not economically practicable for those situations related to the production of commercial seeds.

As a result, there is a need for a system and method for preparing a sample of individual seeds for use in genetic and trait purity testing and the like. In various embodiments, the system and method should allow a large number of seeds to be sampled in a relatively small amount of time and should maintain a particular throughput level for efficiency purposes. It should reduce or virtually eliminate contamination and cross-contamination between samples and should be flexible so as to accommodate the need to sample large numbers of seeds.

BRIEF SUMMARY OF VARIOUS EMBODIMENTS

The present invention addresses the above needs and achieves other advantages by providing a system and method for sampling a seed. In general, the method includes receiving a seed container having a seed located inside an isolated compartment of the seed container, and applying a force to the seed with a force applying member to break the seed into two or more seed particles. In some embodiments, the force applying member may include a protrusion, and applying a force to the seed may comprise pressing the protrusion into contact with the compartment of the container to break the seed into the seed particles. In some embodiments, applying force to the seed may comprise pressing the protrusion into direct contact with the seed to break the seed into the seed particles. Some embodiments may further comprise pressing the seed particles out of the compartment of the seed container.

In some embodiments the method may further comprise directing the seed particles into a collection cavity of a seed particle collector. In some embodiments, the seed particles may be directed into the collection cavity of the seed particle collector using a seed particle directing member that includes a channel configured to provide an isolated passageway between the compartment of the seed container and the collection cavity of the seed particle collector. Some embodiments may further comprise applying a vibratory action to at least one of the seed particle directing member and the seed particle collector to influence transfer of seed particles from the seed container through the seed particle directing member and into the seed particle collector. In some embodiments, receiving the seed container may comprise receiving a seed container that includes a first layer that defines a cavity having an open end, and a backing portion configured to be affixed to the first layer, wherein the backing portion covers the open end of the cavity to create the isolated compartment. In some embodiments, the force may be applied using a mechanically driven force applying member.

Another embodiment of the present invention provides a method of sampling a plurality of seeds. In general the method includes receiving a seed container having a plurality of seeds, each located inside a respective isolated compartment of a plurality of isolated compartments of the seed container, and applying a force to the seeds with a force applying member to break each seed into a respective group of two or more seed particles. In some embodiments, the force applying member may include a plurality of protrusions, and applying a force to the seeds may comprise pressing each of the protrusions into contact with a respective compartment of the container to break each seed into the respective group of seed particles. In some embodiments, the force applying member may include a plurality of protrusions, and applying a force to the seeds may comprise pressing each protrusion into direct contact with a respective seed to break each seed into a respective group of two or more seed particles. Some embodiments may further comprise pressing each respective group of seed particles out of each respective compartment of the seed container.

In some embodiments the method may further comprise directing each respective group of seed particles into a corresponding collection cavity of a plurality of collection cavities of a seed particle collector. In some embodiments, each respective group of seed particles may be directed into the corresponding collection cavity of the seed particle collector using a seed particle directing member that includes a plurality of channels configured to provide a plurality of isolated passageways between the plurality of compartments and the corresponding plurality of collection cavities.

Some embodiments may further comprise applying a vibratory action to at least one of the seed particle directing member and the seed particle collector to influence transfer of seed particles from the seed container through the seed particle directing member and into the seed particle collector. In some embodiments, receiving the seed container may comprise receiving a seed container that includes a first layer that defines a plurality of cavities each having an open end, and a backing portion configured to be affixed to the first layer, wherein the backing portion covers the open ends of the plurality of cavities to create the plurality of isolated compartments. In some embodiments, receiving a seed container may comprise receiving a seed container wherein the plurality of seed compartments are configured in an array. In some embodiments, receiving a seed container may comprise receiving a seed container wherein the seed container further includes a positionally-addressable ordered array of indicia associated with the array of seed compartments to identify each specific compartment. In some embodiments, directing each respective group of seed particles may comprise directing the seed particles into a plurality of collection cavities that are configured in an array. In some embodiments, the seed particle collector may further include a positionally-addressable ordered array of indicia associated with the array of collection cavities to identify each collection cavity.

Another embodiment of the present invention provides a system for sampling a seed. In general, the system includes a seed container comprising a seed located inside an isolated compartment of the seed container, and a force applying member, wherein the force applying member is configured to break the seed into two or more seed particles. In some embodiments, the force applying member may include a protrusion and may be configured to press the protrusion into contact with the compartment of the container to break the seed into two or more seed particles. In some embodiments, the force applying member may include a protrusion and may be configured to press the protrusion into direct contact with the seed to break the seed into two or more seed particles. In some embodiments, the force applying member may be further configured to press the seed particles out of the compartment of the seed container. Some embodiments may further comprise a seed particle collector having a collection cavity that is configured to collect the seed particles.

In some embodiments the system may further comprise a seed particle directing member configured to direct the plurality of seed particles and wherein the seed particle directing member includes a channel configured to provide an isolated passageway between the compartment of the seed container and the collection cavity of the seed particle collector. Some embodiments may further comprise a vibration generating apparatus configured to apply a vibration to at least one of the seed particle directing member or the seed particle collector to influence transfer of seed particles from the seed container through the seed particle directing member and into the seed particle collector. In some embodiments, the seed container may include a first layer that defines a cavity having an open end, and wherein the open ended cavity defines the isolated compartment. In some embodiments, the seed container may further include a backing portion configured to be affixed to the first layer, wherein the backing portion covers the open end of the cavity, and wherein the covered cavity defines the isolated compartment. In some embodiments, the force applying member is configured to be mechanically driven.

Another embodiment of the present invention provides a system for sampling a plurality of seeds. In general the system includes a seed container having a plurality of seeds, each located inside a respective isolated compartment of a plurality of isolated compartments, and a force applying member, wherein the force applying member is configured to break each seed into a respective group of two or more seed particles. In some embodiments, the force applying member may include a plurality of protrusions and may be configured to press each of the protrusions into contact with a respective compartment of the seed container to break each seed into the respective group of seed particles. In some embodiments, the force applying member may include a plurality of protrusions and may be configured to press each of the protrusions into direct contact with a respective seed of the plurality of seeds to break each seed into the respective group of seed particles. In some embodiments, the force applying member may be further configured to press each respective group of seed particles out of each respective compartment of the seed container. Some embodiments may further comprise a seed particle collector having a plurality of collection cavities, and wherein each respective group of seed particles is collected in a corresponding collection cavity of the plurality of collection cavities.

In some embodiments the system may further comprise a seed particle directing member configured to direct the respective groups of seed particles and wherein the seed particle directing member includes a plurality of channels configured to provide a plurality of isolated passageways between the plurality of compartments and the corresponding plurality of collection cavities. Some embodiments may further comprise a vibration generating apparatus configured to apply a vibration to at least one of the seed particle directing member or the seed particle collector to influence transfer of seed particles from the seed container through the seed particle directing member and into the seed particle collector.

In some embodiments, the seed container may include a first layer that defines a plurality of cavities each having an open end, and wherein the open-ended cavities define the plurality of isolated compartments. In some embodiments, the seed container may further include a backing portion configured to be affixed to the first layer, wherein the backing portion covers the open ends of the plurality of cavities, and wherein the covered cavities define the plurality of isolated compartments. In some embodiments, the plurality of seed compartments may be configured in an array. In some embodiments, the seed container may further include a positionally-addressable ordered array of indicia associated with the array of seed compartments to identify each specific compartment. In some embodiments, the plurality of collection cavities of the seed particle collector may be configured in an array. In some embodiments, the seed particle collector may further include a positionally-addressable ordered array of indicia associated with the array of collection cavities to identify and catalogue each collection cavity.

In other embodiments, a system is provided for preparing a representative seed sample for analysis. The system includes a receiving station configured to receive a seed container having at least one isolated compartment, each isolated compartment containing a seed, a seed breaking station comprising a force applying mechanism that is configured to move a force applying member into contact with the seed in the isolated compartment such that the force applying member applies a force to the seed in the isolated compartment to break the seed into two or more seed particles, and a seed collecting station comprising a seed particle directing member configured to provide an isolated passageway between the isolated compartment of the seed container and a corresponding collection cavity of a seed particle collector. In some cases, the system is configured to automatically move the seed container between stations.

The force applying mechanism of the seed breaking station may be configured to move the force applying member such that the force applying member applies a force to the seed in the isolated compartment and then intermittently applies force to the resulting seed particles to encourage further breakage of the seed. The seed breaking station may further comprise a vibratory mechanism configured to intermittently apply a vibratory action to the seed container to encourage further breakage of the seed into the seed particles.

At the seed collecting station, a first end of the seed particle directing member may be configured to secure to the seed container and a second end of the seed particle directing member may be configured to secure to the seed particle collector. The seed particle directing member may be configured to rotate with the secured seed container and the seed particle collector to encourage transfer of the seed particles from the seed container through the seed particle directing member and into the seed particle collector. The seed collecting station may further comprise a vibratory mechanism configured to apply a vibratory action to the seed particle directing member to influence transfer of the seed particles from the seed container through the seed particle directing member and into the seed particle collector.

In some cases, the seed particle directing member may comprise a first directing member and a second directing member. A first end of the first directing member may be configured to secure to the seed container, a second end of the first directing member may be configured to secure to a first end of the second directing member, and a second end of the second directing member may be configured to secure to the seed particle collector. The first and second directing members may be configured to be detached from each other such that the second directing member and the seed particle collector are removable from the seed collecting station. Furthermore, the system may include a seed particle collector removal station configured to receive the second directing member and the seed particle collector to facilitate detachment of the seed particle collector from the second directing member.

In still other embodiments, a system is provided for preparing a representative seed sample for analysis including a receiving station, a seed breaking station, a seed collecting station, and a seed container transport mechanism. The receiving station may be configured to receive a seed container having a plurality of isolated compartments, each isolated compartment containing a seed. The seed breaking station may comprise a force applying member that includes a plurality of protrusions configured to directly contact the seed in each corresponding isolated compartment to break the seed into two or more seed particles. The seed collecting station may comprise a seed particle directing member configured to provide an isolated passageway between each isolated compartment of the seed container and a corresponding collection cavity of a seed particle collector. The seed container transport mechanism may be configured to automatically move the seed container from the receiving station to the seed breaking station and from the seed breaking station to the seed collection station upon completion of a respective operation of the receiving station, seed breaking station, and seed collection station.

The system may further include a protrusion cleaning station comprising at least one cleaning member, and the protrusion cleaning station may be configured to move into alignment with the protrusions of the force applying member to remove seed particles from the protrusions following contact between the protrusions and the seeds or seed particles. In some cases, the seed collecting station may comprise a directing member cleaning mechanism configured to substantially clear each isolated passageway of seed particle debris.

In still other embodiments, a method of preparing a representative seed sample for analysis is provided. The method includes receiving a seed container having at least one isolated compartment, each isolated compartment having a seed therein and applying a force to the seed in each isolated compartment with a force applying member to break the seed into two or more seed particles. In some cases, the force applying member includes at least one protrusion, and applying a force to the seed comprises pressing each protrusion into direct contact with the seed in each isolated compartment to break the seed into the seed particles. Applying a force to the seed may comprise applying force to the seed and then intermittently applying force to the resulting seed particles to encourage further breakage of the seed. The method may further include intermittently applying a vibratory action to the seed container to encourage breakage of the seed into the seed particles.

In some embodiments, the method may also include directing the seed particles of each isolated compartment into a corresponding collection cavity of a seed particle collector. The seed particles may be directed into the corresponding collection cavity of the seed particle collector using a seed particle directing member that includes at least one channel configured to provide an isolated passageway between each isolated compartment of the seed container and the corresponding collection cavity of the seed particle collector. The method may further include rotating the seed particle directing member together with the seed container and the seed particle collector to encourage transfer of the seed particles from the seed container through the seed particle directing member and into the seed particle collector. A vibratory action may be applied to the seed particle directing member to influence transfer of the seed particles from the seed container through the seed particle directing member and into the seed particle collector.

Furthermore, the seed particle directing member may be rotated together with the seed container and the seed particle collector to encourage transfer of the seed particles from the seed container through the seed particle directing member and into the seed particle collector. A vibratory action may be applied to the seed particle directing member to influence transfer of the seed particles from the seed container through the seed particle directing member and into the seed particle collector. In addition, the method may include removing the seed particle collector from the seed particle directing member and substantially clearing each isolated passageway of seed particle debris.

BRIEF DESCRIPTION OF THE DRAWINGS

Figure 1:
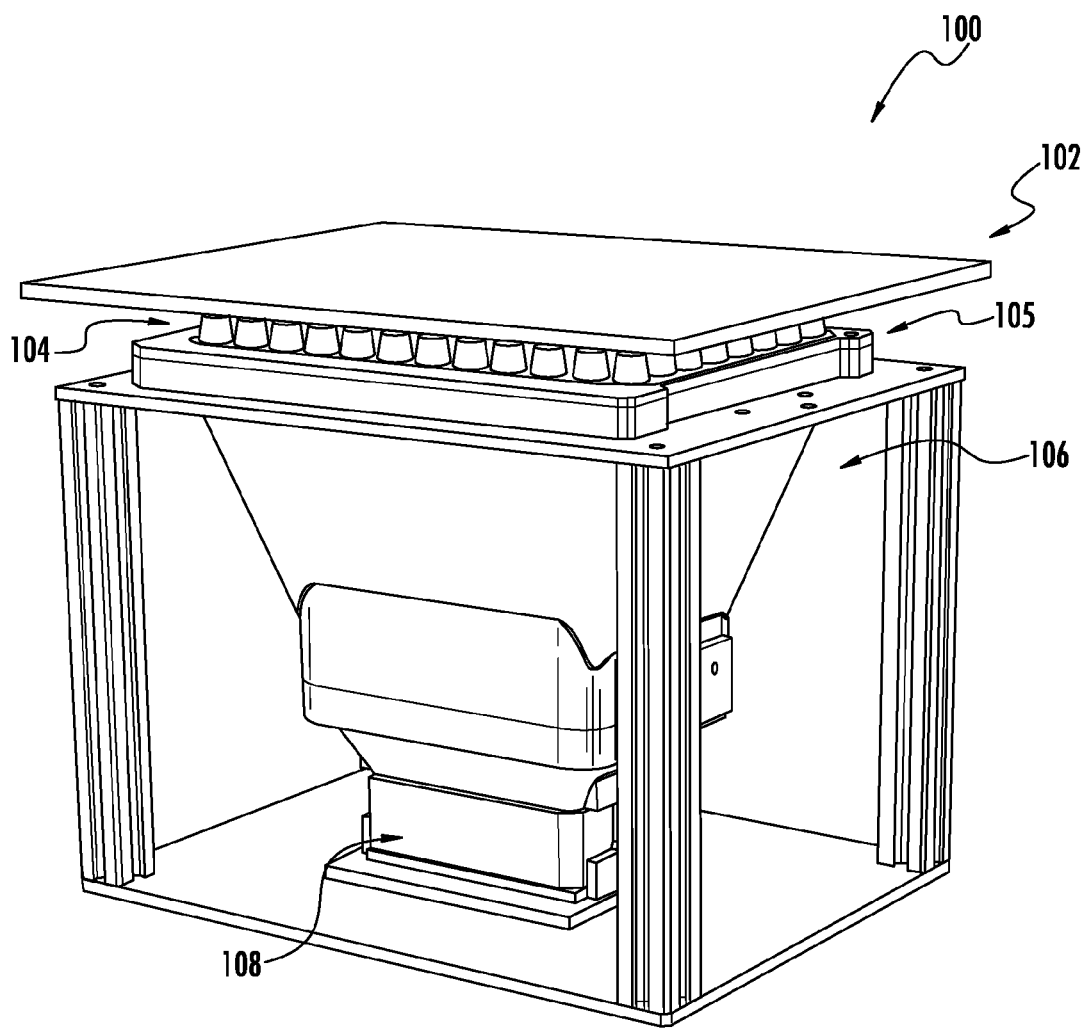
Figure 2:
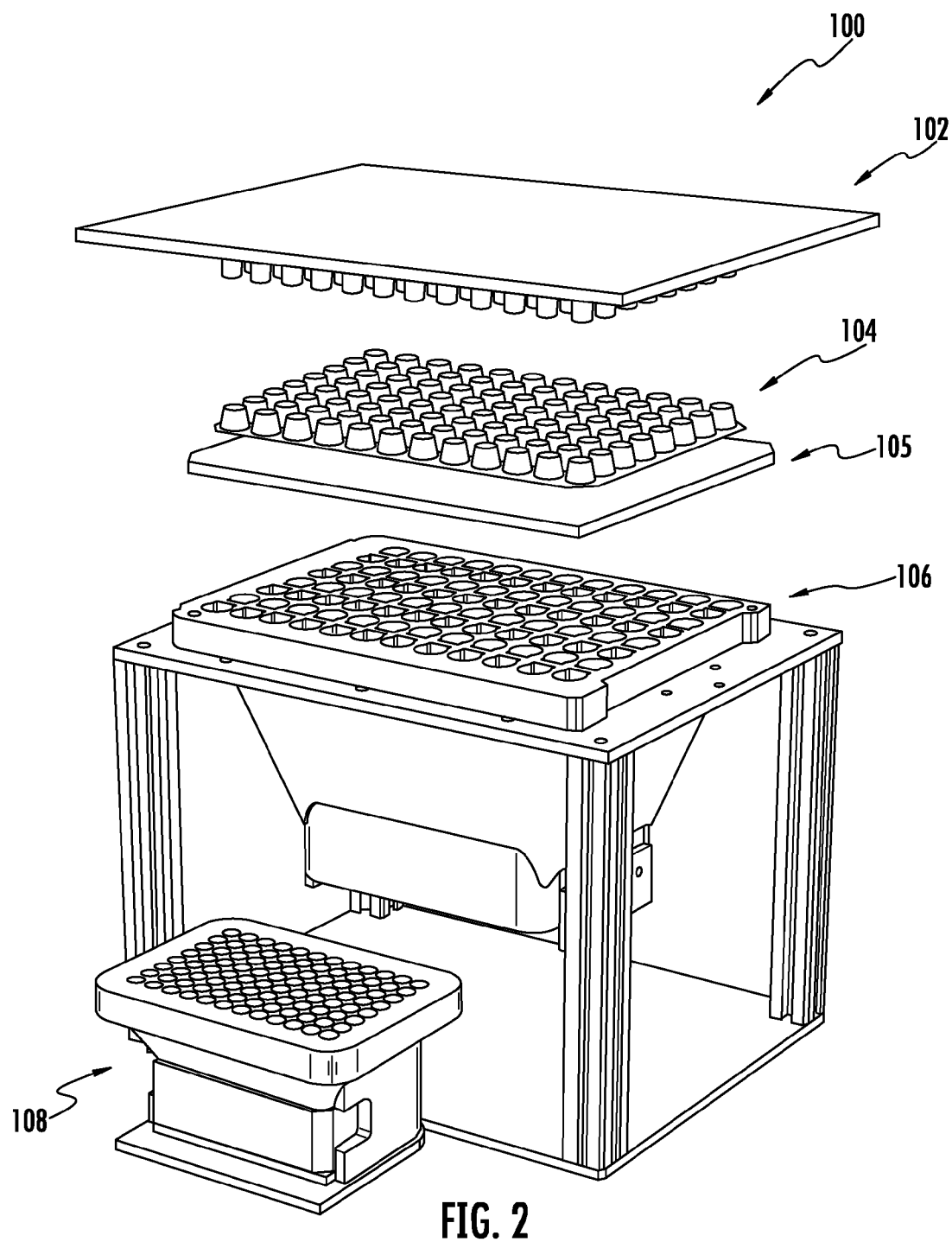
Figure 3:
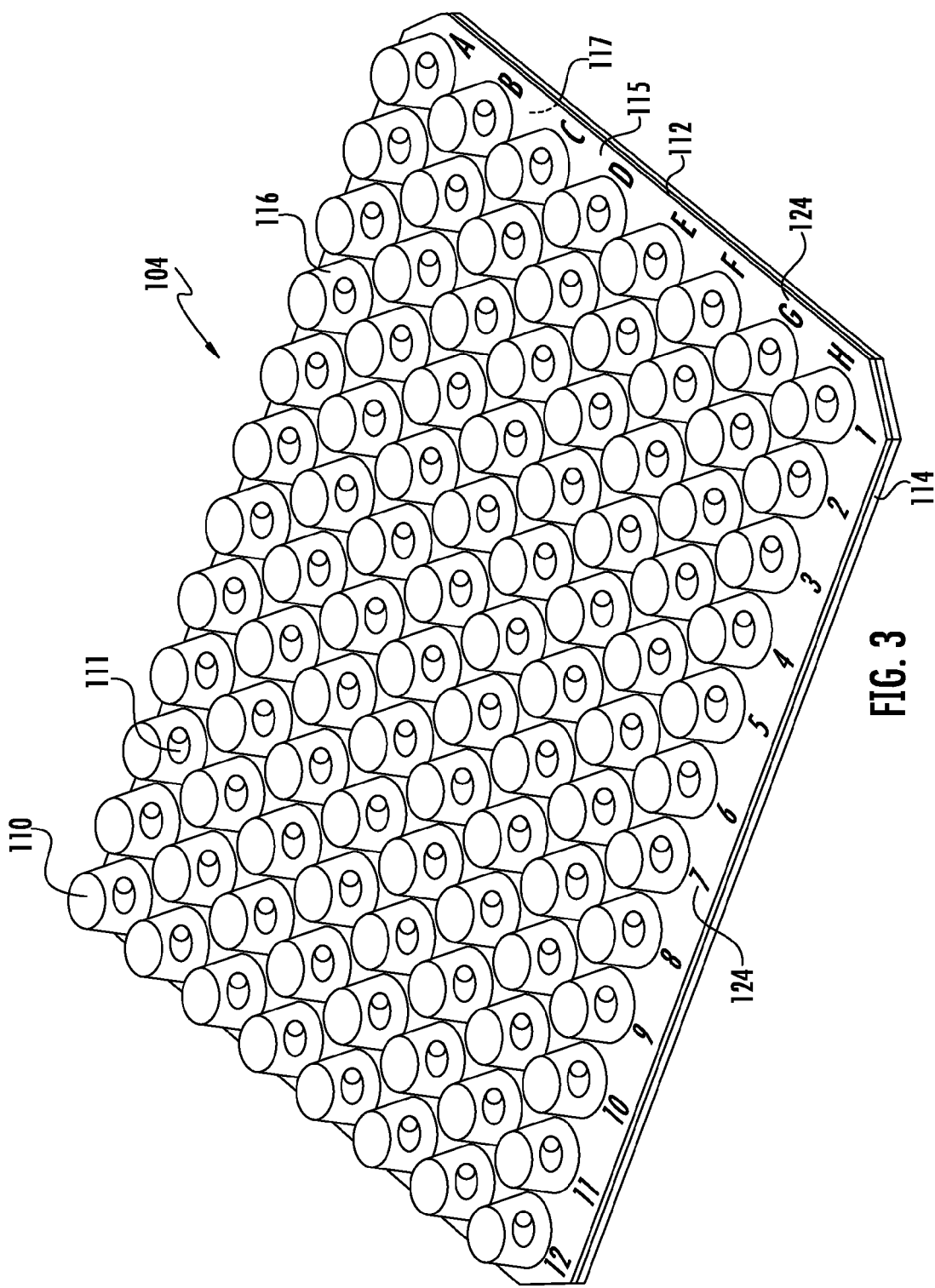
Figure 4:
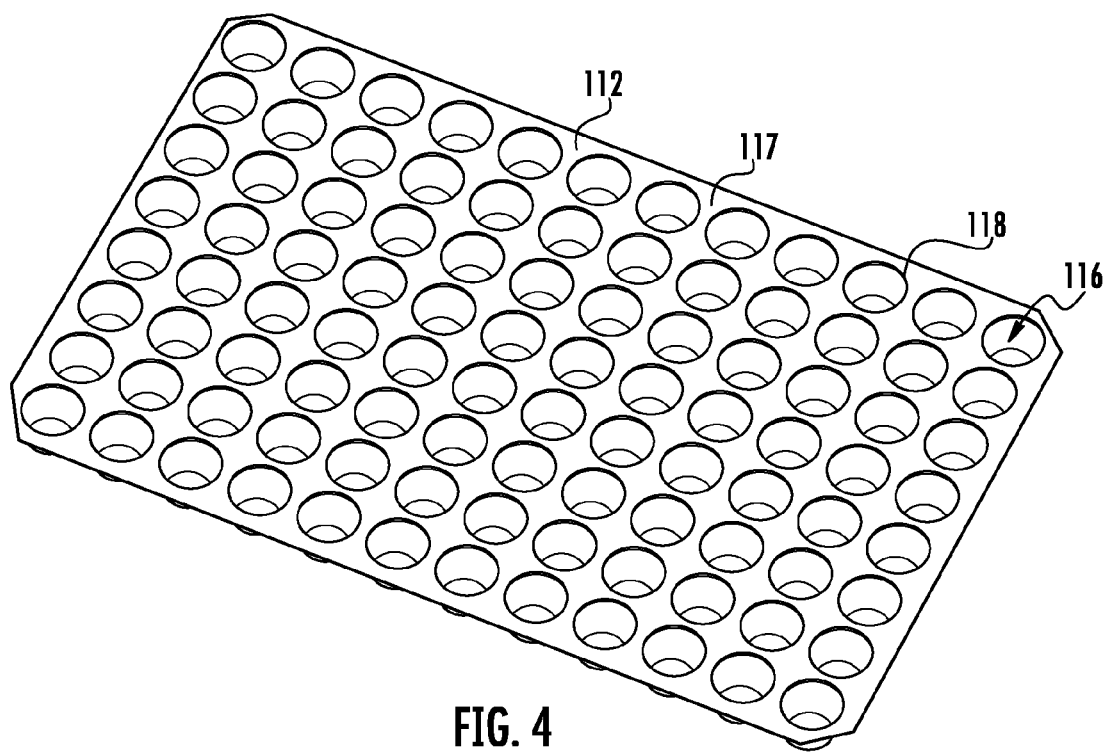
Figure 5:
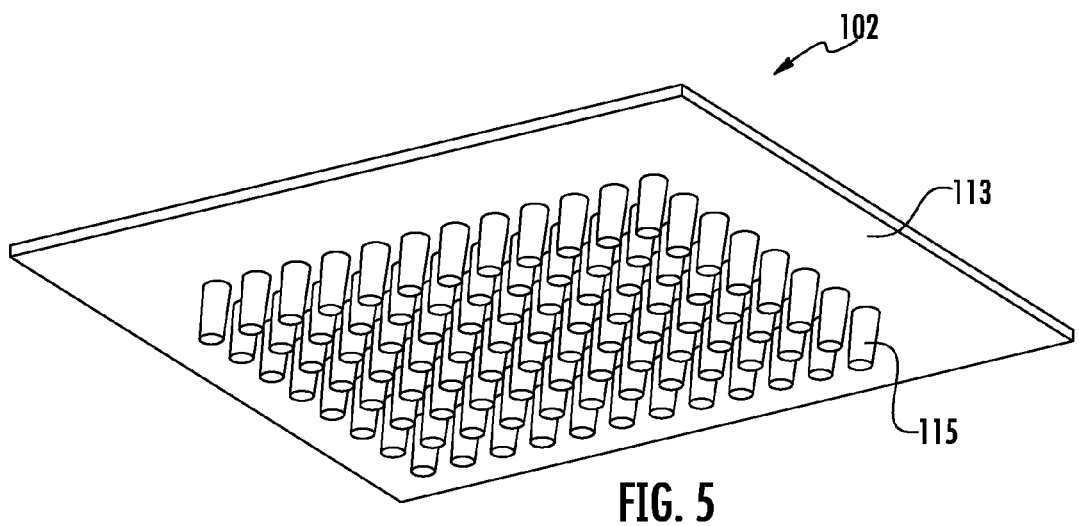
Figure 6:
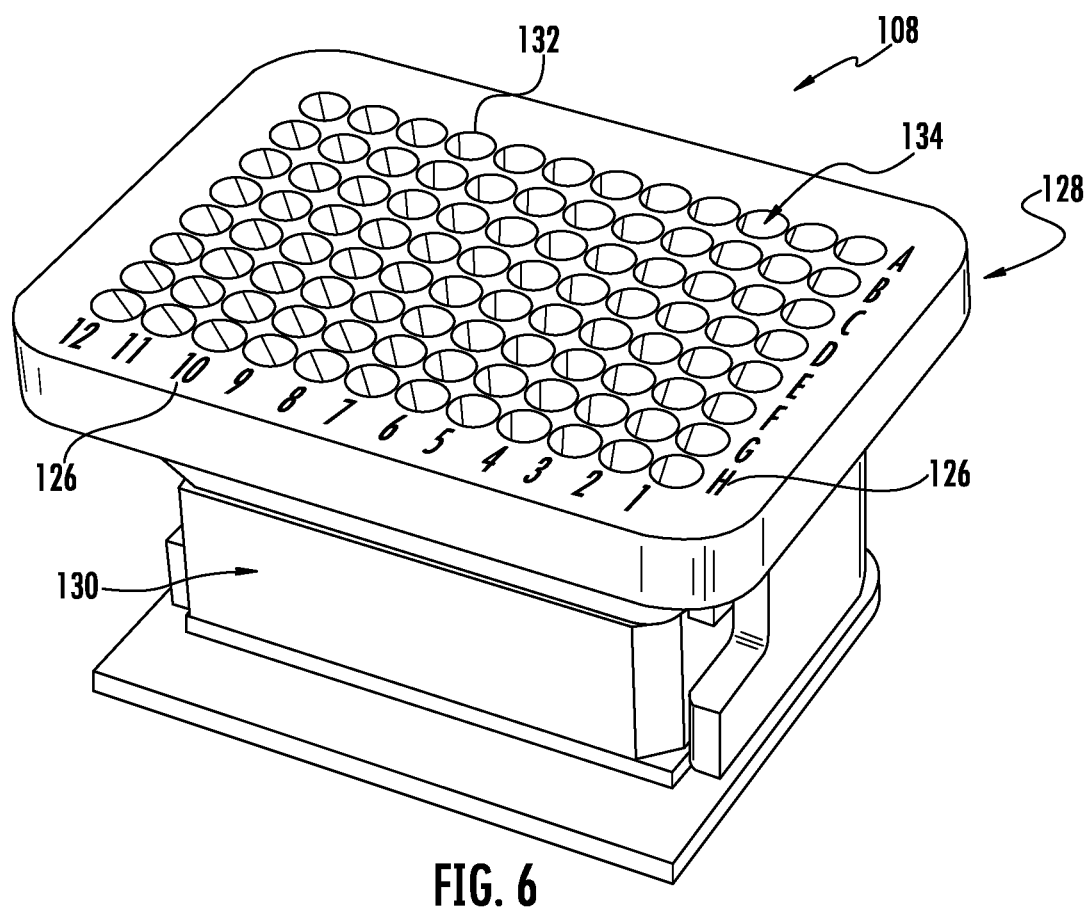
Figure 7:
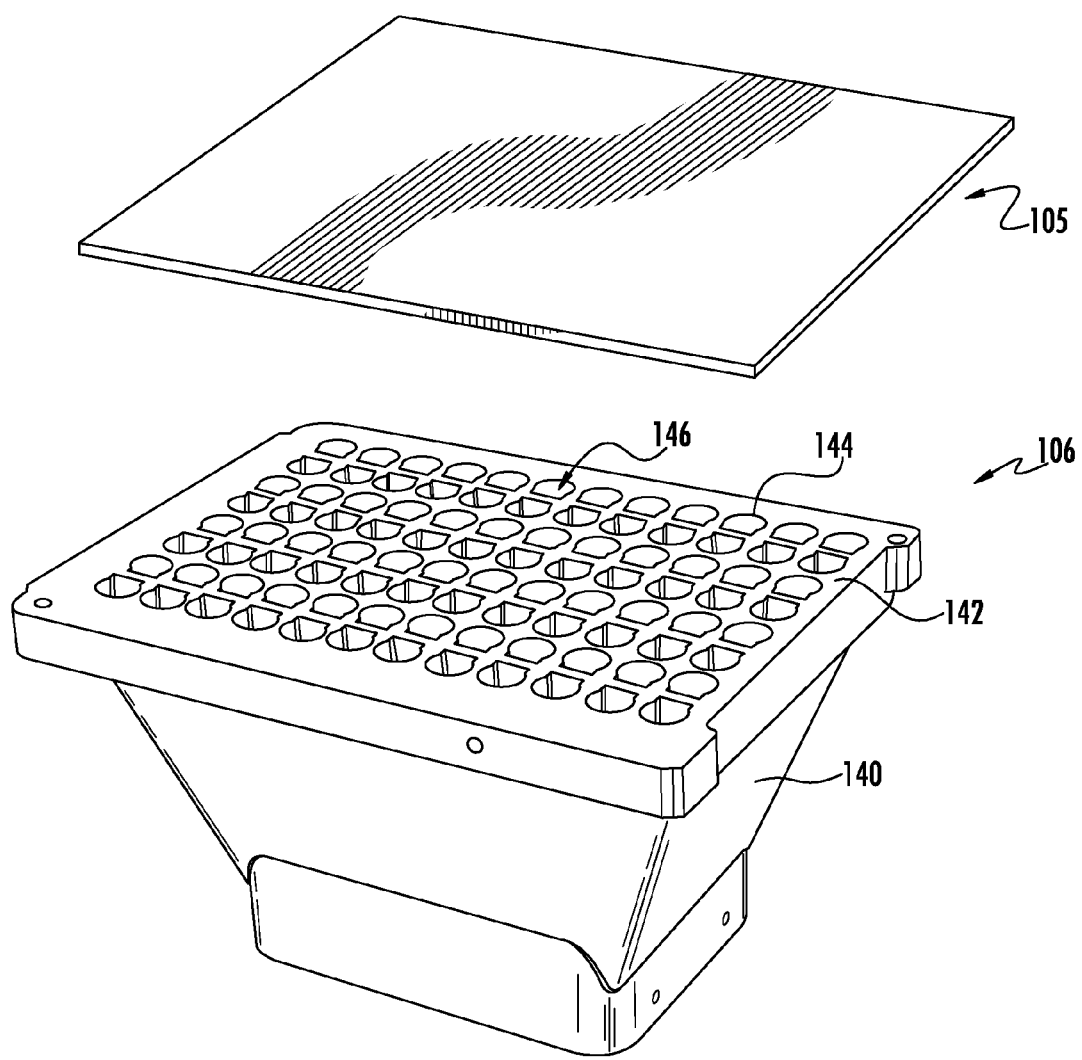
Figure 8:
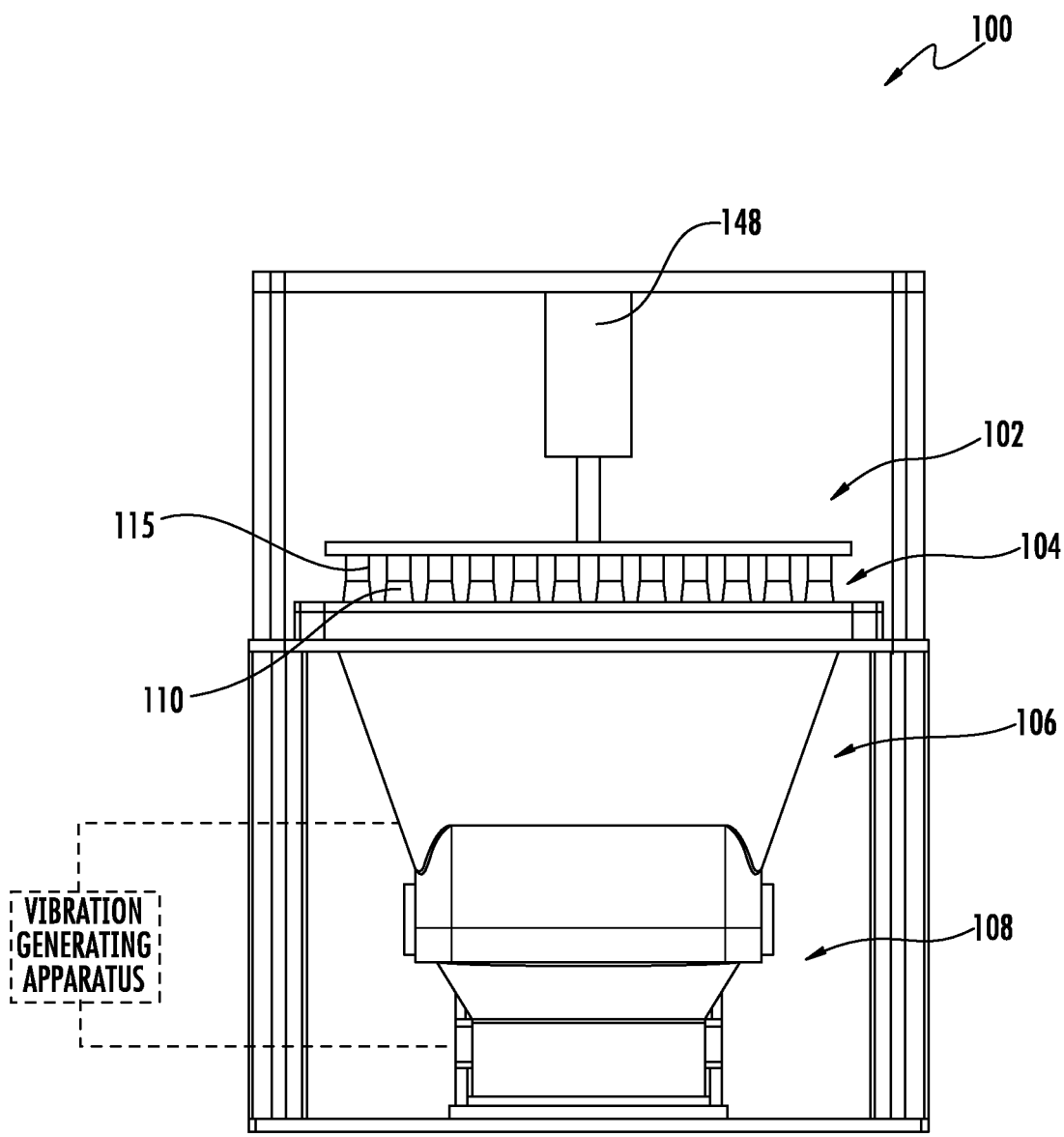
Figure 9:
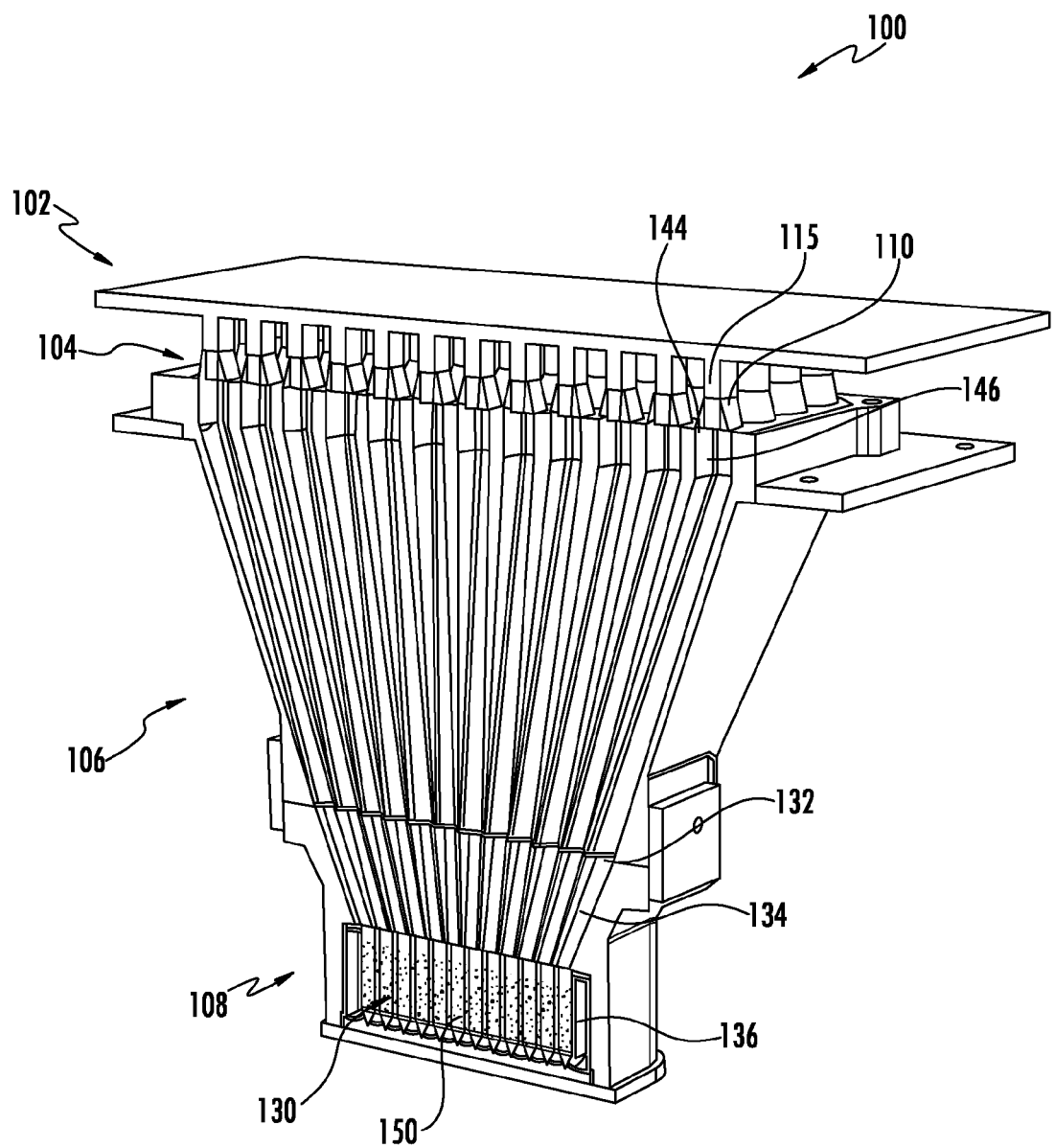
Figure 10:
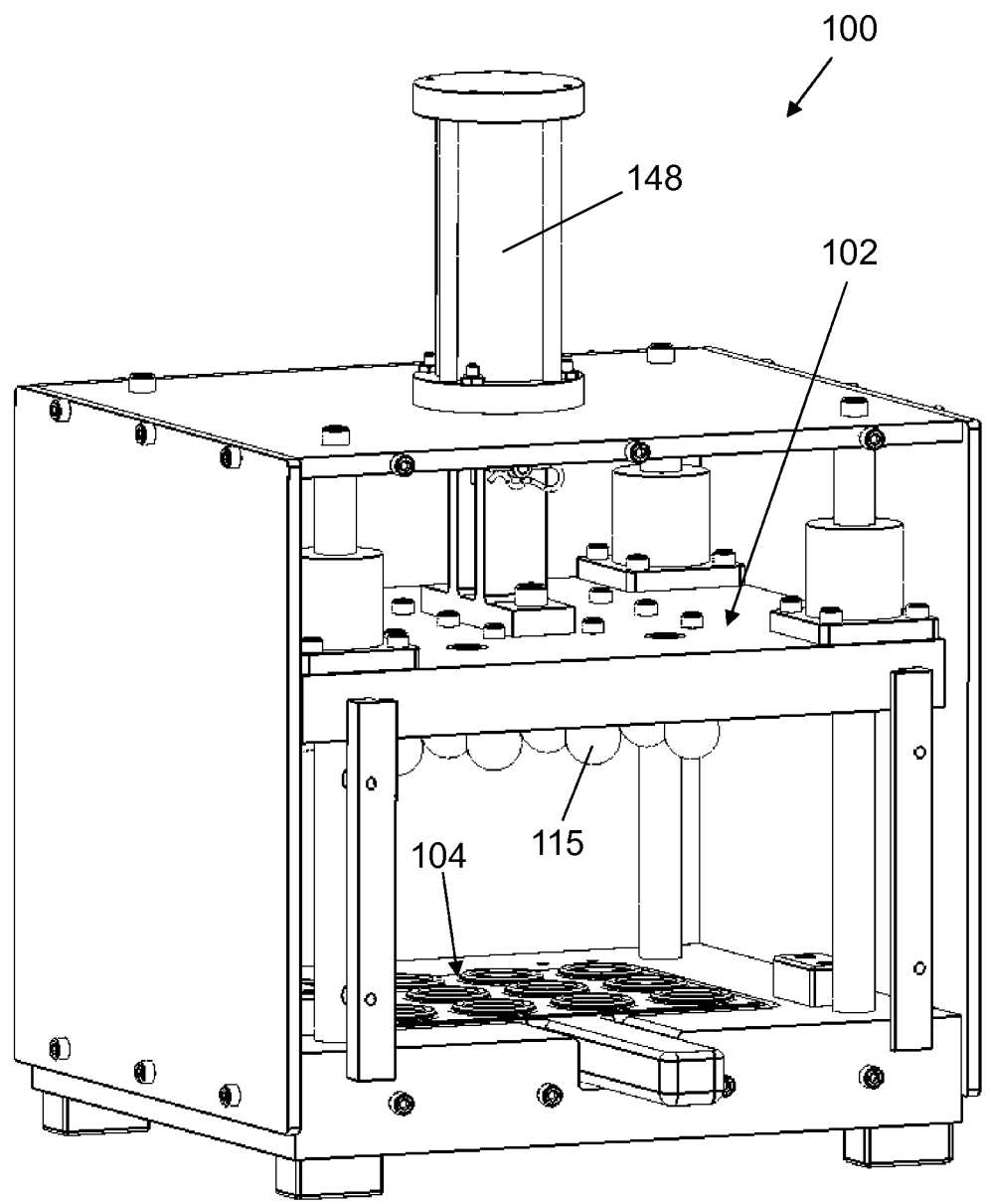
Figure 11:
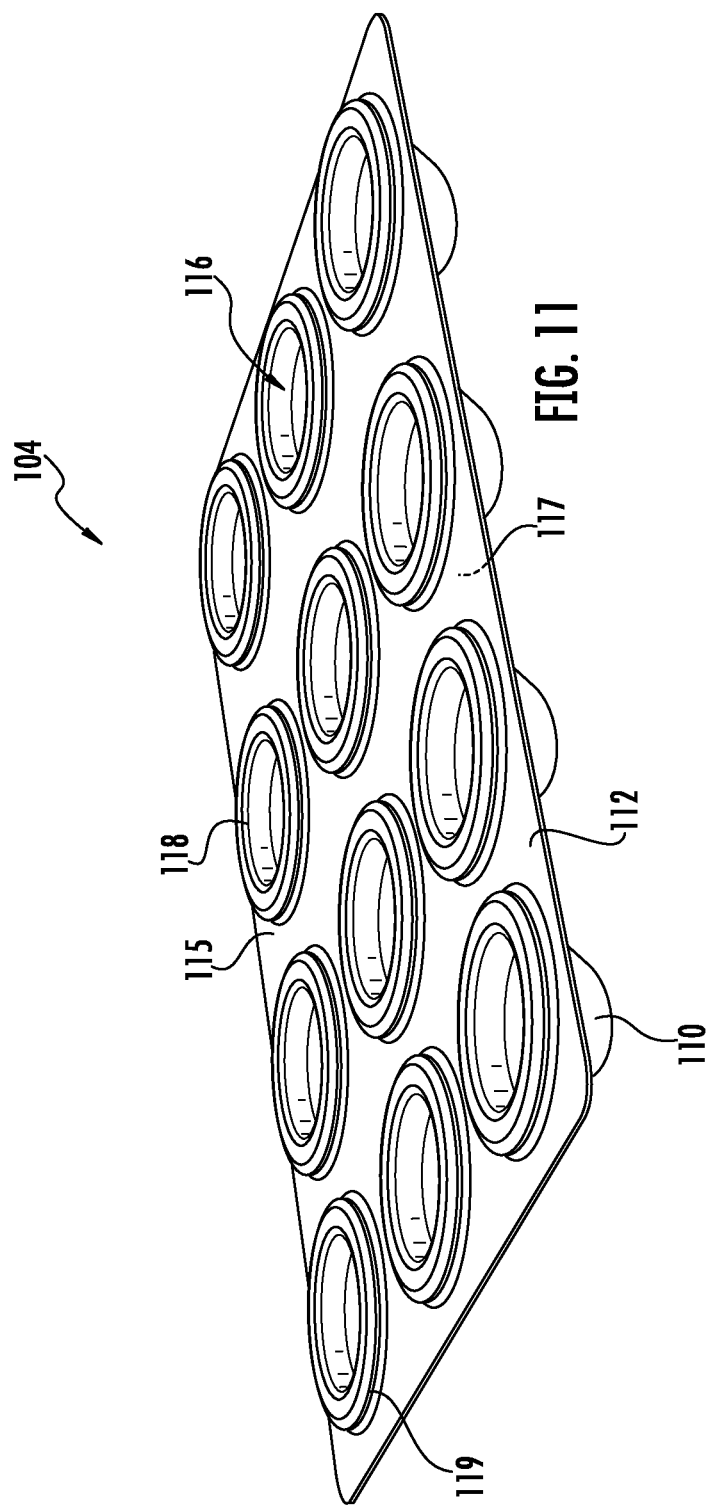
Figure 12:
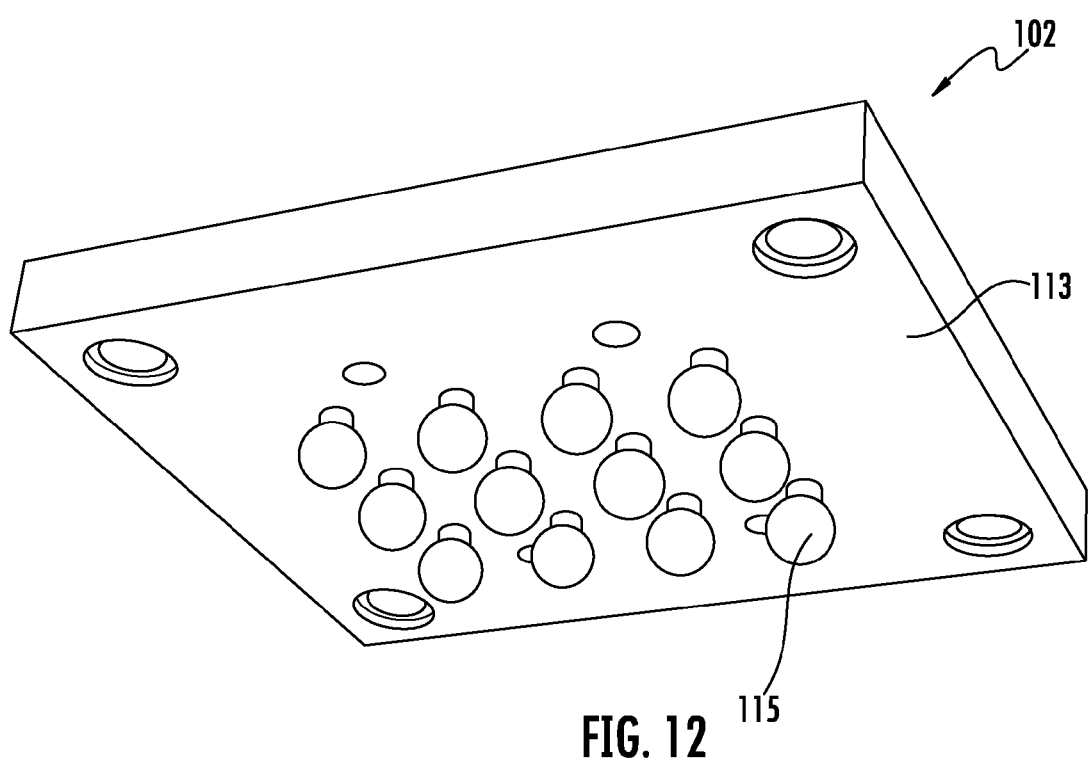
Figure 13:
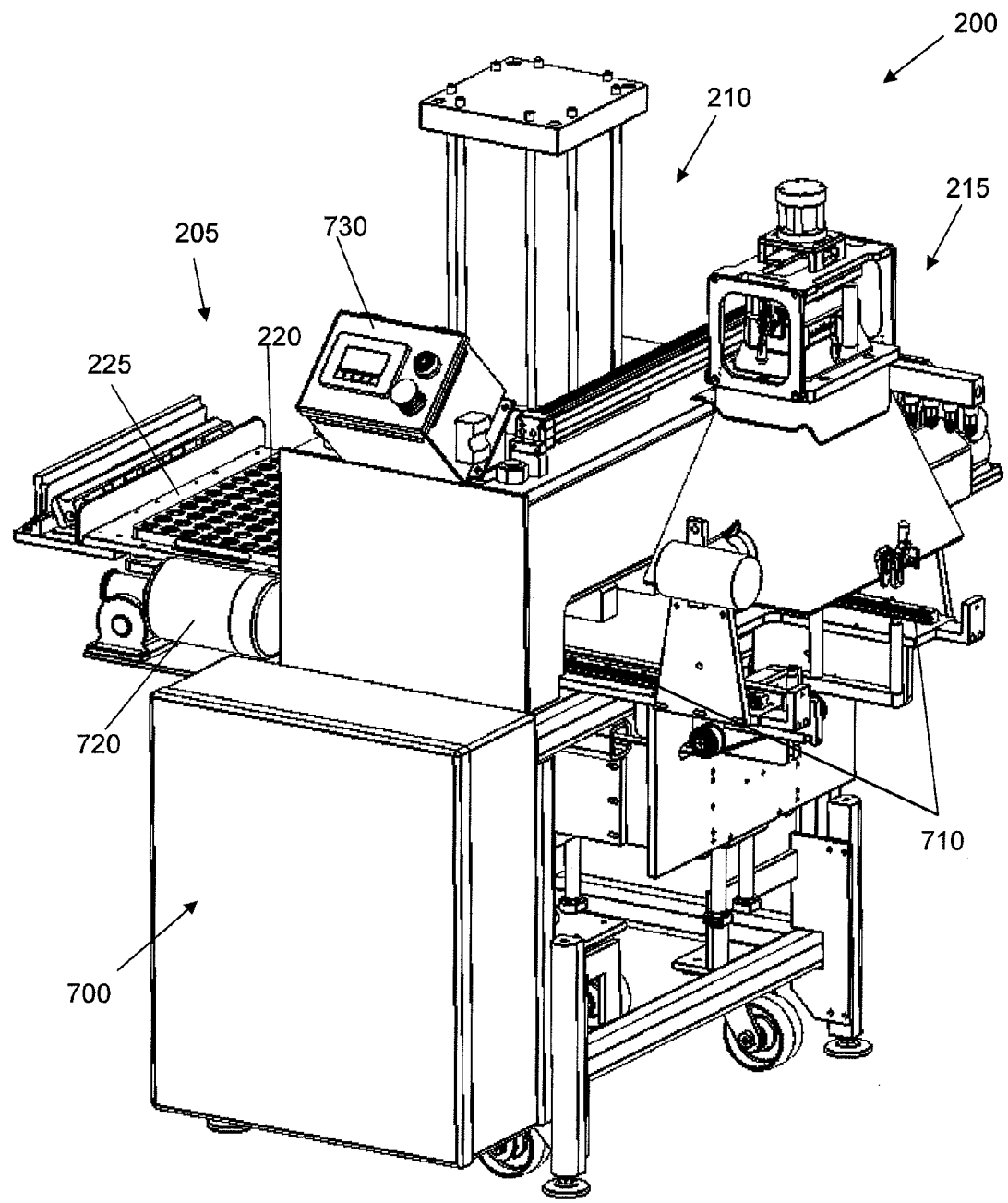
Figure 15:
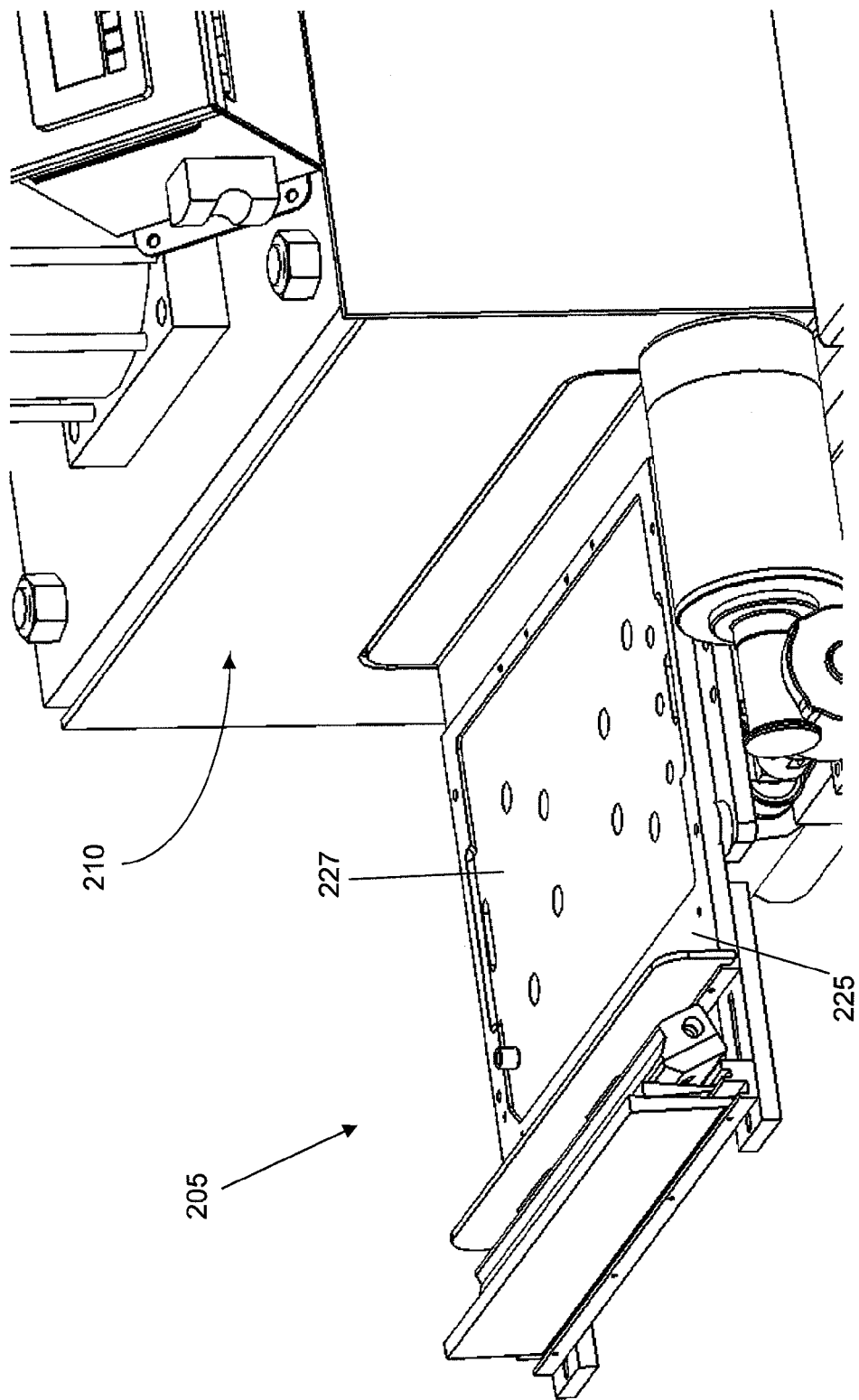
Figure 16:
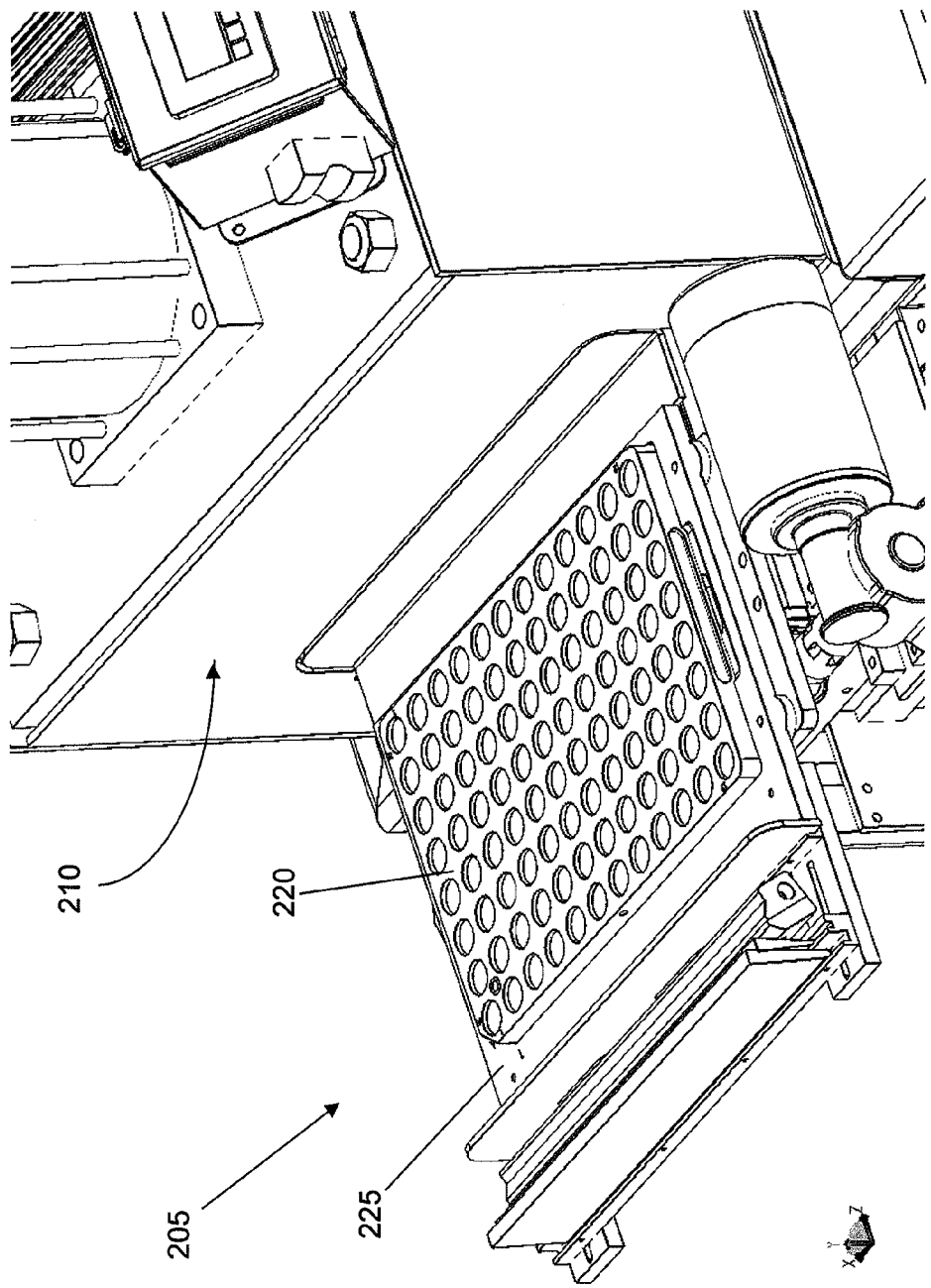
Figure 17:
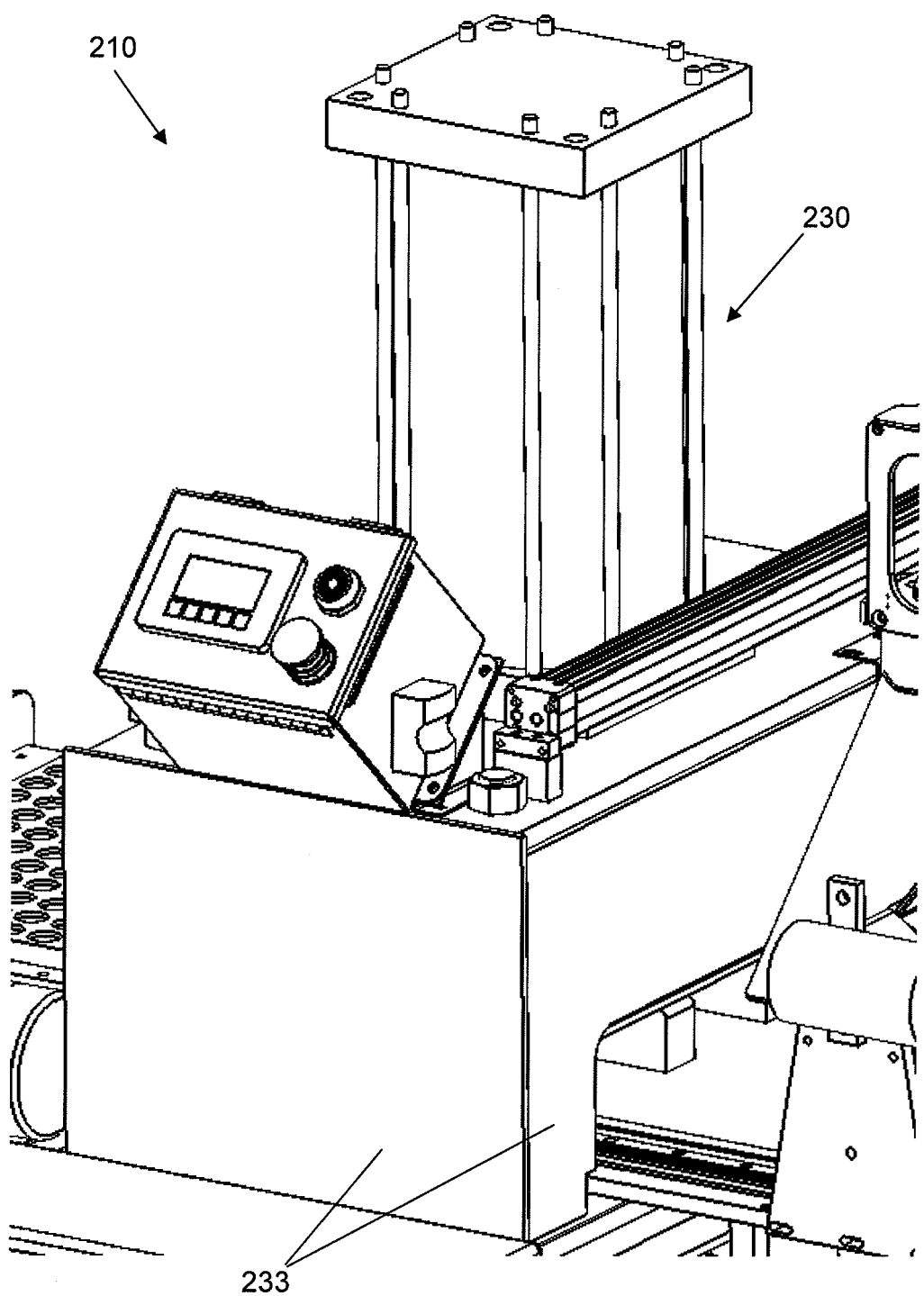
Figure 18:
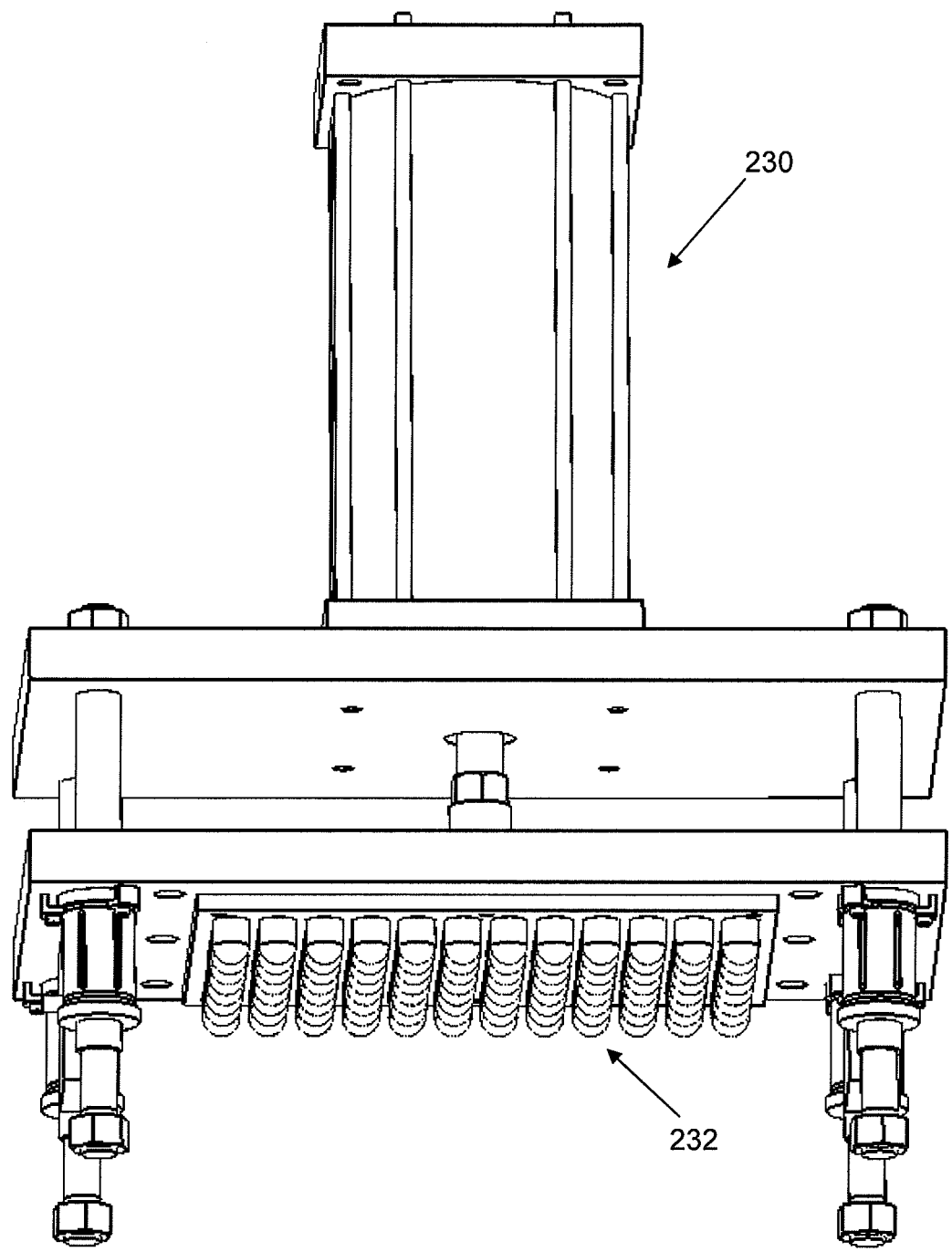
Figure 19:
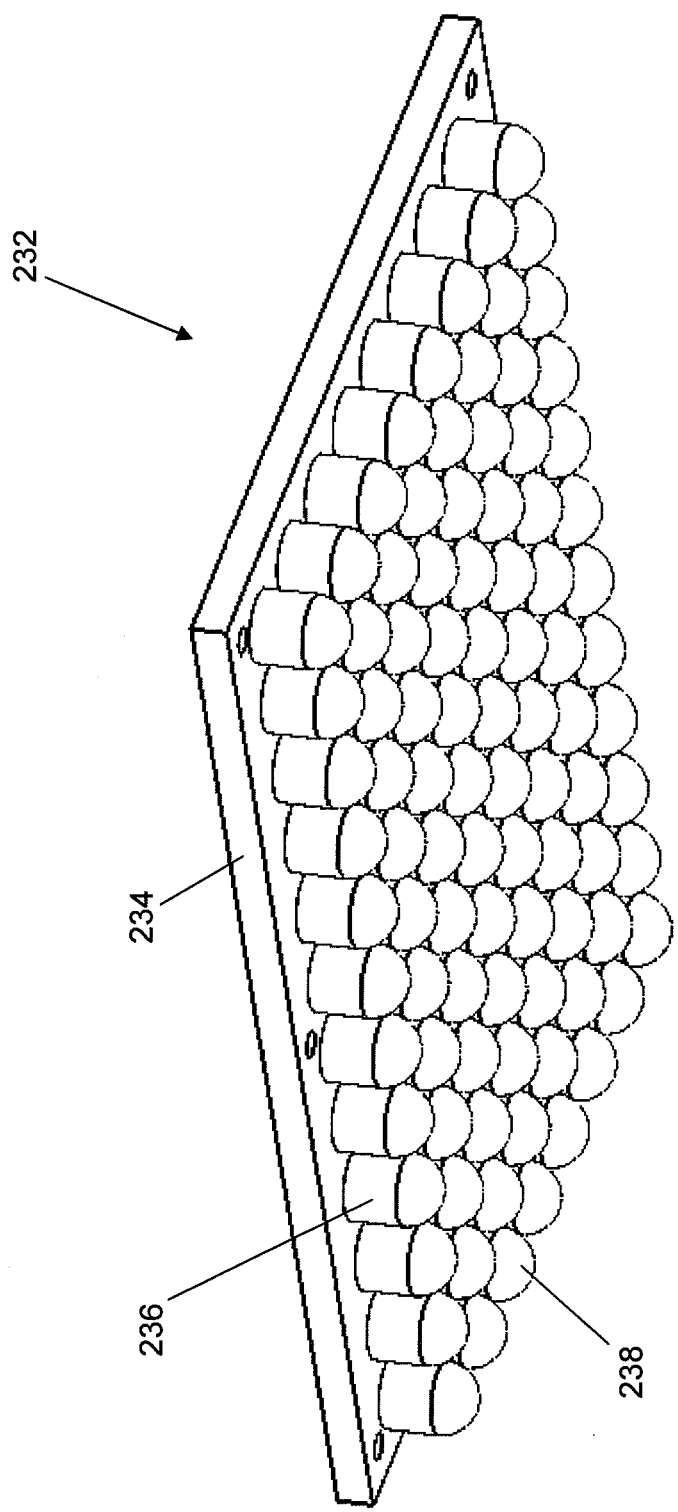
Figure 20:
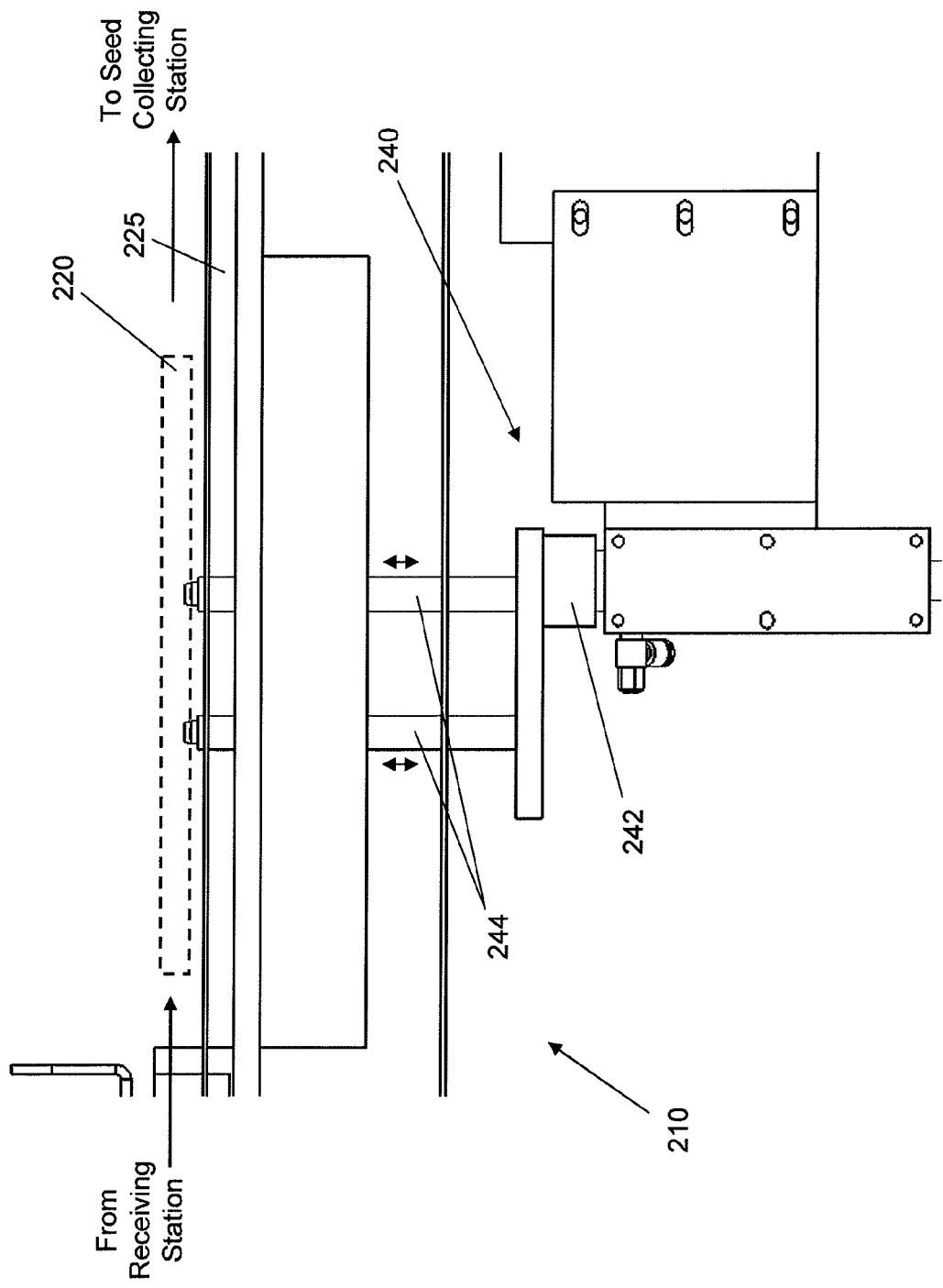
Figure 21:
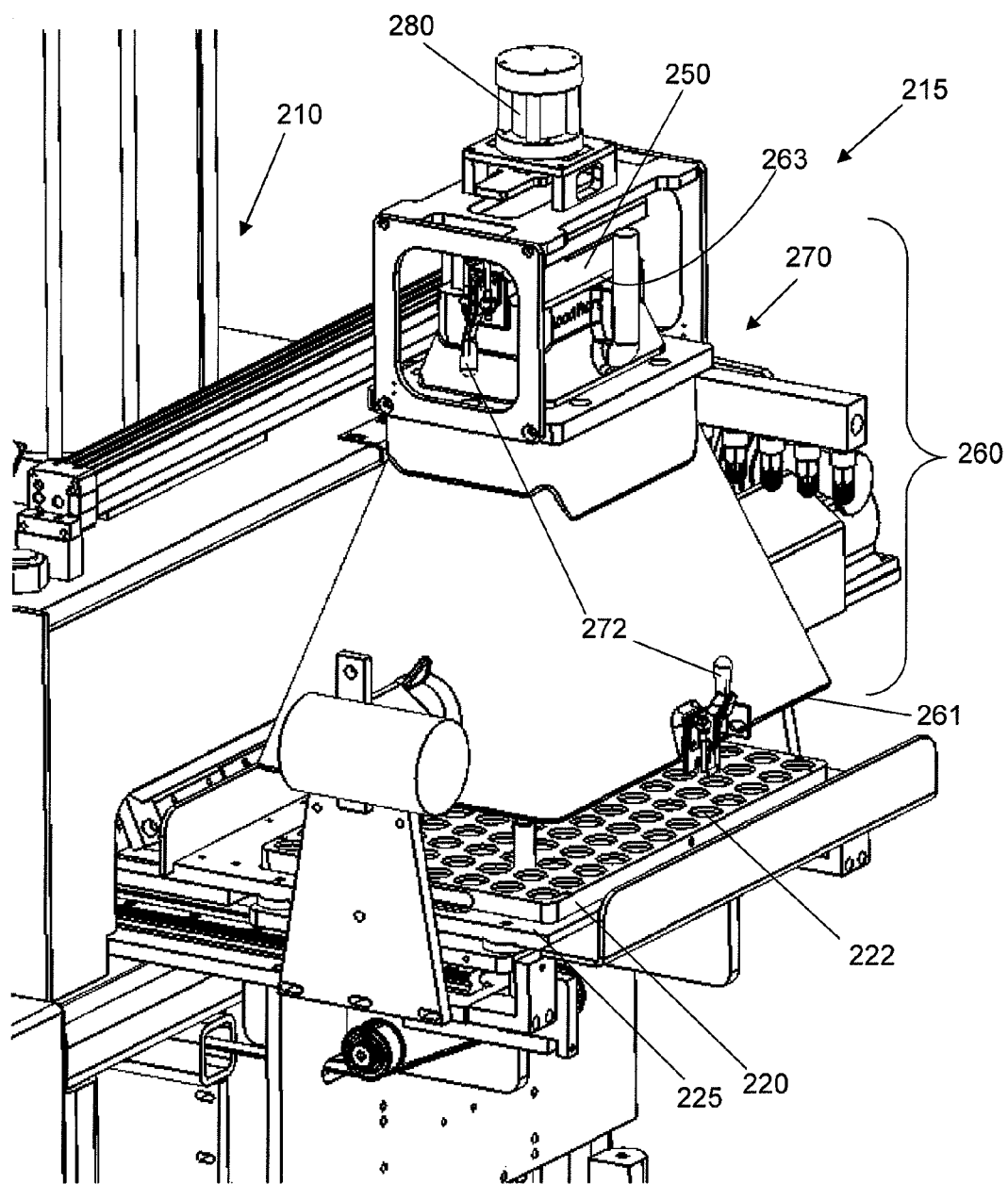
Figure 22:
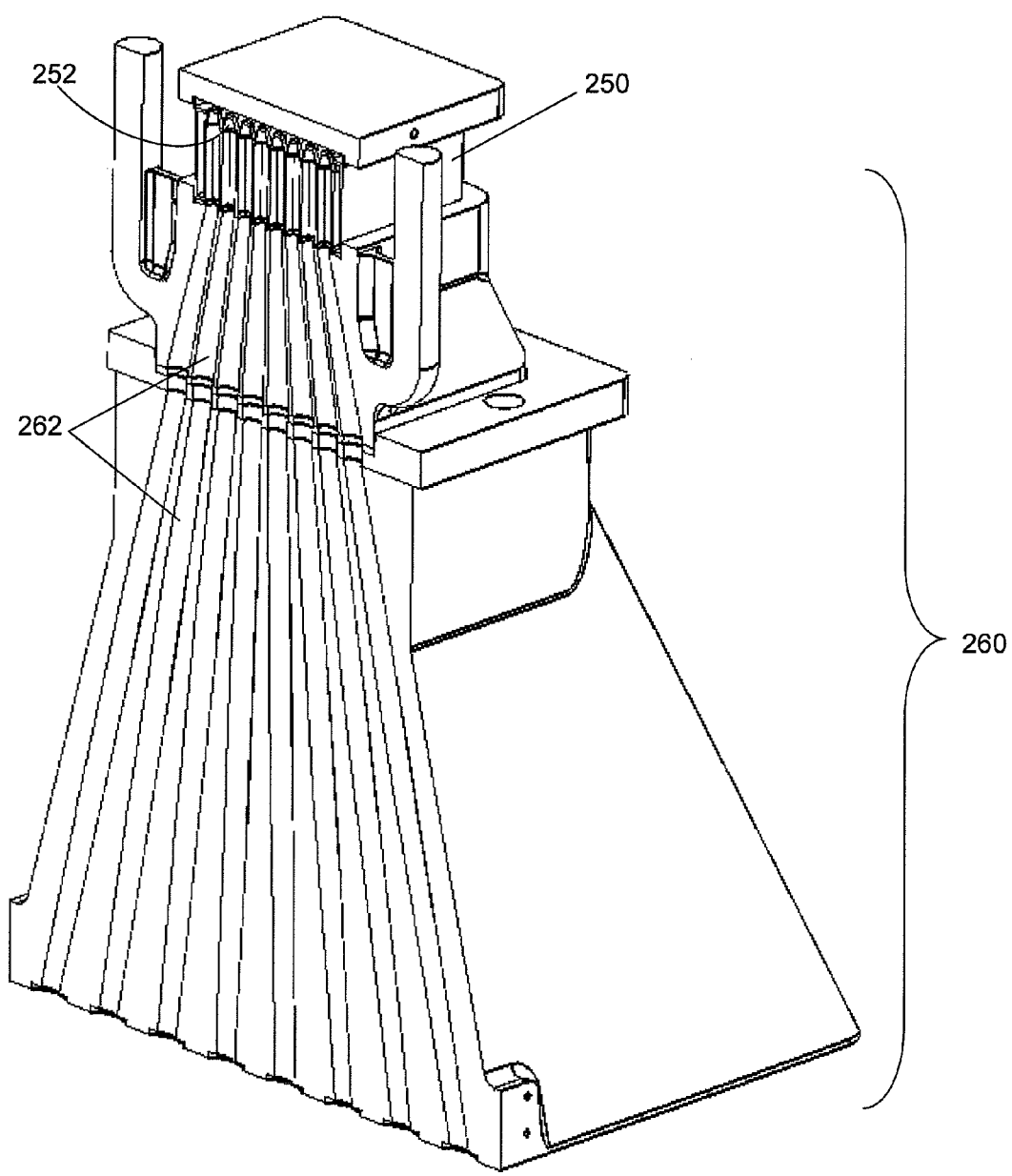
Figure 23:
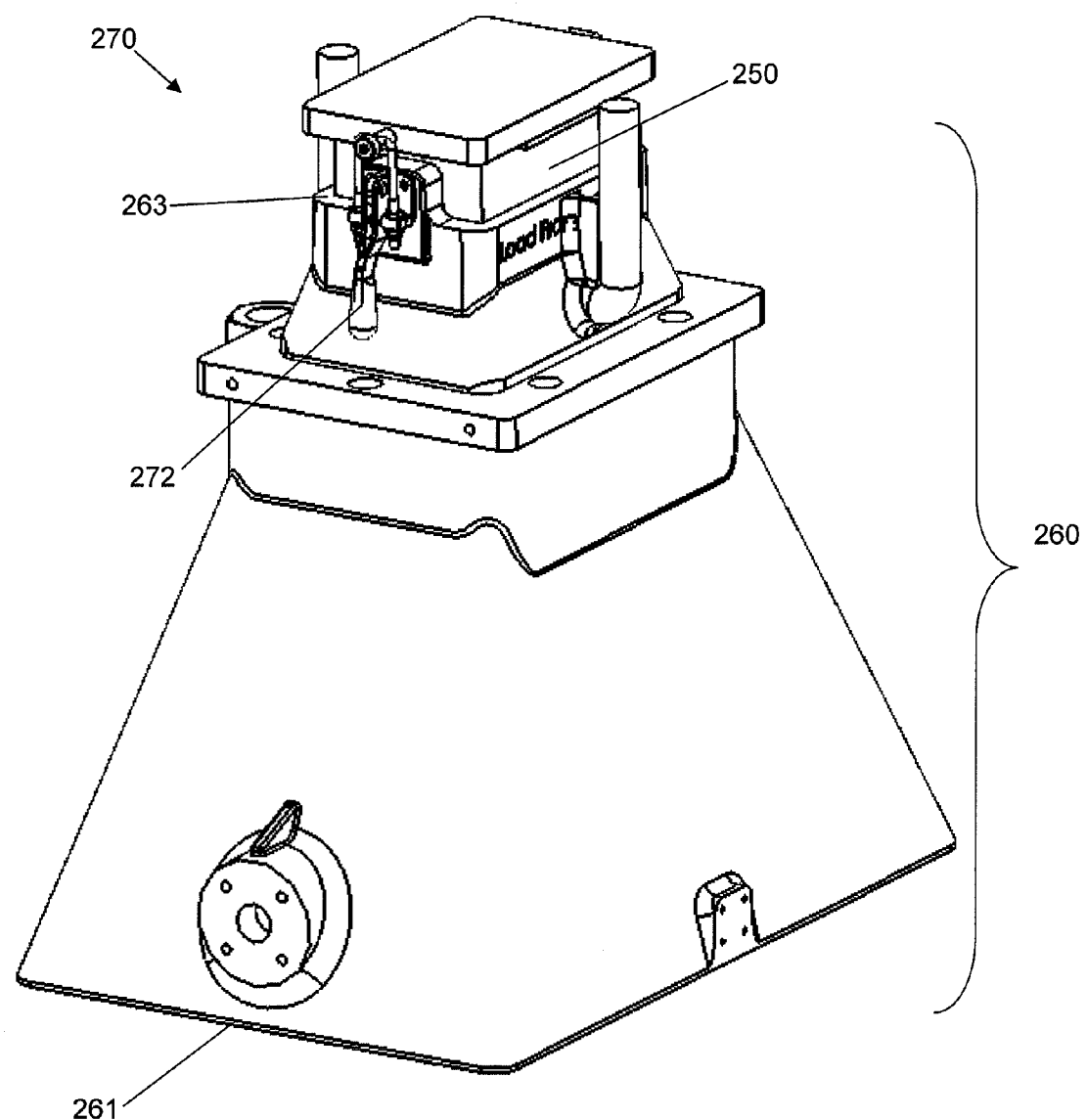
Figure 24:
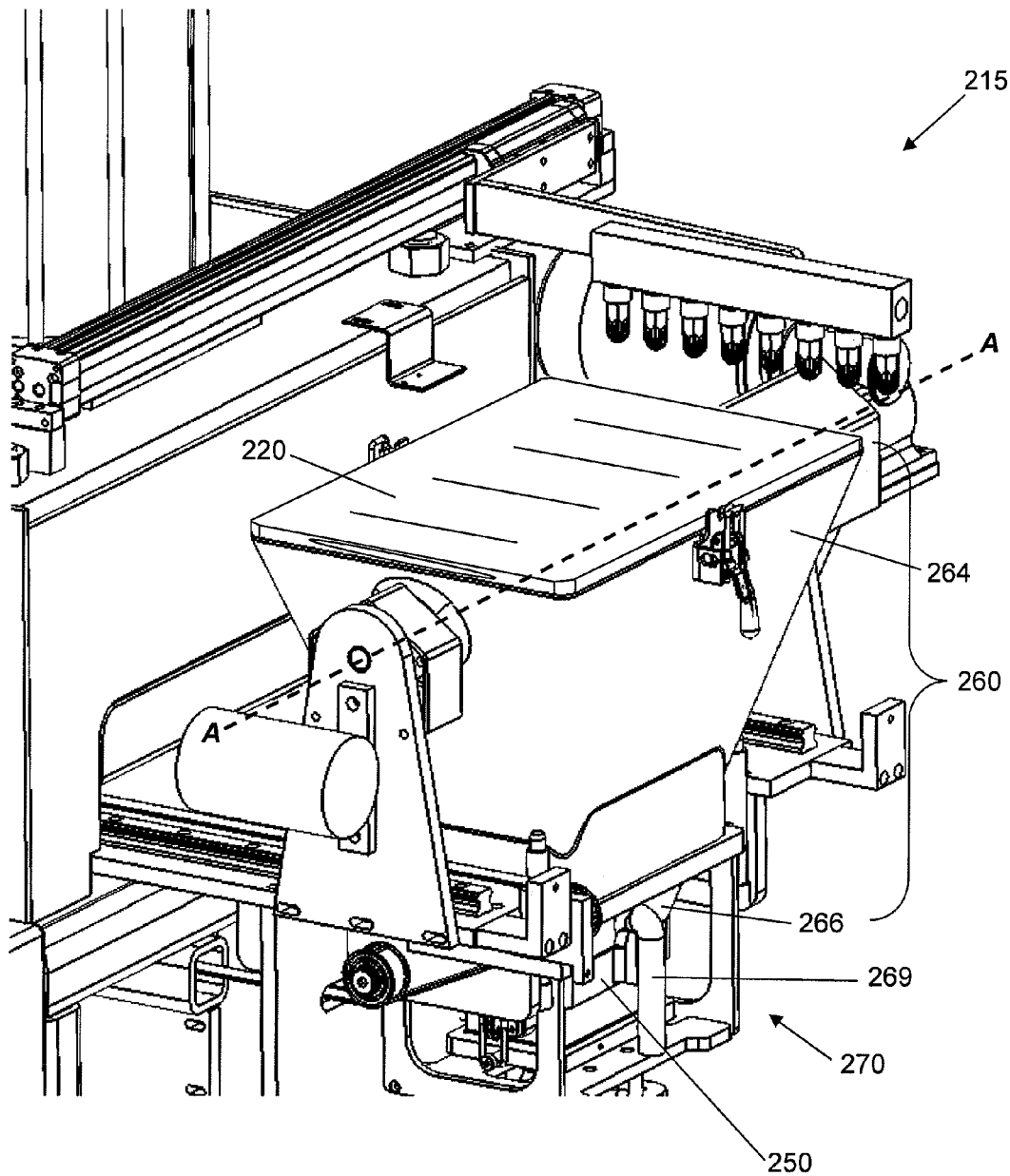
Figure 25:
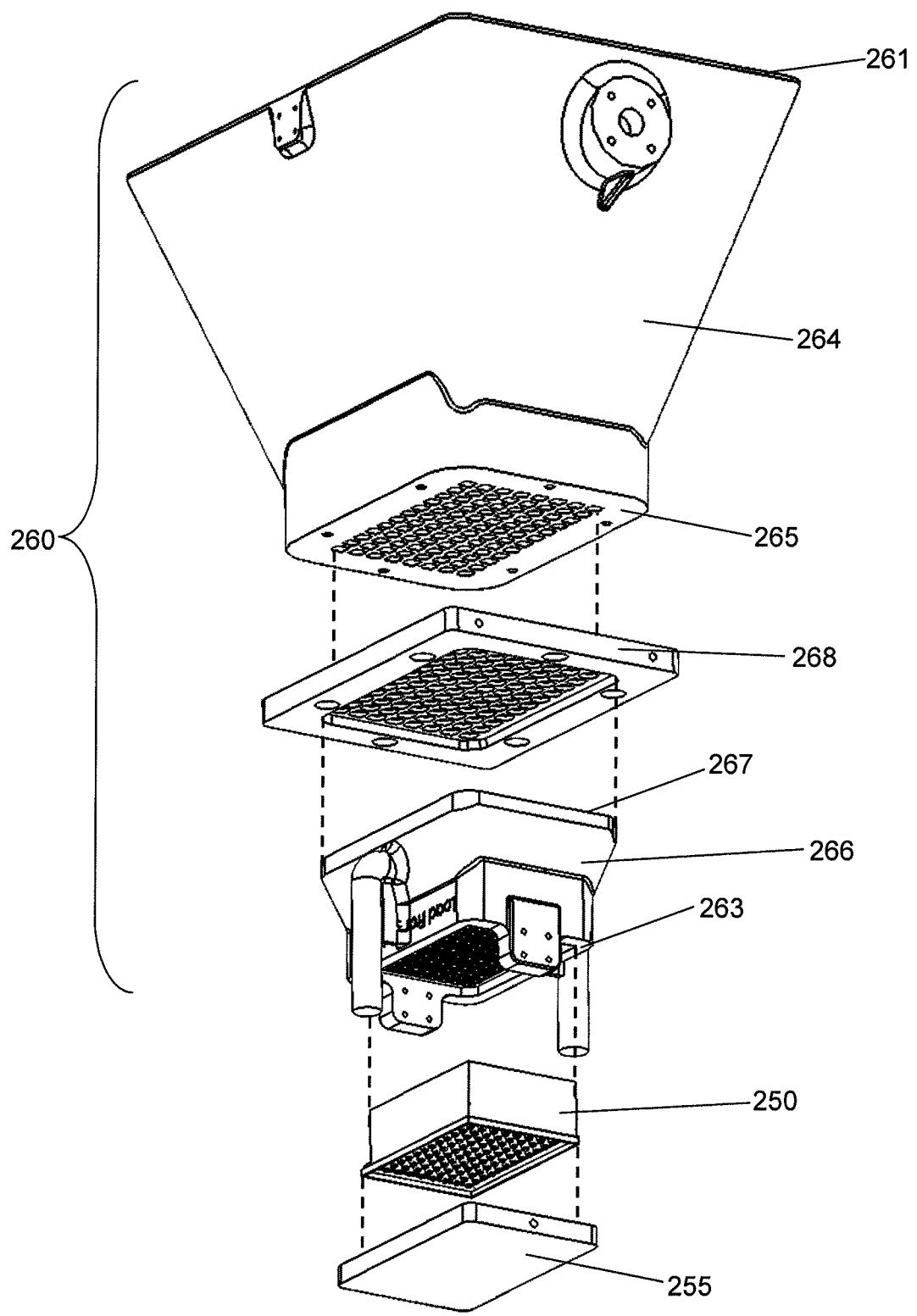
Figure 26:
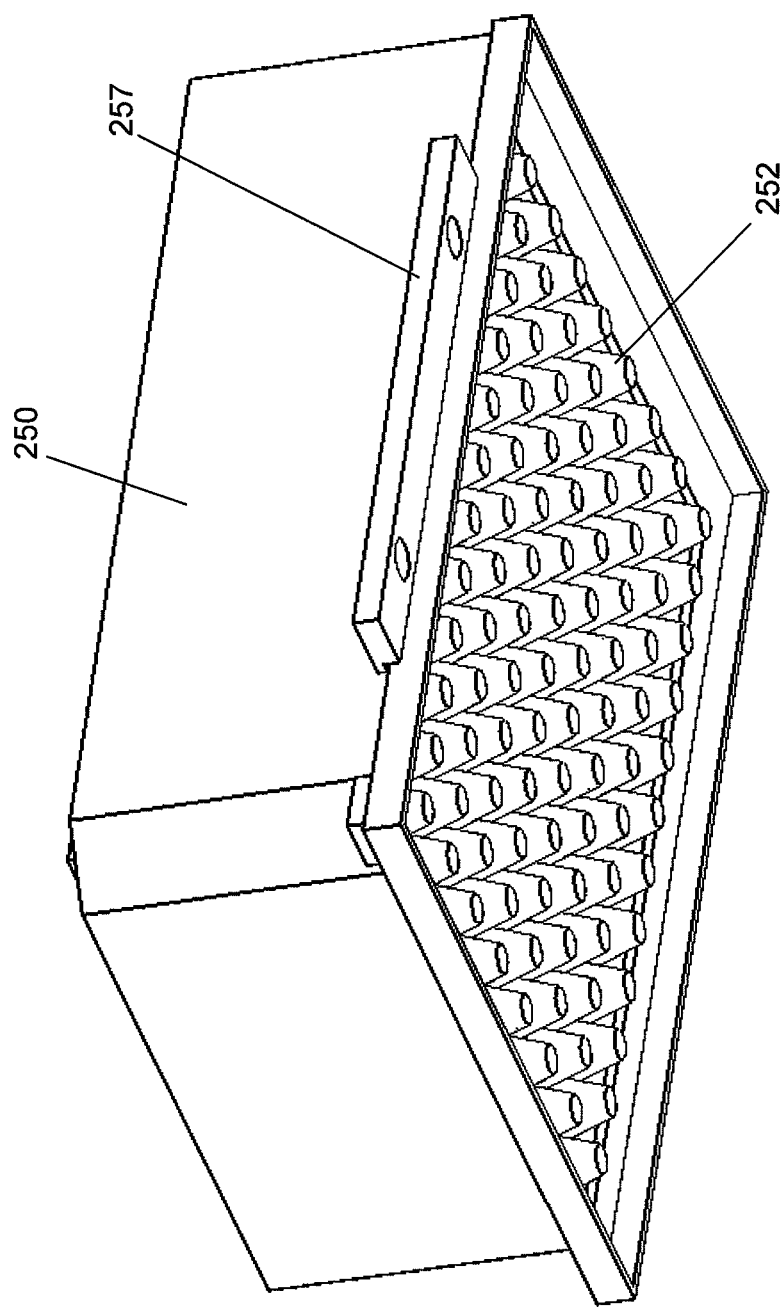
Figures 27A, 27B:
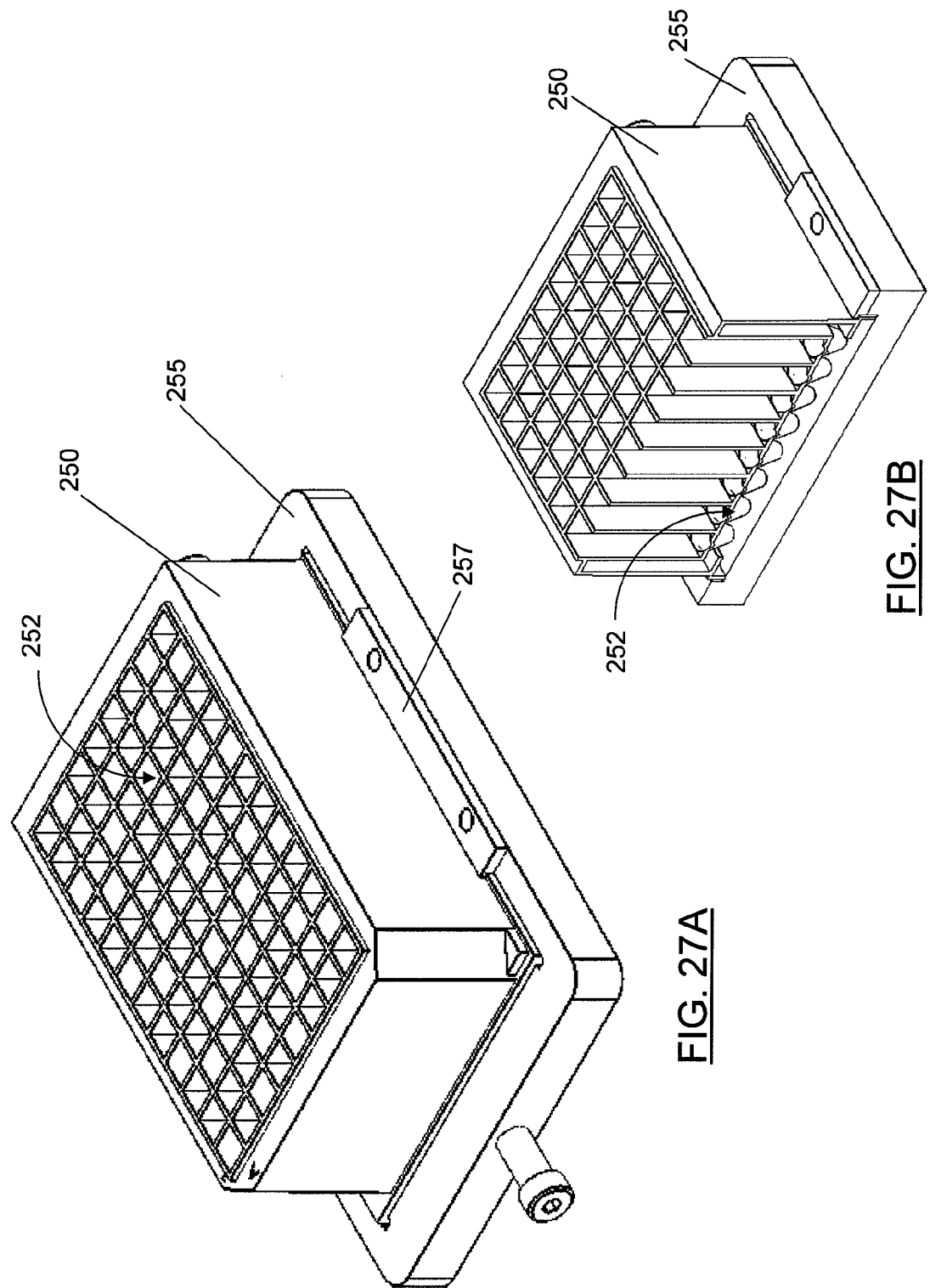
Figure 28:
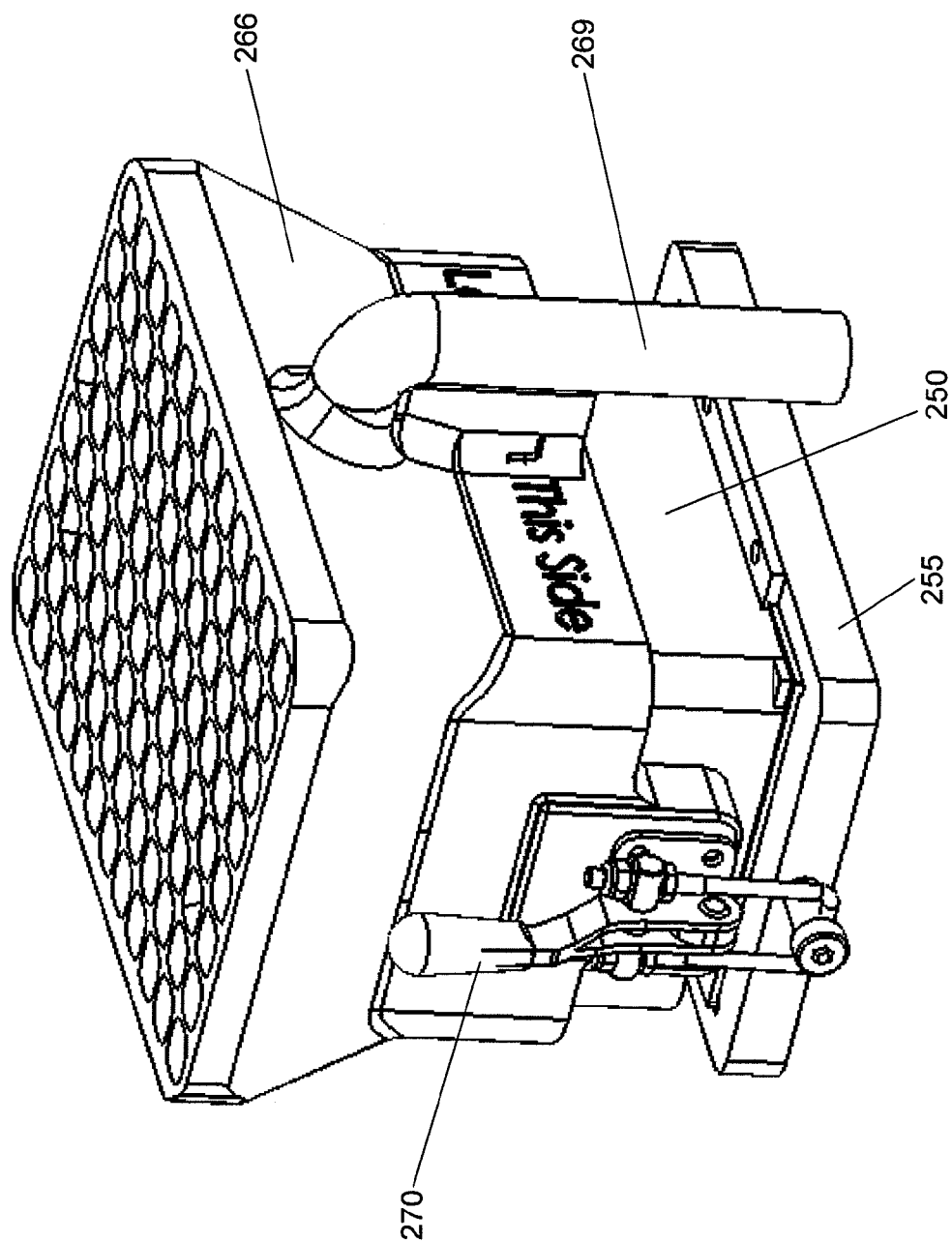
Figure 29:
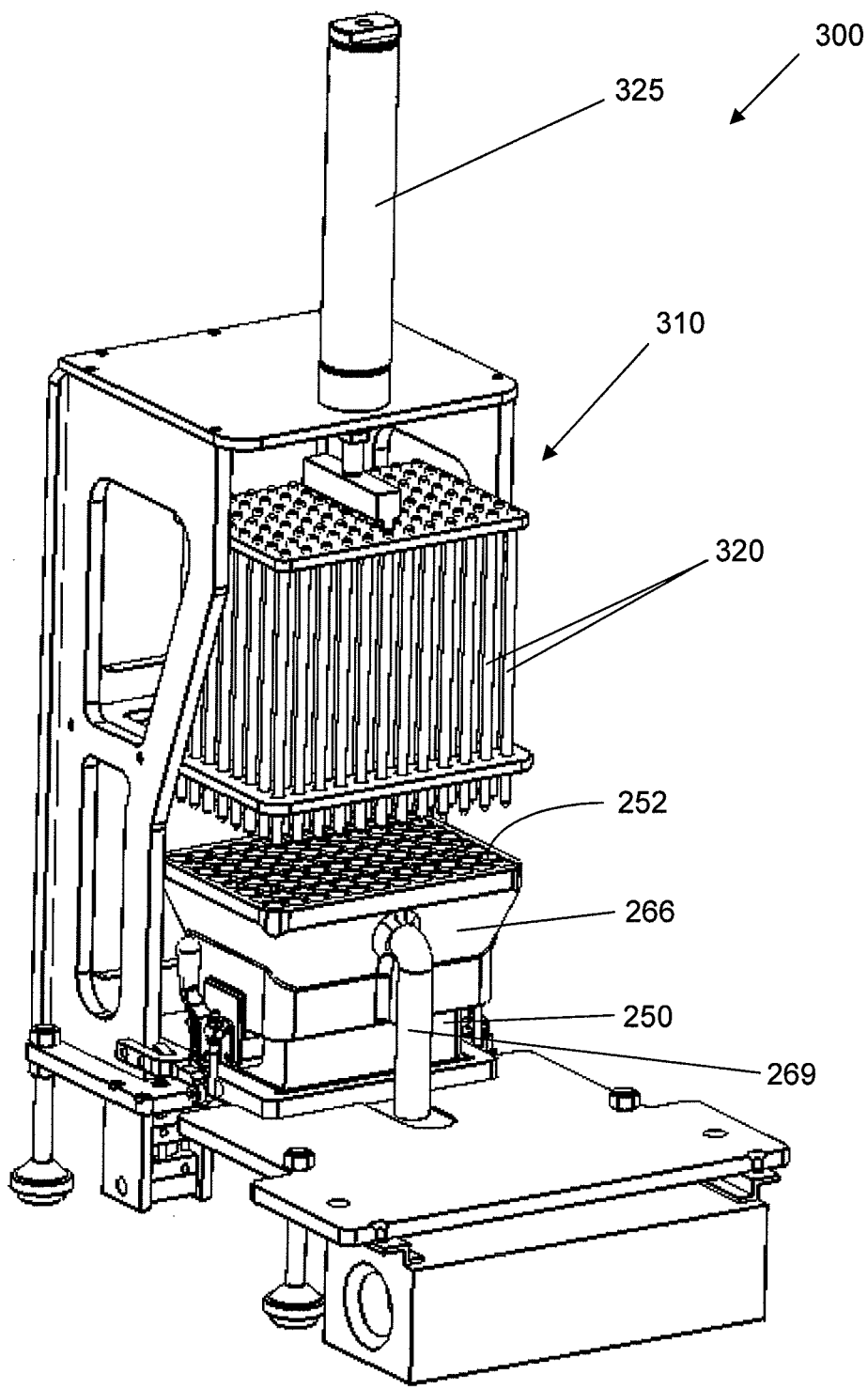
Figure 30:
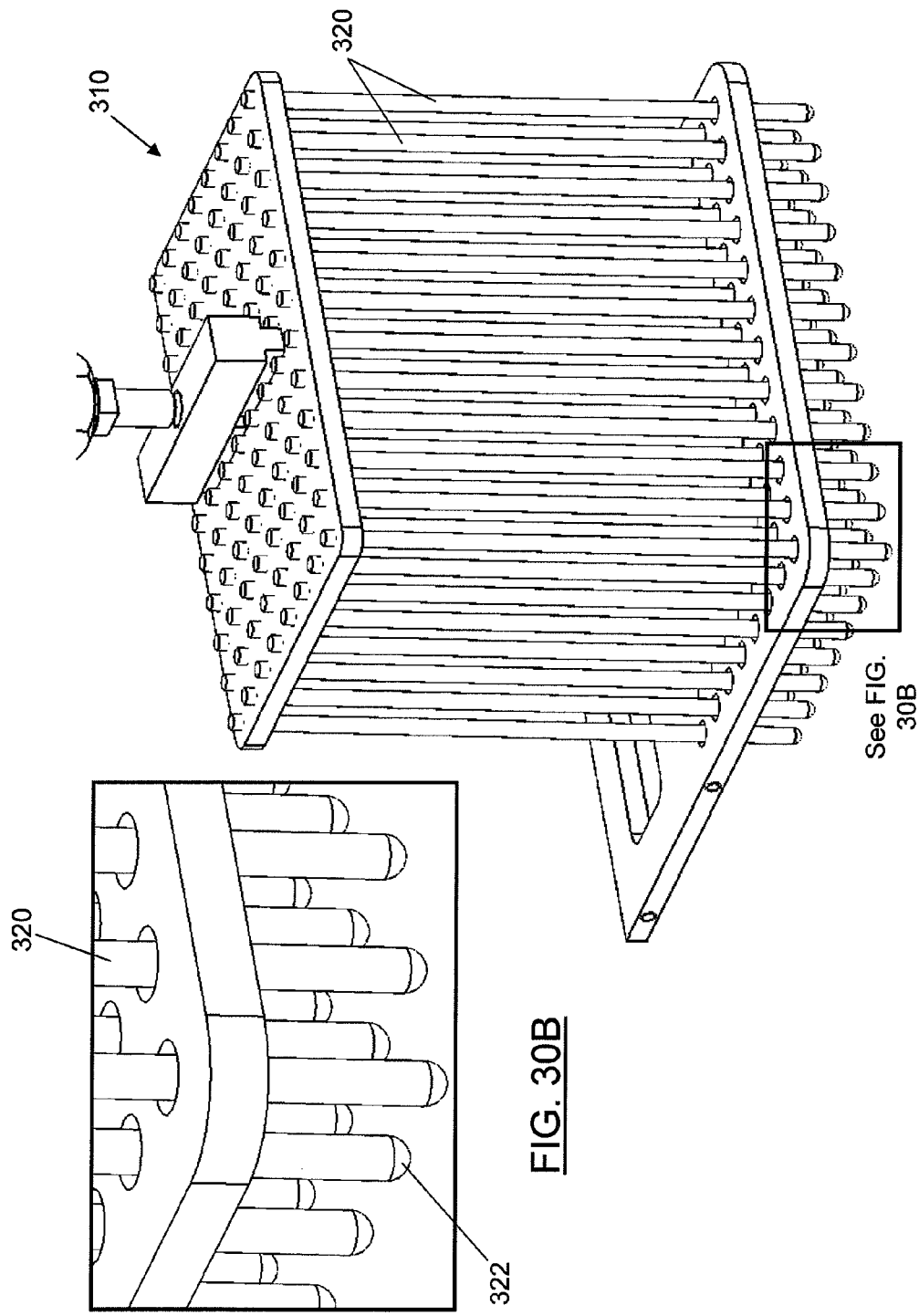
Figure 31:
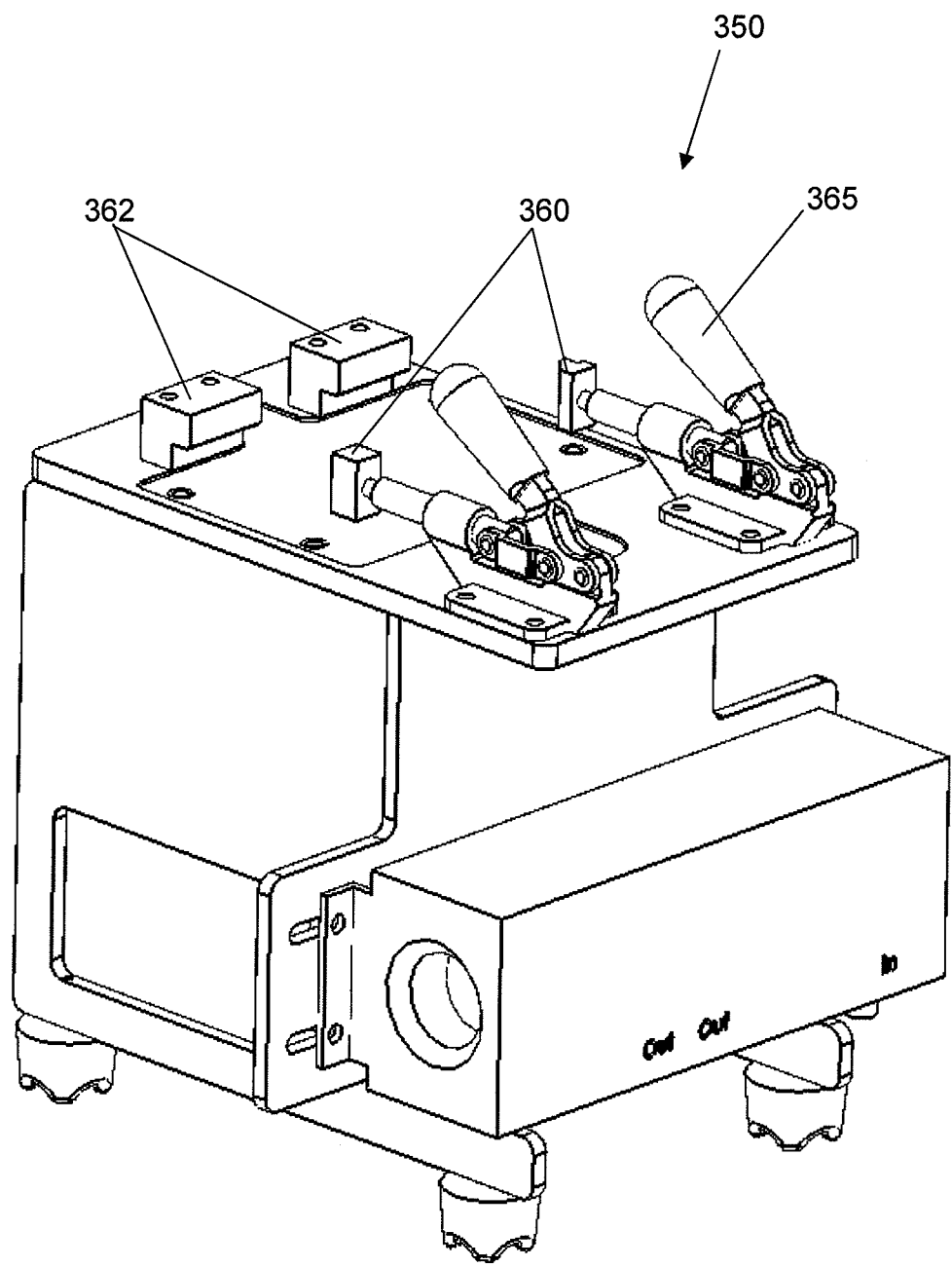
Figure 32:
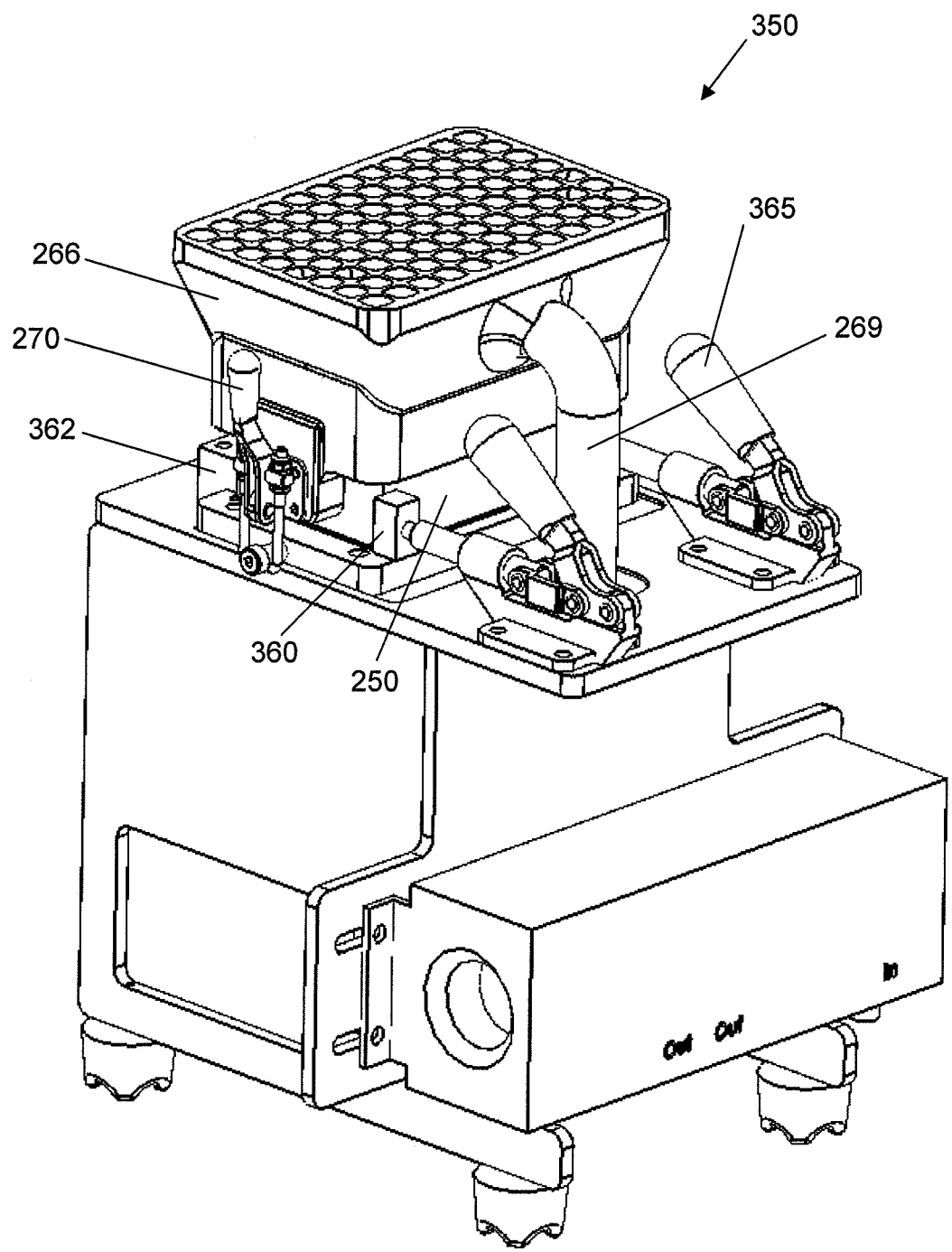
Figure 33:
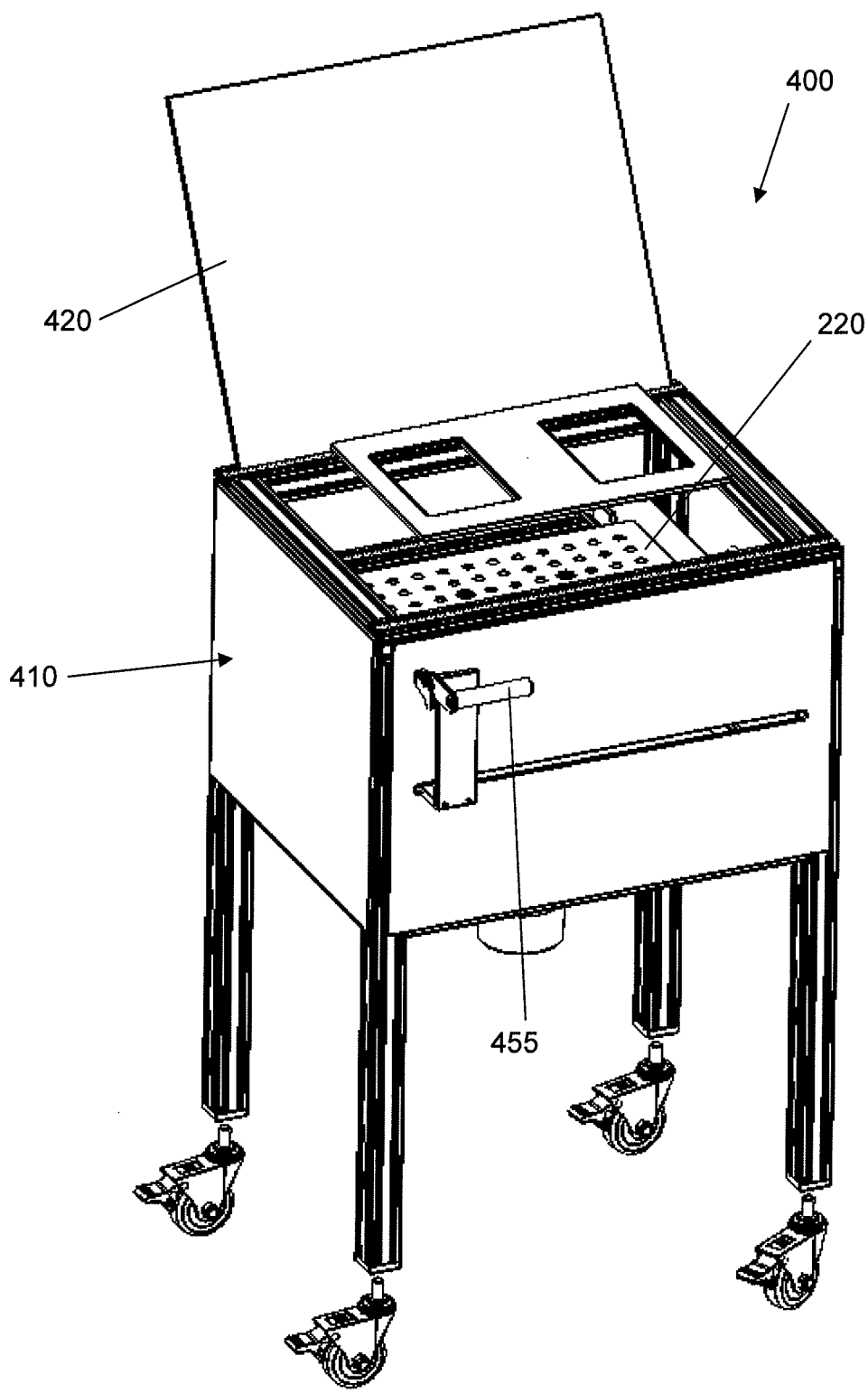
Figure 34:
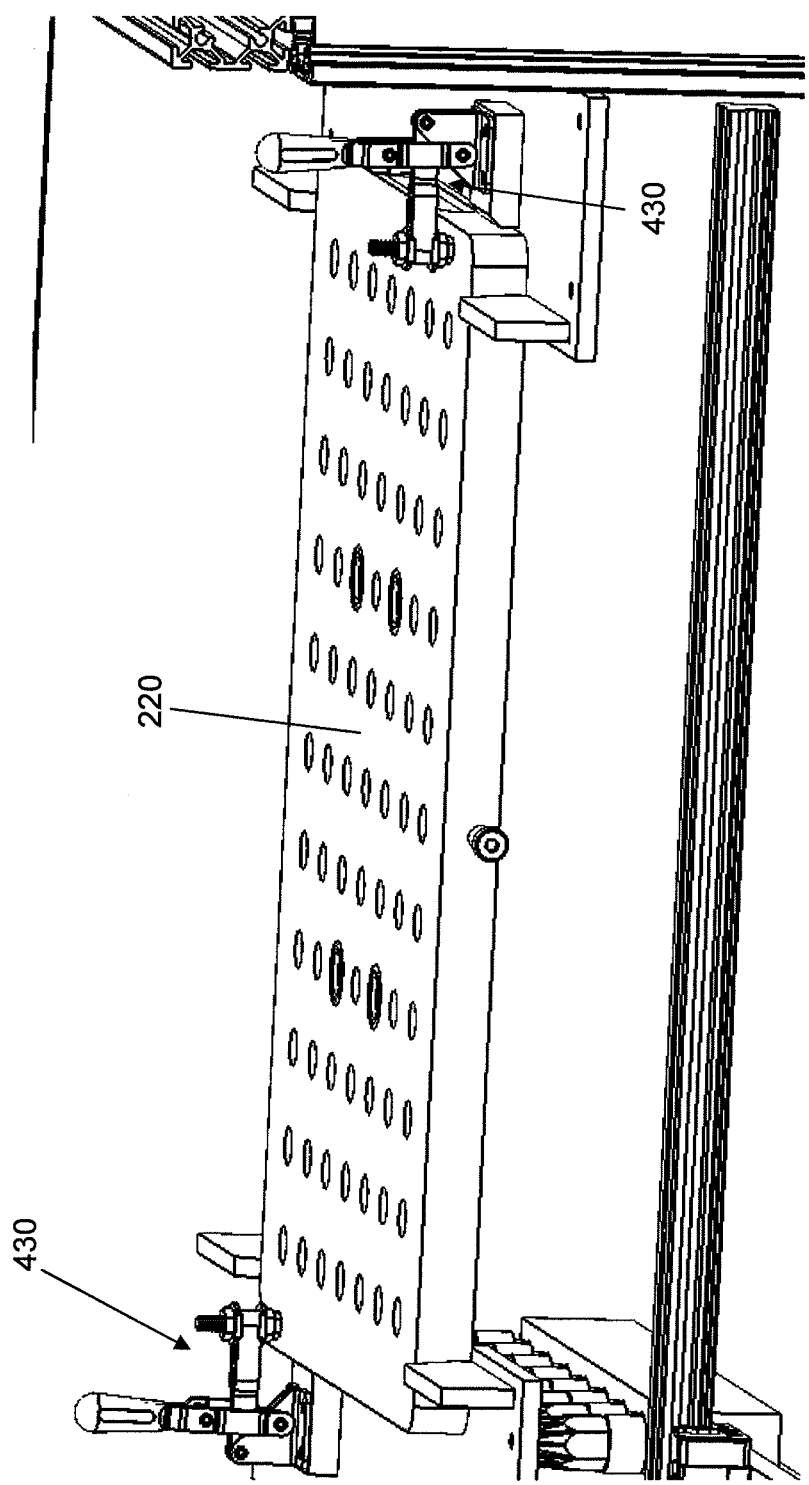
Figure 35:
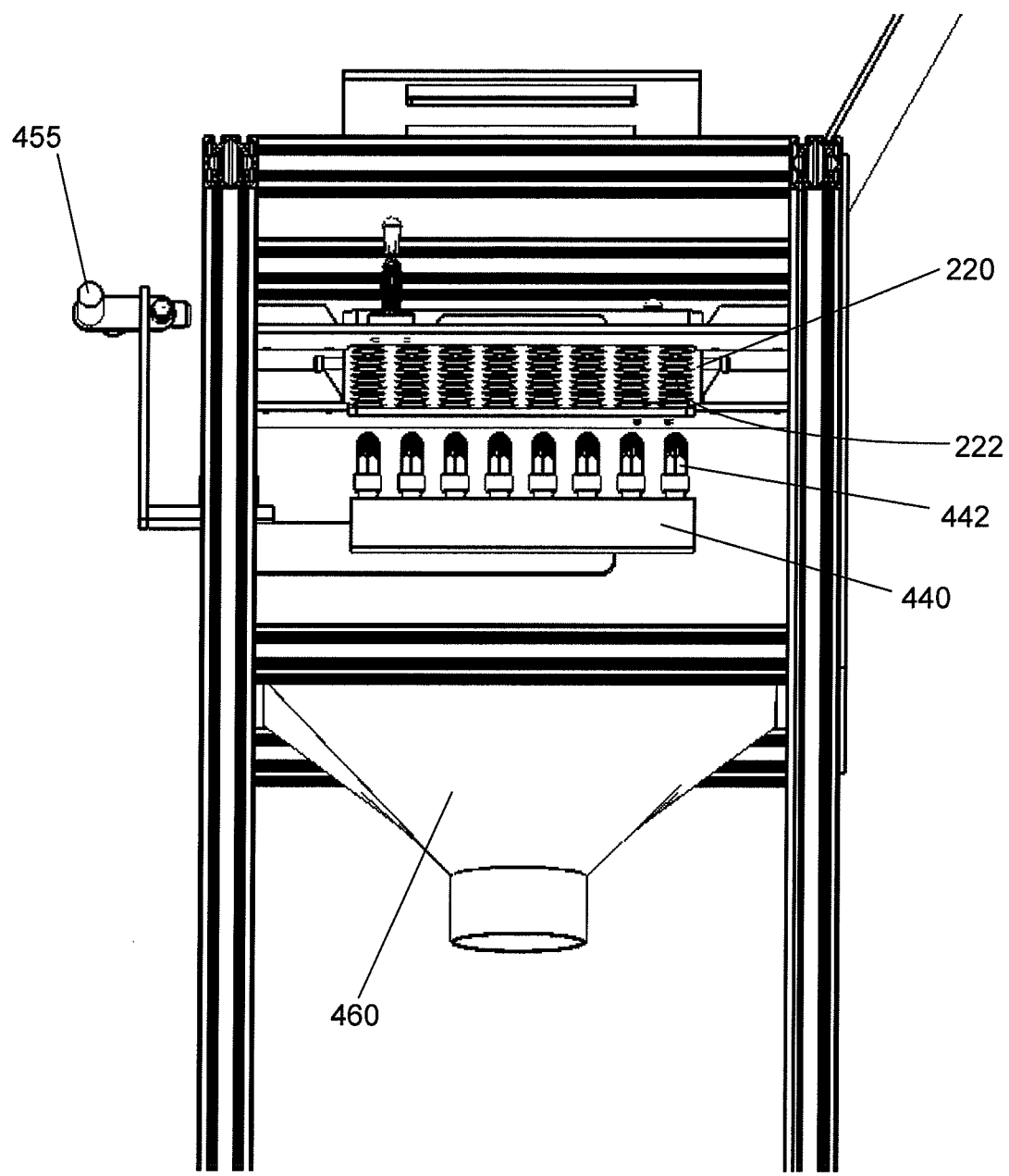
Figure 36:
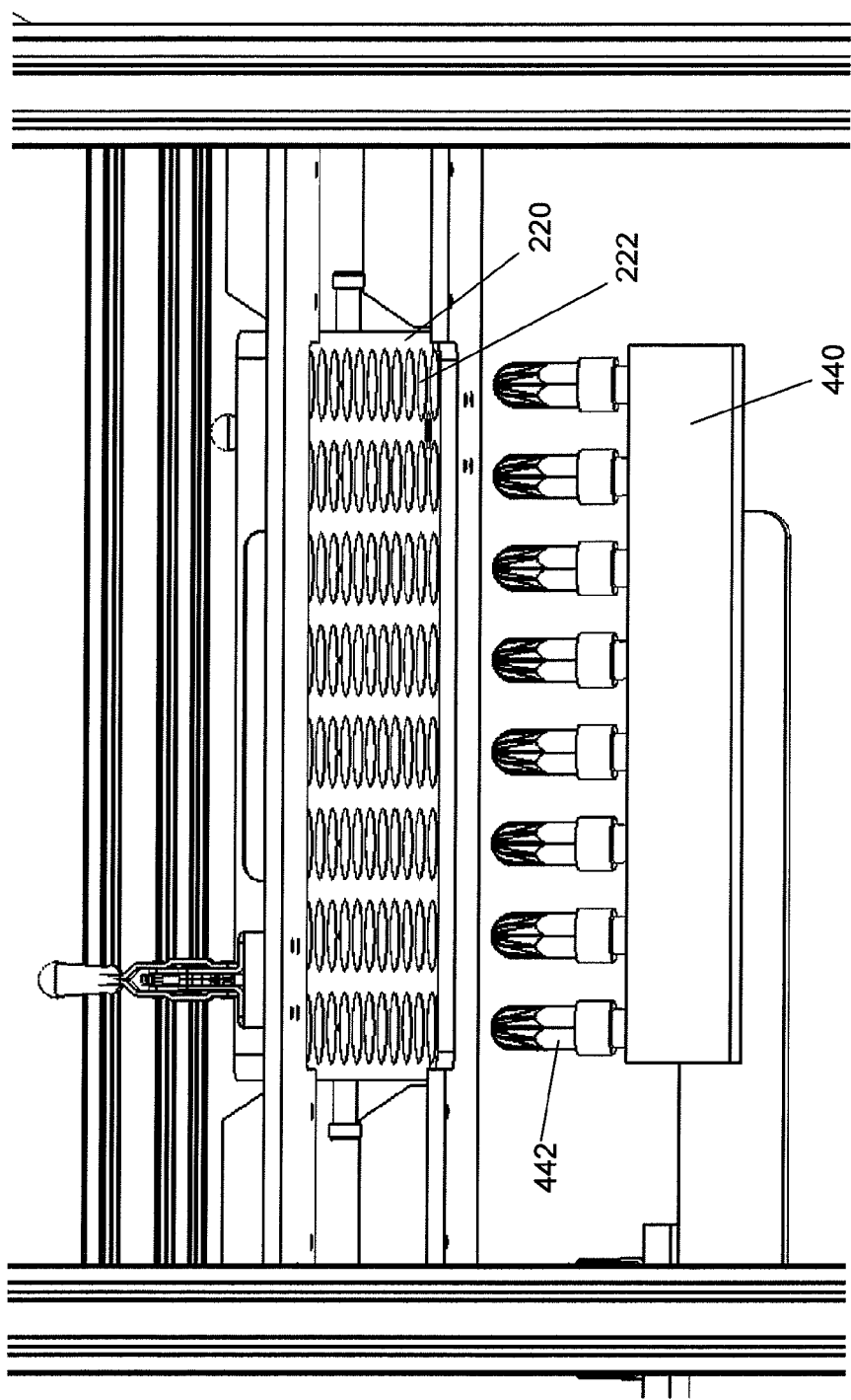
Figure 37:
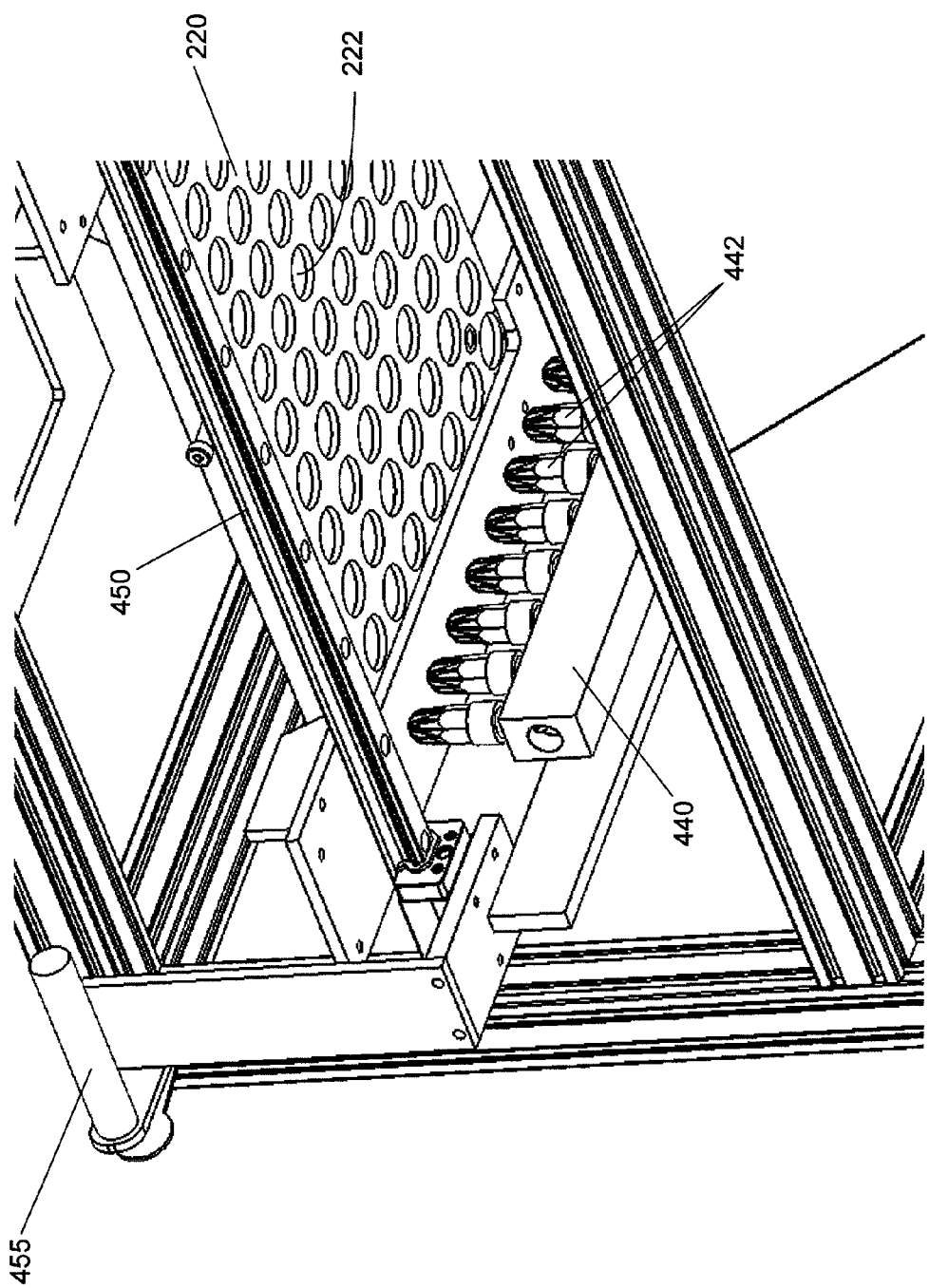
Figure 38:
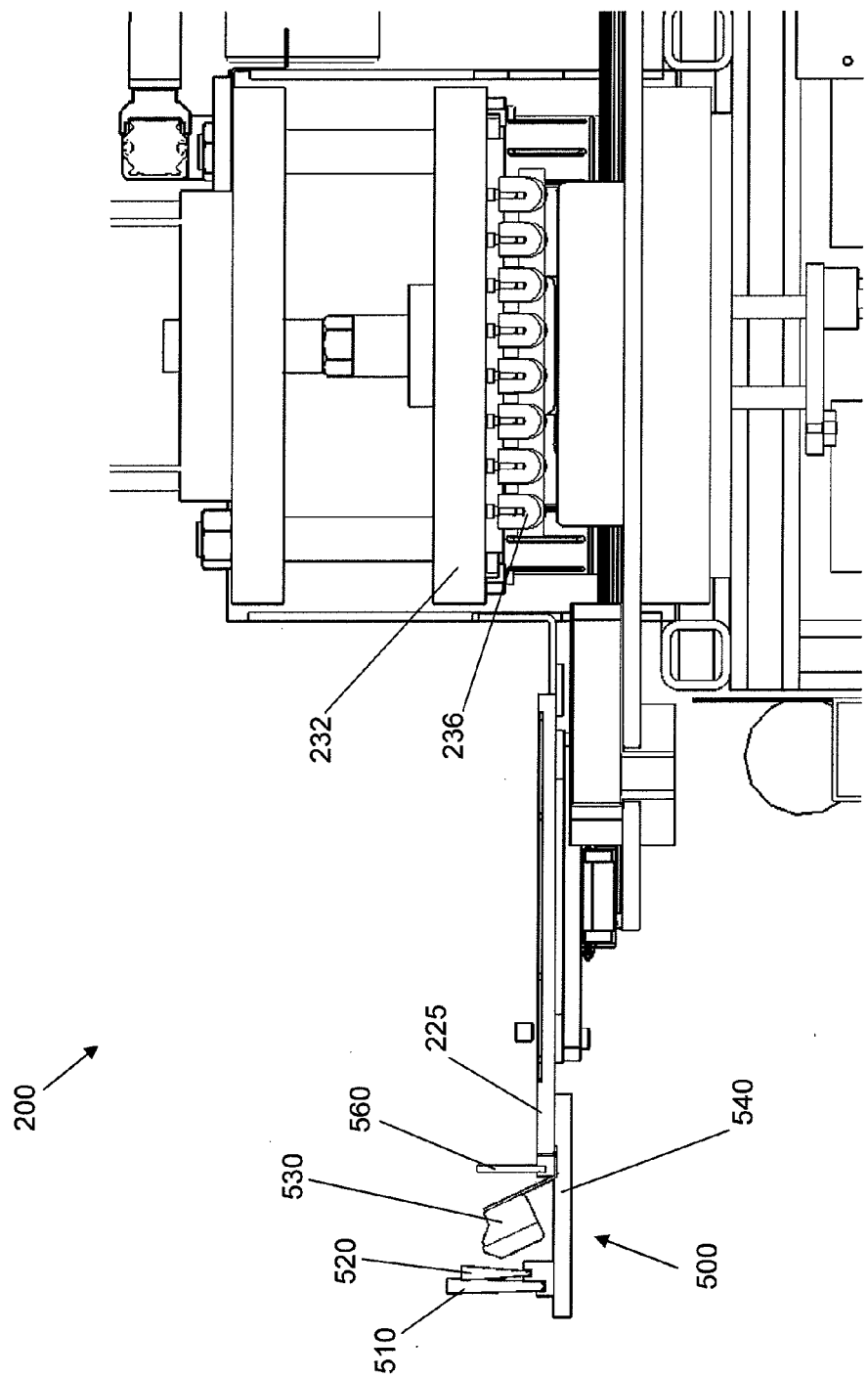
Figure 39:
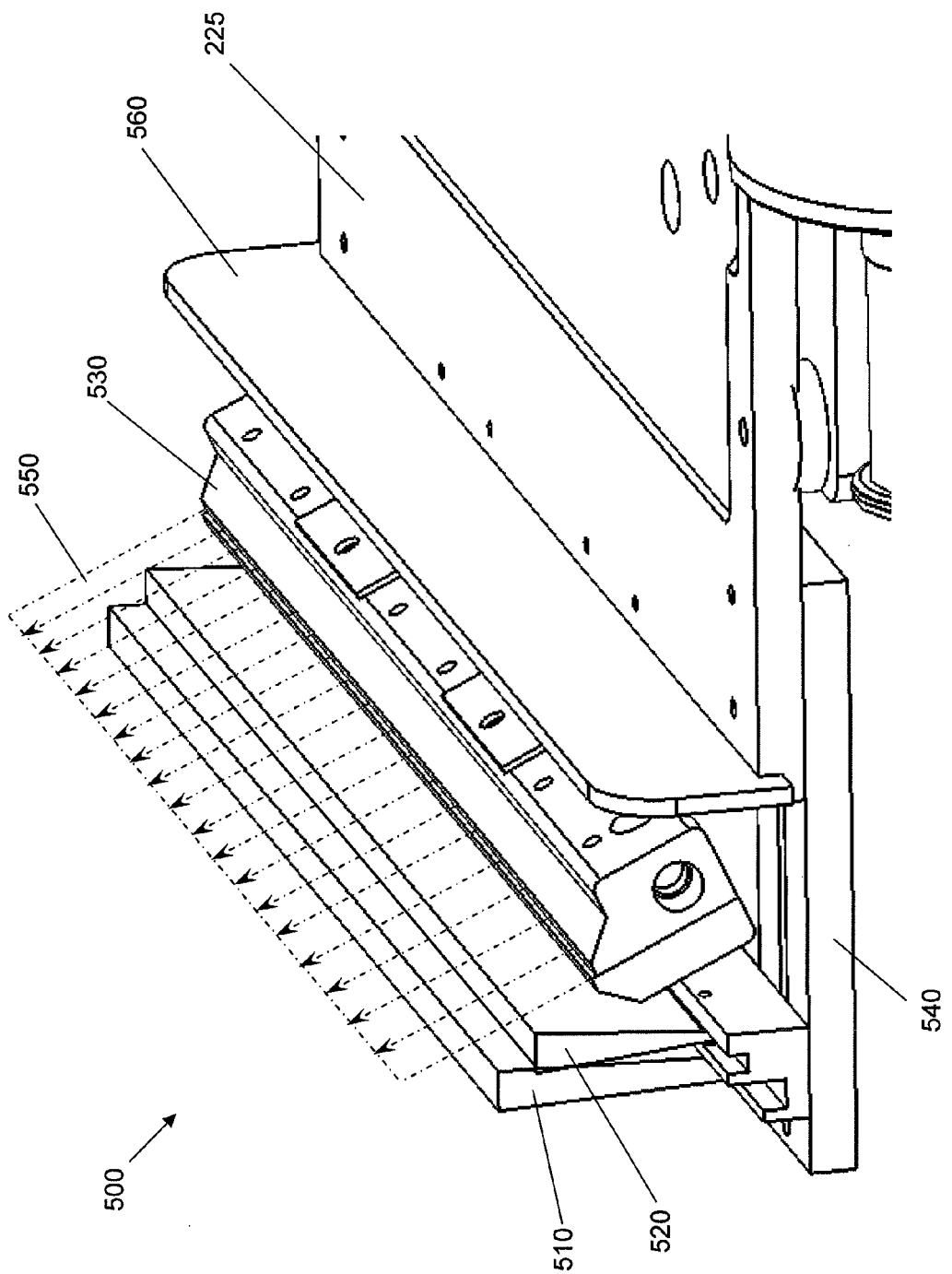
Figure 40:
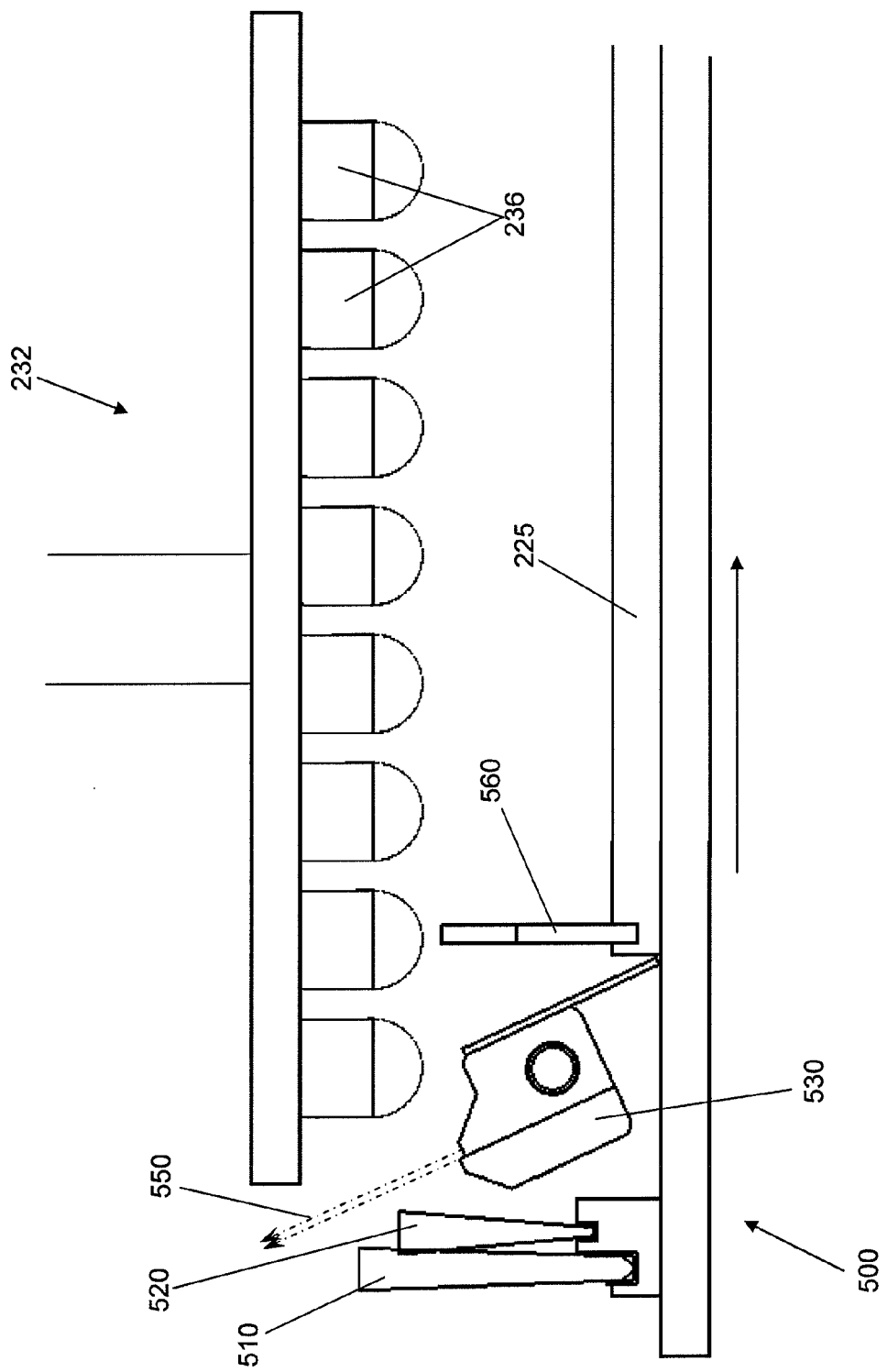
Figure 41:
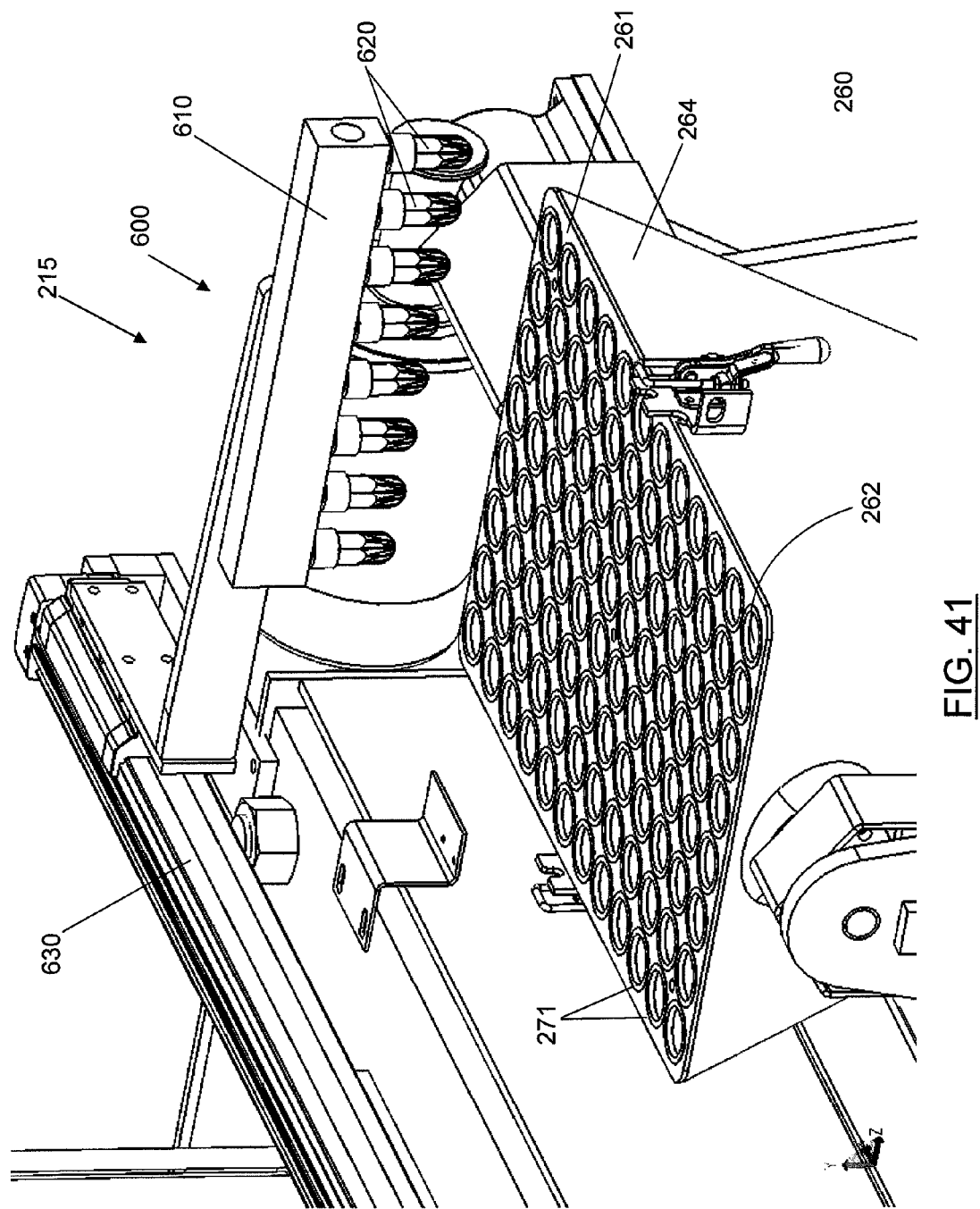

Having thus described the invention in general terms, reference will now be made to the accompanying drawings, which are not necessarily drawn to scale, and wherein:

FIG. 1 shows a perspective view of a system configured to execute a method of sampling one or more seeds in accordance with an exemplary embodiment of the present invention;

FIG. 2 shows an exploded perspective view of a system configured to execute a method of sampling one or more seeds in accordance with an exemplary embodiment of the present invention;

FIG. 3 shows a perspective view of a seed container in accordance with an exemplary embodiment of the present invention;

FIG. 4 shows a perspective view of a first layer of a seed container in accordance with an exemplary embodiment of the present invention;

FIG. 5 shows a perspective view of a force applying member in accordance with an exemplary embodiment of the present invention;

FIG. 6 shows a perspective view of a seed particle collector in accordance with an exemplary embodiment of the present invention;

FIG. 7 shows a seed particle directing member in accordance with an exemplary embodiment of the present invention;

FIG. 8 shows a front view of a system configured to execute a method of sampling one or more seeds in accordance with an exemplary embodiment of the present invention;

FIG. 9 shows a cross-section view showing a system configured to execute a method of sampling one or more seeds in accordance with an exemplary embodiment of the present invention;

FIG. 10 shows a perspective view of a system configured to execute a method of sampling one or more seeds in accordance with another exemplary embodiment of the present invention;

FIG. 11 shows a perspective view of a seed container in accordance with another exemplary embodiment of the present invention;

FIG. 12 shows a perspective view of a force applying member in accordance with another exemplary embodiment of the present invention;

FIG. 13 shows a perspective view of a system configured to execute a method of sampling one or more seeds in accordance with another exemplary embodiment of the present invention;

FIG. 14A shows a perspective view of a seed container in accordance with an exemplary embodiment of the present invention;

FIG. 14B shows a cross-section view of the seed container of FIG. 14A;

FIG. 15 shows a perspective view of a receiving station without the seed container installed in accordance with an exemplary embodiment of the present invention;

FIG. 16 shows a perspective view of the receiving station of FIG. 15 with the seed container installed;

FIG. 17 shows a perspective view of a seed breaking station in accordance with an exemplary embodiment of the present invention;

FIG. 18 shows a perspective view of a force applying mechanism in accordance with an exemplary embodiment of the present invention;

FIG. 19 shows a perspective view of a force applying member in accordance with an exemplary embodiment of the present invention;

FIG. 20 shows a plan view of a vibratory mechanism in accordance with an exemplary embodiment of the present invention;

FIG. 21 shows a perspective view of a seed collecting station in accordance with an exemplary embodiment of the present invention;

FIG. 22 shows a perspective cross-section view of a seed particle directing member in accordance with an exemplary embodiment of the present invention;

FIG. 23 shows a perspective view of a seed particle directing member with a secured seed particle collector in accordance with an exemplary embodiment of the present invention;

FIG. 24 shows a perspective view of a seed collecting station after rotation of the seed particle directing member in accordance with an exemplary embodiment of the present invention;

FIG. 25 shows an exploded perspective view of the seed particle directing member and seed particle collector in accordance with an exemplary embodiment of the present invention;

FIG. 26 shows a perspective view of a seed particle collector in accordance with an exemplary embodiment of the present invention;

FIG. 27A shows a perspective view of a seed particle collector installed on a collector tray in accordance with an exemplary embodiment of the present invention;

FIG. 27B shows a perspective cross-section view of the seed particle collector and collector tray of FIG. 27A;

FIG. 28 shows a perspective view of a second directing member and a seed particle collector in accordance with an exemplary embodiment of the present invention;

FIG. 29 shows a perspective view of a second directing member cleaning station in accordance with an exemplary embodiment of the present invention;

FIG. 30A shows a perspective view of a passageway cleaning mechanism in accordance with an exemplary embodiment of the present invention;

FIG. 30B shows a detail perspective view of the passageway cleaning mechanism of FIG. 30A;

FIG. 31 shows a perspective view of a seed particle collector removal station in accordance with an exemplary embodiment of the present invention;

FIG. 32 shows a perspective view of the seed particle collector removal station of FIG. 31 with the seed particle collector installed;

FIG. 33 shows a perspective view of a container cleaning station in accordance with an exemplary embodiment of the present invention;

FIG. 34 shows a perspective view of a seed container installed in a container cleaning station in accordance with an exemplary embodiment of the present invention;

FIG. 35 shows a plan view of a container cleaning station in accordance with an exemplary embodiment of the present invention;

FIG. 36 shows a perspective view of a container cleaning station in accordance with an exemplary embodiment of the present invention;

FIG. 37 shows a perspective view of a container cleaning station in accordance with an exemplary embodiment of the present invention;

FIG. 38 shows a plan view of a protrusion cleaning station in accordance with an exemplary embodiment of the present invention;

FIG. 39 shows a perspective view of a protrusion cleaning station in accordance with an exemplary embodiment of the present invention;

FIG. 40 shows a plan view of a protrusion cleaning station approaching alignment with protrusions of a force applying member in accordance with an exemplary embodiment of the present invention; and FIG. 41 shows a perspective view of a directing member cleaning mechanism in accordance with an exemplary embodiment of the present invention.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

As will be described below, the present invention is generally directed to a system and method for preparing samples of one or more seeds or representative seed portions for analysis. In various embodiments, the system and method include a force applying member, a seed container, and seed particle collector. The seed container includes at least one compartment containing a seed or representative seed portion (hereinafter referred to as a "seed" for brevity), and the force applying member is configured to apply a force to the compartment so as to break the seed into a plurality of seed particles, which are collected in the seed particle collector. As a result, embodiments of the present invention improve on the prior art by greatly reducing, and in some cases eliminating, the manual processes typically involved in generating tissue samples from seeds. Additionally, embodiments of the present invention are scaleable, and in some cases can be configured to generate samples from many seeds in a short period of time. Embodiments of the present invention also minimize the risk of contamination and cross-contamination of the seed particles.

FIGS. 1-9 depict a first embodiment of a system for sampling seeds; FIGS. 10-12 depict a second embodiment of a system for sampling seeds; and FIGS. 13-41 depict a third embodiment of a system for sampling seeds. Each embodiment is explained with reference to the figures below.

FIG. 1 shows a system 100 configured to execute a method of sampling one or more seeds in accordance with one exemplary embodiment of the present invention. FIG. 2 shows an exploded view of the system 100. In general, the system 100 includes a force applying member 102, a seed container 104, a lower plate 105, a seed particle directing member 106, and a seed particle collector 108. In the depicted embodiment, the seed container 104 includes a plurality of isolated seed compartments 110, with each compartment containing a single seed 111 to be sampled (seeds 111 not visible in FIG. 1 or FIG. 2). As a preliminary matter, it should be noted that although the appended figures and current description show and describe a system and method for sampling a plurality of seeds, embodiments of the present invention contemplate systems and methods for sampling as few as one seed, and thus in some embodiments the seed container may comprise a single compartment that contains a single seed. Additionally, in some embodiments it may be desired to include more than one seed per compartment, and thus the present invention contemplates these embodiments as well. As a result, the present invention should not be limited by the depictions and descriptions of the exemplary embodiment showing a seed container having a plurality of compartments each containing a single seed.

FIG. 3 depicts a perspective view of a seed container 104 in accordance with one exemplary embodiment of the present invention. Although in various embodiments a seed container may be constructed in a variety of ways, in the depicted embodiment the seed container 104 comprises a first layer 112 and a backing portion 114. It should be noted that the thickness of the first layer 112 and the backing portion 114 in FIG. 3 have been exaggerated for illustration purposes. The first layer 112 defines a top surface 115 and a bottom surface 117 and includes a plurality of individual cavities 116. FIG. 4 depicts a perspective view of seed container 104 shown from a reverse angle wherein the backing portion 114 and the plurality of seeds 111 have been removed to expose the plurality of cavities 116 formed by the first layer 112. In the depicted embodiment, the plurality of individual cavities 116 are areas of the first layer 112 that extend away from the top surface 115 to create a plurality of pockets having open ends 118. In the depicted embodiment, the plurality of cavities 116 have a truncated cone-like shape; however, in other embodiments the cavities could have any shape configured to isolate one or more seeds, including, but not limited to, various shapes typically used in "blister pack" applications, as well as other shapes, including domed oval and semi-spherical shapes, as well as circular, squared, oval, or rectangular wells.

In various embodiments, the first layer 112 of the seed container 104 may be made of a rigid, semi-rigid, or non-rigid material, which, in some embodiments, may be at least partially transparent. For example, various plastics may be suitable materials for the first layer 112, such as thermoplastics, including but not limited to, acrylonitrile butadiene styrene (ABS), acrylic, polyvinyl chloride(s) (PVC) with or without plasticizers such as phthalates, polyethylene, and polystyrene as well as many commercially available and possibly trademarked materials for purchase from Professional Plastics, 1810 E. Valencia Drive, Fullerton, Calif., 92831. In the depicted embodiment, the first layer 112 is made of a semi-rigid transparent thermoplastic PVC material.

Referring back to FIG. 3, in the depicted embodiment the backing portion 114 of seed container 104 is configured to be affixed to the bottom surface 117 of the first layer 112 so as to cover the open ends 118 of the cavities 116 formed by the first layer 112. As such, a plurality of isolated compartments 110 may be created. The degree of closure may vary depending on the requirements of the application. In some embodiments, the backing portion 114 could close off each cavity 116 such that seeds 111 contained in each compartment 110 are partially confined, or, as in the depicted embodiment, fully confined such that one or more of a range of contaminants are closed off from ingressing one or more of the cavities 116. Contaminants could include, air, water, light, radiation, insects, fungus, protozoa, monera, gasses, viruses, elements, compounds, or any other contaminant deemed to affect accurate testing of the contents of the compartments 110. Additionally, by fully confining each seed, the backing portion 114 may help to prevent cross-contamination (such as sample particles from other seeds) from entering the compartment 110. It should be noted that in other embodiments, the seed container 104 need not include a backing portion. For example, in some embodiments an isolated compartment may be defined by a single layer of the seed container, or the seed container itself may be the isolated compartment. An example of an embodiment wherein the seed container does not include a backing portion will be discussed in more detail below with regard to the embodiments shown in FIGS. 10-12 and 13-41.

In various embodiments, the backing portion 114 of the seed container 104 may be made out of various materials, including but not limited to, plastic materials, foil materials, paper(s), non-woven fibers, bio-plastics, and/or starch and starch-based materials. In the depicted embodiment, the backing portion 114 is made of a ruptureable foil material such that upon application of force, the backing portion 114 may be ruptured to release the contents of the compartment 110. In various embodiments, the backing portion 114 may optionally include or have applied to it one or more additional layers of the same or different type of material, and thus in various embodiments the backing portion 114 may comprise a combination of layers. The choice of material(s) for the backing portion 114 may depend on various factors, including, but not limited to, a desired number of seed particles and/or a desired sample particle size, as will be described below.

In some embodiments, the first layer 112 may include an adhesive, such as a heat activated adhesive, on portions of one or more of its surfaces to facilitate attachment of the backing portion 114. Likewise the backing portion 114 may include an adhesive, such as a heat activated adhesive, on portions of one or more of its layers to facilitate attachment thereof. In other embodiments, one or both of the heat activated adhesives may be replaced with non-heat activated adhesives or other binding agents or materials such as clips, pins, staples, rivets, brads, tape, cellophane, shrink wraps, wax, or other materials or combinations thereof. The seed container 104 may also have physical characteristics which may aid in identifying portions and/or the desired orientation of the first layer 112. For example, the first layer 112 may include one or more beveled corners 122, which may identify a specific corner of the seed container 104 for orientation purposes. Although the seed container 104 is shown with beveled or notched corners, it should be appreciated that in other embodiments one or more, or all, of the corners may not include notches or bevels.

In the depicted embodiment, the plurality of compartments 110 of the seed container 104 form an ordered array of compartments 110 having a particular pattern. The seed container 104 of depicted embodiment includes ninety-six compartments 110 arranged in an eight-by-twelve array. In various embodiments, the ordered array of compartments 110 may be selected and arranged for a variety of reasons which could prove advantageous, including facilitating more efficient and accurate identification of the seeds 111 in each individual compartment 110. As such, the seed container 104 may also have various indicia 124 displayed on one or more of its surfaces for a variety of purposes, including, identifying individual compartments, rows, columns, or specific portions of the seed container 104. In various embodiments, the indicia 124 may be included as a label and/or may be printed, embossed, or stamped onto any surface of one or more of the first layer 112 or the backing portion 114.

In the depicted embodiment, the seed container 104 includes indicia 124 identifying the rows and columns of the compartments 110. As shown in the figure, the row and column indicia 124 are represented by alphanumeric characters "A" "B" "C" . . . "H" for the rows and "1" "2" "3" . . . "12" for the columns. In other embodiments, the indicia may be represented by any indicia, including, but not limited to, any one or combinations of colors, text, figures, symbols, and the like. Additionally, in some embodiments the seed container 104 may also include various machine readable identifiers configured to provide information associated with the seed container, the compartments, seeds located within the compartments, etc. Such machine-readable identifiers may include, for example, various barcode identifiers and/or radio frequency identification (RFID) identifiers. Although the depicted embodiment shows indicia 124, it should be noted that in some embodiments there need not be any indicia. Additionally, in other embodiments there need not be any machine-readable identifiers.

In the depicted embodiment, each compartment 110 (and thus each seed 111) is assigned an address identified by the indicia associated with that compartment 110. For example, the seed 111 located in the upper right corner of the seed container 104 depicted in FIG. 3 is assigned the address of 'A1' and the seed 111 located in the bottom left corner of FIG. 3 is assigned the address of 'H12', etc. It should be noted that although the plurality of compartments 110 in the seed container 104 are shown in a row/column configuration, other configurations are contemplated by the present invention, including, but not limited to, circular and/or spiral arrangements of the compartments 110. The plurality of compartments 110 could also be positioned in staggered rows and/or columns (e.g., similar to a honeycomb configuration). Additionally, other embodiments of the present invention may include any number of compartments, including as few as one compartment or as many as thousands, or more, of compartments.

FIG. 5 shows a force applying member 102 in accordance with one exemplary embodiment of the present invention. In the depicted embodiment, the force applying member 102 includes a base plate 113 and a plurality of protrusions 121 extending from the base plate 113. Although in various other embodiments a force applying member may have any design configured to apply force in order to break one or more seeds, in the depicted embodiment the force applying member 102 is configured so as to apply a force at a plurality of locations on the seed container 104 corresponding to the isolated compartments 110. As described below, each protrusion 121 of the plurality of protrusions 121 of the force applying member 102 is configured to be pressed into contact with a respective compartment 110 of the plurality of isolated compartments 110 of the seed container 104 and thus, in the depicted embodiment, the plurality of protrusions 121 are configured in an array similar to the array of the plurality of compartments 110 of the seed container 104. In the depicted embodiment, the plurality of protrusions 121 are tapered cylinders configured to contact the plurality of compartments 110 of the seed container 104 substantially simultaneously, however in other embodiments the protrusions 121 could have any shape configured to break the seeds of the seed container 104 substantially simultaneously.

Additionally, it should be noted that in other embodiments of the present invention, other configurations of a force-applying member are possible. For example, although the force applying member 102 of the depicted embodiment is configured to apply force to each of the plurality of compartments 110 of the seed container 104 substantially simultaneously, in other embodiments a force applying member may be configured to apply force to one or more of the compartments non-simultaneously, such as, for example, by applying force to one compartment at a time. However, by configuring the force applying member 102 to apply force to the plurality of compartments 110 of the seed container 104 as in the depicted embodiment, a large number of seeds may be sampled in a relatively small amount of time and throughput levels may be maintained for efficiency purposes. In various embodiments, the force applying member 102 may be constructed of any one or any combination of materials configured to apply a force to the seed compartments 110 so as to break the seeds 111 into groups of two or more seed particles, including, but not limited to, various metal materials such as steel or aluminum, or other materials such as plastic or wood composite materials.

As noted above, the seed container 104 of the depicted embodiment includes indicia 124 identifying the isolated seed compartments 110. In various embodiments, the indicia 124 of the seed container 104 may be designed such that it correlates with indicia of other containers. For example, other lab equipment including containers, lab plates, testing trays or others may be used to facilitate easier and more efficient and accurate linking of information to the seeds 111 contained within the individual compartments 110 of the seed container 104. FIG. 6 depicts a seed particle collector 108 in accordance with one exemplary embodiment of the present invention. In the depicted embodiment, the seed particle collector 108 comprises a top plate 128 and a bottom plate 130. The top plate 128 includes a plurality of apertures 132 that creates a plurality of respective channels 134 (more clearly visible in cross-section view shown in FIG. 9) that align with a plurality of seed particle collection cavities 136 (also visible in cross-section view shown in FIG. 9) of the bottom plate 130. In the depicted embodiment there are ninety-six apertures 132 that create ninety-six channels 134 configured in an eight by twelve array. In various embodiments, indicia 138 may be displayed on the top plate 128 and/or bottom plate 130 of the seed particle collector 108. In the depicted embodiment, the seed particle collector 108 is constructed of a plastic material, such as ABS, and the bottom plate 130 is constructed of a polypropylene plastic material, however in various other embodiments the seed particle collector 108 or the bottom plate 130 may be constructed of other materials, including, but not limited to, metal materials such as steel or aluminum, or other materials, such as plastic or wood composite materials.

In the depicted embodiment, the apertures 132 of the seed particle collector 108 are arranged in an array that mimics the array of the compartments 110 of the seed container 104. However, in other embodiments, the apertures 132 of the seed particle collector 108 may be arranged in any configuration and need not mimic any arrangement of the seed container 104. Additionally, in other embodiments the seed particle collector 108 need not include the same number of apertures 132 or collection cavities 136 as the seed container 104, and may include more or less apertures 132 or collection cavities 136 as compartments 110 of the seed container 104. Such embodiments may be useful in applications where individual samples from seeds are desired to be split up into several collection cavities, or where samples of multiple seeds are desired to be combined into various collection cavities. However, by arranging the apertures 132 of the seed particle collector 108 in a similar manner as the compartments 110 of the seed container 104 as in the depicted embodiment, seed samples from each individual seed 111 may be gathered in corresponding individual locations of the seed particle collector 108 and data relating to samples from each seed 111 may be easily tracked.

In the depicted embodiment, the positionally-addressable ordered array of indicia 124 of the seed container 104 correlates with a positionally-addressable ordered array of indicia 126 located on the top plate 128 of the seed particle collector 108. Specifically, in the depicted embodiment, the top plate 128 and the bottom plate 130 of the seed particle collector 108 includes indicia 126 identifying the rows and columns of the apertures 132. As shown in the figure, the row and column indicia 126 are represented by alphanumeric characters "A" "B" "C" . . . "H" for the rows and "1" "2" "3" . . . "12" for the columns. In other embodiments, the indicia may be represented by any indicia, including, but not limited to, any one or combinations of colors, text, figures, symbols, and the like. Additionally, in some embodiments the seed particle collector 108 may also include various machine readable identifiers configured to provide information associated with the seed container, the compartments, seeds located in the compartments, etc. Such machine-readable identifiers may include, for example, various barcode identifiers and/or radio frequency identification (RFID) identifiers. However, it should be noted that in some embodiments there need not be any indicia or any machine-readable identifiers.

In the depicted embodiment, the sample of seed particles resulting from the seed 111 located in the 'A1' position of the seed container is assigned an address 'A1' identified by the indicia associated with the collection cavity 136 that receives the seed particles from the "A1" seed 111. Thus, each seed 111 from the seed container 104 may be tracked in a 1:1 relationship with the respective samples collected in the seed particle collector 108. In various embodiments, the indicia 126 may be included as a label and/or printed, embossed, stamped onto the seed particle collector 108. It should be noted that in other embodiments, neither the top plate 128 nor the bottom plate 130 of the seed particle container need include indicia 126. However, by including such indicia 126 in various embodiments the ability to track information about each individual seed 111 contained in the seed container and the samples collected in the collection cavities 136 may be facilitated.

FIG. 7 shows a perspective view of the lower plate 105 and the seed particle directing member 106 in accordance with one embodiment of the present invention. As shown in the figure, the seed particle directing member 106 includes a main body 140 that defines a top surface 142. A plurality of apertures 144 are defined in the top surface 142 that create a plurality of channels 146 extending through the main body 140. The plurality of apertures 144 are configured to line up with the open ends 118 of the plurality of cavities 116 of the compartments 110 of the seed container 104. As such, the channels 146 leading from the apertures 144 are configured to create a plurality of isolated passageways that extend through the seed particle directing member 106. Thus, seed particles may travel from each of the compartments 110 of the seed container 104 through the seed particle directing member 106 and to the seed particle collector 108. In the particular embodiment shown in FIG. 7, there are ninety-six apertures 144 that create ninety-six individual channels 146 configured in an eight by twelve array. These ninety-six channels 146 lead to the ninety-six channels 134 of the seed particle collector 108 and thus to the ninety-six individual collection cavities 136 of the seed particle collector 108. The lower plate 105 is configured to provide a surface that supports the seed container 104 when the force applying member 102 presses against the compartments 110 of the seed container 104 to break the seeds. In the depicted embodiment after breaking the seeds, the lower plate 105 is removed for a subsequent action by the force applying member 102 against the compartments 110 of the seed container 104 that directs the seed particles through the seed container 104. It should be noted that in some embodiments there need not be a seed particle directing member as samples from the seeds may travel from a seed container directly to a seed particle collector. Additionally, in some embodiments there need not be a lower plate 105.

In the depicted embodiment, the lower plate 105 is constructed of a steel material, such as tool steel, and the seed particle directing member 106 is constructed of a plastic material, such as ABS, however in various other embodiments either or both the lower plate 105 or the seed particle directing member 106 may be constructed of other materials, including, but not limited to, metal materials, such as steel or aluminum, or other materials, such as plastic or wood composite materials. Additionally, in various other embodiments, a vibratory action may be applied to one or more components of the system 100 such as, for example, one or both of the seed particle directing member 106 or the seed particle collector 108 in order to influence transfer of seed particles from the seed container 104 through the seed particle directing member 106 and seed particle collector 108 and into the bottom plate 130 (see e.g., FIG. 8). In various embodiments, the vibratory action may be applied via any of a variety of vibration generating apparatuses as are known in the art.

FIG. 8 shows a front view of a system 100 for sampling a plurality of seeds in accordance with an exemplary embodiment of the present invention. In the figure, the components of the system 100 are assembled to depict sampling of the plurality of seeds 111 contained in the seed container 104. In general, tissue samples of the individual seeds 111 contained in the seed container 104 are obtained by breaking the seeds 111 and pushing the resulting seed particles through the seed container 104 such that the seed particles are ultimately collected in the collection cavities 136 of the seed particle collector 108.

In operation, the plurality of protrusions 121 of the force applying member 102 are driven downward by a driving member 148 that moves the force applying member 102 such that the plurality of protrusions 121 press into contact with respective compartments 110 of the seed container 104. In the depicted embodiment, the driving member 148 is a pneumatic actuator configured to mechanically move the force applying member 102 with a quick plunging action. However, in other embodiments the driving member 148 may be any device configured to mechanically move the force applying member 102 into contact with the seed container 104, including, but not limited to, pneumatic actuators, hydraulic actuators, and electric actuators. In various embodiments, the driving member 148 may be fully or partially automated. Other methods of mechanically moving the force applying member 102 into contact with the seed container 104 are also possible, including having an operator manually move the force applying member 102 into contact with the seed container 104, such as by providing a lever system associated with the force applying member 102 in the manner of a manual press. Additionally, the mass of the force applying member 102 may act on the seed container 104 through gravity so as to apply a particular force to the seed container 104. Although in the depicted embodiment the force applying member 102 is shown as being driven downward in order to contact the seed container 104, in other embodiments the force applying member may follow other paths or combinations of paths configured to apply force to the compartments of the seed container.

FIG. 9 shows a cross-section view of a force applying member 102, a seed container 104, a seed particle directing member 106, and a seed particle collector 108 in accordance with one exemplary embodiment of the present invention. As shown in the figure, in the depicted embodiment, the seed container 104 is configured such that each isolated compartment 110 of the seed container 104 is positioned above a respective aperture 144 of the seed particle directing member 106. In order to generate and collect samples from the plurality of seeds contained in the seed container 104 using the system 100 depicted in FIG. 9, the protrusions 121 of the force applying member 102 are pressed into contact with respective compartments 110 of the seed container 104. Although shown in the figure as appearing to intersect the compartments 110 of the seed container 104, upon pressing the protrusions 121 of the force applying member 102 into the compartments 110 of the seed container 104, the protrusions 121 tend to collapse the compartments 110 of the seed container around the respective seeds, thus pushing the seeds against the backing portion 114 and the lower plate 105 (not shown) and breaking the seeds into respective groups of seed particles 150. The lower plate 105 is then removed, and the force applying member 102 is again pressed into contact with the seed container 104 such that the respective groups of seed particles 150 are pressed through the backing portion 114 and into respective channels 146 of the seed particle directing member 106. In such a manner, in some embodiments the stroke of subsequent actions of the force-applying member 102 may be longer than the initial action(s). In various embodiments the lower plate 105 may be removed manually or automatically after the force applying member 102 is pressed into the seed container 104 to break the seeds into respective groups of seed particles 150. It should be noted in other embodiments the seeds may be broken and directed through the seed container 104 in a single stroke of the force applying member 102.

As shown in the figure, each channel 146 of the seed particle directing member 106 provides an isolated passageway to a corresponding channel 134 of the seed particle collector 108. Likewise, each channel 134 of the seed particle collector 108 provides an isolated passageway to a corresponding collection cavity 136 of the seed particle collector 108. As a result, by actuating the force applying member 102 in the depicted embodiment, each seed 111 of the ninety-six seeds 111 contained in the seed container 104 is broken into a respective group of seed particles 150. Each respective group of seed particles 150 is then pressed out of its respective isolated compartment 110 and travels through isolated channels 146, 134 and to an isolated collection cavity 136 where the seed particles 150 are available for testing. Therefore, any risk of contamination of the seed samples by various contaminates or by cross-contamination of the seed samples from samples from other seeds is greatly reduced. It should be noted that in various other embodiments, contamination may also be reduced by purging the channels 146, 134 and removing cross-contamination materials from the seed particle directing member 106 and the seed particle collector 108. In various embodiments this may be accomplished, for example, by forcing a fluid medium, such as compressed air, through the seed particle directing member 106 and the seed particle collector 108.

FIG. 10 shows a system 100 configured to execute a method of sampling one or more seeds in accordance with another exemplary embodiment of the present invention. In general, the system 100 includes a force applying member 102 (having a plurality of protrusions 121) and a seed container 104. In the depicted embodiment, the seed container 104 includes a plurality of isolated seed compartments 110, with each compartment containing a single seed (not visible) to be sampled. As noted above, although the appended figures and current description show and describe a system and method wherein each seed compartment includes a single seed per compartment, the present invention contemplates other embodiments that include more than one seed per compartment. In the depicted embodiment, the force applying member 102 is controlled via a driving member 148 such as one described above that moves the force applying member 102 such that the protrusions 121 are received into respective compartments 110 of the seed container 104.

In the depicted embodiment, the seed container 104 is supported by a lower plate (not shown) that is configured to support each of the respective compartments 110 of the seed container 104. In such a manner, the seed container 104 of this embodiment has an opposite orientation as the embodiment described above with respect to FIGS. 1-9 such that when driven by the driving member 148, the protrusions 121 of the force applying member 102 are received into respective compartments 110 of the seed container 104 such that the protrusions directly contact the seeds in order to break the seeds, rather than contacting and collapsing the respective compartments 110 in order to break the seeds. In the depicted embodiment, the driving member 148 is a pneumatic actuator configured to move the force applying member 102 downward with a series of quick plunging actions. However in other embodiments, the driving member 148 may move the force applying member 102 into contact with the seeds with one plunging action. In various embodiments, the driving member 148 may be fully or partially automated. Other methods of moving the force applying member 102 into contact with the seeds are also possible, including having an operator manually move the force applying member 102 into contact with the seeds, such as by providing a lever system associated with the force applying member 102 in the manner of a manual press. Additionally, the mass of the force applying member 102 may act on the seeds through gravity so as to apply a particular force to the seed container 104.

FIG. 11 depicts a perspective view of a seed container 104 in accordance with the embodiment of the present invention shown in FIG. 10. Unlike the embodiment described above, the seed compartments of this embodiment do not include a backing portion. Although in various embodiments a seed container may be constructed in a variety of ways, in the depicted embodiment the seed container 104 comprises a single layer 112. The single layer 112 defines a top surface 115 and a bottom surface 117 and includes a plurality of individual cavities 116 that define the plurality of isolated seed compartments 110. In the depicted embodiment, the plurality of individual cavities 116 are areas of the first layer 112 that extend away from the top surface 115 to create a plurality of pockets having open ends 118. In the depicted embodiment, each cavity 116 also includes a peripheral lip 119 that extends above the top surface 115 around the opening 118. In various embodiments, a peripheral lip 119 may be included to aid in containing seed particles in the seed compartments 110 during the seed breaking process, however not every embodiment need include a peripheral lip. In the depicted embodiment, the plurality cavities 116 have a semi-spherical shape that is configured to roughly match the shape of the protrusions 121 of the force applying member 102; however, in other embodiments the cavities could have any shape configured to isolate one or more seeds and to receive the protrusions 121 of the force applying member 102.

In various embodiments, the seed container 104 may be made of a rigid, semi-rigid, or non-rigid material. For example, various plastics may be suitable materials for the seed container 104, such as thermoplastics, including but not limited to, acrylonitrile butadiene styrene (ABS), acrylic, polyvinyl chloride(s) (PVC) with or without plasticizers such as phthalates, polyethylene, polystyrene as well as many commercially available and possibly trademarked materials for purchase from Professional Plastics, 1810 E. Valencia Drive, Fullerton, Calif., 92831. In the depicted embodiment, the seed container 104 is made of a semi-rigid thermoplastic high impact polystyrene material.

In the depicted embodiment, the plurality of compartments 110 of the seed container 104 form an ordered array of compartments 110 having a particular pattern. The seed container 104 of depicted embodiment includes twelve compartments 110 arranged in a three by four array. In various embodiments, the ordered array of compartments 110 may be selected and arranged for a variety of reasons which could prove advantageous, including facilitating more efficient and accurate identification of the seeds 111 in each individual compartment 110. As such, the seed container 104 may also have various indicia as described above displayed on one or more of its surfaces for a variety of purposes, including, identifying individual compartments, rows, columns, or specific portions of the seed container 104. In various embodiments, the indicia may be included as a label and/or printed, embossed, stamped onto any surface of the seed container 104.

FIG. 12 shows a force applying member 102 in accordance with the embodiment of the present invention shown in FIG. 10. In the depicted embodiment, the force applying member 102 includes a base plate 113 and a plurality of protrusions 121 extending from the base plate 113. Although in various other embodiments a force applying member may have any design configured to apply force to a seed located in a seed compartment of a seed container in order to break the seed into two or more seed particles, in the depicted embodiment the force applying member 102 is configured so as to apply a force at a plurality of locations corresponding to the plurality of isolated compartments 110. As described below, each protrusion 121 of the plurality of protrusions 121 of the force applying member 102 is configured to be received into the cavity 116 of a respective compartment 110 of the plurality of isolated compartments 110 of the seed container 104, and thus in the depicted embodiment the plurality of protrusions 121 are configured in an array similar to the array of the plurality of compartments 110 of the seed container 104. In the depicted embodiment, each of the protrusions 121 has a spherical end that is configured to approximately match the shape of the cavities 116 of the seed container 104. It should be noted however that in other embodiments of the present invention, other configurations of a force-applying member are possible. In the depicted embodiment, the force applying member 102 is constructed of a steel material, such as tool steel, however in various other embodiments, the force applying member 102 may be constructed of any one or any combination of materials configured to apply a force to the plurality of seeds so as to break one or more seeds into two or more seed particles, including, but not limited to, various metal materials such as steel, or other materials such as plastic or wood composite materials.

In the depicted embodiment, once the force applying member 102 breaks the seeds located in the plurality of compartments 110 into respective groups of two or more seed particles, the groups of particles may then be directed into a seed particle collector. In the depicted embodiment, the seed particles are manually transferred to the seed particle collector. For example, in one embodiment the respective seed particles may be scooped from each compartment 110 and transferred to a corresponding collection cavity of the seed particle collector. Alternatively, a seed particle collector having corresponding compartments may be placed on top of the seed container 104 and the seed container 104 and the seed particle collector may be inverted such that the seed particles from the seed compartments 110 are transferred into corresponding compartments of the seed particle collector.

FIG. 13 shows a system 200 configured to execute a method of sampling one or more seeds in accordance with yet another exemplary embodiment of the present invention. In general, the system 200 includes a receiving station 205, a seed breaking station 210, and a seed collecting station 215. Each station 205, 210, 215 is configured to perform certain operations on the seed or seeds to prepare the seeds for further processing and/or analysis. As described in greater detail below, seeds are received at the receiving station 205, the seeds are broken down into seed particles at the seed breaking station 210, and the seed particles are collected for further processing/analysis at the seed collecting station 215.

The receiving station 205 is configured to receive a seed container 220 having at least one isolated compartment 222, where each isolated compartment contains a single seed (not visible) to be sampled. As noted above, although the appended figures and associated description show and describe a system and method wherein each seed compartment includes a single seed per compartment, the present invention contemplates other embodiments that include more than one seed per compartment.

The seed container 220 may be configured as described above in connection with FIGS. 1-12. In other cases, the seed container 220 may be a seed tray that defines the plurality of isolated compartments 222, as shown in FIGS. 14A and 14B. As mentioned above, the seed container 220 may include any number, size, and shape of compartments. For example, as shown in FIGS. 14A and 14B, the seed container 220 may include ninety-six compartments 222 arranged in an eight-by-twelve array, and each compartment may have a spherical shape. In addition, the seed container 220 may also have various indicia displayed (not shown) on one or more of its surfaces for a variety of purposes, including, identifying individual compartments, rows, columns, or specific portions of the seed container 220, as described above.

The receiving station 205 may include a platform 225 that is configured to receive and hold the seed container 220. In some cases, as shown in FIG. 15, the platform 225 may define an indented region 227, notches, grooves, or other retaining features for holding the seed container 220 in place. Furthermore, the platform 225 may be movable, such that, with the seed container 220 in place (see FIG. 16), the platform can convey the seed container from the receiving station 205 to the seed breaking station 210.

The seed container 220 may be moved from one station to the next manually, for example by an operator overseeing the operation of the various stations. Preferably, however, the seeds are conveyed between stations automatically. For example, as shown in FIG. 13, the system 200 may include a seed container transport mechanism 700 that is configured to automatically move the seed container 220 from the receiving station 205 to the seed breaking station 210 and from the seed breaking station 215 to the seed collection station 215 upon completion of a respective operation of the receiving station, seed breaking station, and seed collection station. The transport mechanism 700 may, for example, convey the seed container 220 via the platform 225.

The transport mechanism 700 may include a system of tracks 710 along which the platform 225 is configured to ride, as well as an actuator 720 configured to move the platform along the tracks from one station to the next. In this regard, the transport mechanism 700 may also include sensors (not shown) or other components that detect when operations at each station are complete. Thus, when the sensors detect that operations at one station are complete, signals may be transmitted to the actuator 720, for example, to advance the platform 225 to the next station. Signals may also be sent to the station that has completed its operations with the command to cease operations, and other signals may be sent to the next station with the command to begin its operations. The sensors may, for example, detect one or more of the position of the seed container 220 in the system, the position of other components of the system 200, and/or the duration of certain operations, and the signals may be sent accordingly.

Furthermore, a control module 730 may be provided to allow the operator to start system operations (for example, once the seed container 220 has been properly received at the receiving station 205) and/or to stop operations at any given time (for example, if an emergency situation arises). The control module 730 may further allow the operator to configure various parameters of the system 200, such as the duration of certain system operations and/or the number of cycles to be performed at a particular station, as described below.

At the seed breaking station 210, shown in FIG. 17, the seed in each isolated compartment 222 of the seed container 220 may be broken into two or more seed particles. Thus, the seed breaking station 210 may include a force applying mechanism 230 (shown in FIG. 18) that is configured to move a force applying member 232 into contact with the seed located in each isolated compartment 222. In this way, the force applying member 232 may apply a force to the seed in the isolated compartment 222 to break the seed into two or more seed particles. In some cases, the force applying mechanism 230 is configured to move the force applying member 232 such that the force applying member applies a force to the seed in the isolated compartment 222 and then intermittently applies force to the resulting seed particles to encourage further breakage of the seed. As shown in FIG. 17, the force applying member 232 and part of the force applying mechanism 230 may be enclosed by panels 233 of plexiglass or a similar material, for example, to protect an operator of the system from the action of the force applying member 232 and/or to reduce the possibility of contaminants or environmental debris entering the seed breakage area.

As noted above in connection with the previously described embodiments, the force applying member 232 may have various configurations. In FIGS. 18 and 19, for example, the force applying member 232 includes a base plate 234 and a plurality of protrusions 236 extending from the base plate 234. Although in various other embodiments a force applying member may have any design configured to apply force in order to break one or more seeds, in the depicted embodiment the force applying member 232 is configured so as to apply a force at a plurality of locations on the seed container 220 corresponding to the isolated compartments 222.

Each protrusion 236 of the force applying member 232 may be configured to be pressed into contact with the seed located in a respective compartment 222 of the seed container 220 by the force applying mechanism 230. Thus, in the depicted embodiment, the plurality of protrusions 236 are configured in an array similar to the array of the plurality of compartments 222 of the seed container 220. In the depicted embodiment, for example, each protrusion 236 has a spherical contact area 238 that is configured to substantially match the shape of the respective compartment 222 of the seed container 220 (see FIGS. 14A and 14B). In this way, the engagement of the protrusion 236 with the compartment 222 may have a mortar-and-pestle effect, encouraging a more complete breakage of the seed into seed particles.

Referring to FIG. 20, in some cases, the seed breaking station further includes a vibratory mechanism 240 that is configured to intermittently apply a vibratory action to the seed container 220 to encourage further breakage of the seed into the seed particles. FIG. 20 depicts the seed breaking station 210 with various panels and components removed for ease of description. The vibratory mechanism 240 may, for example, include a pneumatic actuator 242 configured to move a number of platform support rods 244 through holes in the platform 225 and into engagement with the seed container 220. In this way, the seed container 220 may be raised up slightly from its initial position, and the vibratory mechanism 240 may be able to apply the vibratory action to the seed container 220 through corresponding movement of the support rods 244.

Through the vibration of the seed container 220, smaller seed particles may shift to the bottom of the respective isolated compartment 222 shown in FIGS. 14A and 14B, and larger particles may migrate to the top. Thus, when the force applying mechanism 230 shown in FIG. 18 applies a subsequent force to the seed and/or seed particles, the larger particles may be more easily broken down into smaller particles, and a more consistent and complete breakage can result.

Once the seed breaking operation is complete (for example, after a predetermined number of alternating applications of force and vibration), the platform 225 and seed container 220 can be moved to the seed collecting station 215, shown in FIG. 21. At the seed collecting station 215, the seed particles resulting from the breaking of the seed at the seed breaking station 210 can be transferred to a seed particle collector 250 for subsequent processing and/or analysis. The seed collecting station 215 includes a seed particle directing member 260 that is configured to provide an isolated passageway 262 between the isolated compartment 222 of the seed container 220 and a corresponding collection cavity 252 of the seed particle collector 250 (shown in FIG. 22). In the depicted embodiment, for example, the seed particle collector 250 is a standard lab plate having ninety-six collection cavities 252 (i.e., a 96-well standard lab plate). In this way, as described in greater detail below, once the seed particles are transferred to the seed particle collector 250, further analysis can take place within the cavities 252 of the seed particle collector, and no further transfer would be required. Thus, for example, although the original seed or seed portion may not have fit in a standard 96-well lab plate prior to the breaking operation, after the seed has passed through the seed breaking station 210, the resulting seed particles can be efficiently transferred to a standard lab plate (i.e., the seed particle collector 250) for analysis while at the same time substantially eliminating cross-contamination throughout the preparation process.

In some cases, the seed container 220, the seed particle directing member 260, and the seed particle collector 250 are part of an assembly 270. As shown in FIGS. 21 and 23, a first end 261 of the seed particle directing member 260 may be configured to secure to the seed container 220 (shown in FIG. 21) and a second end 263 of the seed particle directing member may be configured to secure to the seed particle collector 250. Fasteners, clips, or clamps 272, such as DE-STA-CO® clamps, may be used to hold the seed container 220, seed particle directing member 260, and seed particle collector 250 together. For example, the seed container 220 may be raised off the platform 225 once at the seed collecting station 215 and moved towards the first end 261 of the seed particle directing member 260. In that position, an operator may be prompted to move the clamps 272 at the first end of the seed particle directing member 260 from the unsecured position to the secured position, thereby securing the seed container 220 to the seed particle directing member 260.

When the seed container 220, seed particle directing member 260, and seed particle collector 250 have been secured together as an assembly 270, the seed particle directing member may be configured to rotate with the secured seed container and the seed particle collector, as shown in FIG. 24, to encourage the transfer of the seed particles from the seed container through the seed particle directing member and into the seed particle collector. In some cases, as depicted in FIG. 24, the assembly 270 is configured to rotate 180° about an axis A, such that the seed container 220 is topmost in the assembly and the seed particle collector 250 is bottommost. In this way, the force of gravity can act on the seed particles in the seed container 220 to pull the particles down through the isolated passageways of the seed particle directing member 260 and into the seed particle collector 250.

To further influence transfer of the seed particles from the seed container 220 through the seed particle directing member 260 and into the seed particle collector 250, in some embodiments the seed collecting station 215 also includes a vibratory mechanism 280 (shown in FIG. 21) that is configured to apply a vibratory action to the seed particle directing member. The vibratory mechanism 280 may be, for example, a pneumatic actuator that vibrates one or more of the seed particle collector 250, the seed particle directing member 260, and/or the seed container 220 to encourage the transfer of seed particles. The vibratory action may be continuous, or it may be intermittent. Furthermore, in some cases the vibratory action may be applied during the rotation of the assembly 270 from the start position (shown in FIG. 21) to the end position (shown in FIG. 24) (e.g., as the assembly is rotated 180°), after the assembly 270 has been rotated, or both before and after rotation.

To substantially prevent cross-contamination between passageways 262 during collection of the seed particles, seals 271 may be provided at the first end 261 of the seed particle directing member 260 (best seen in FIG. 41). For example, round square O-rings may be used to provide a seal between the seed container 220 and the seed particle directing member 260. In this way, seed particles from a particular isolated compartment 222 will only pass into the corresponding passageway 262, and not passageways that are aligned with other compartments.

Turning to FIG. 25, in some cases the seed particle directing member 260 may include a first directing member 264 and a second directing member 266. The first end 261 of the first directing member 264 may be configured to secure to the seed container 220 (not shown in FIG. 25), and a second end 265 of the first directing member may be configured to secure to a first end 267 of the second directing member 266, for example using an intermediate plate 268 or other component to which both directing members may be fastened. The intermediate plate 268 may also provide sealing surfaces between the first directing member 264 and the second directing member 266. For example, the intermediate plate 268 may be made of rubber, cork, or a similar sealing material that acts as a gasket when the seed particle directing member 260 is assembled (e.g., through the clamping action of the first directing member 264 and the second directing member 266 pushing against the intermediate plate). In this way, seed particles passing through a particular passageway 262 of the first directing member 264 can continue through only the corresponding passageway of the second directing member 266, and cross-contamination between passageways can be substantially prevented.

The second end 263 of the second directing member 266 may in turn be configured to secure to the seed particle collector 250. Again, a sealing surface may be provided at the second end 263 of the second directing member 266 to ensure a proper fit between the second directing member and the seed particle collector 250 and to substantially prevent seed particles from one passageway 262 of the second directing member from entering a collection cavity 252 of the seed particle collector other than the corresponding collection cavity.

In some cases, the seed particle collector 250 is configured as shown in FIG. 26, in which the "underside" (i.e., the end of the seed particle collector disposed farthest from the seed particle directing member 260) is defined by the exterior of each individual collection cavity 252. In this regard, the seed particle collector 250 may be configured to engage a collector tray 255 (shown in FIGS. 27A and 27B), for example, to facilitate handling of the seed particle collector. For example, the seed particle collector 250 may include one or more flanges 257 that are configured to be fastened to the collector tray 255 to hold the seed particle collector to the collector tray, as shown in FIGS. 26 and 27A.

The first and second directing members 264, 266 may be configured to be detached from each other, such that the second directing member and the seed particle collector 250 can be removed as a unit (see FIG. 28) from the seed collecting station 215 when the seed collecting operation is complete. For this reason, the second directing member 266 may include handles 269 for removing a filled seed particle collector 250 (which is secured to the second directing member 266) from the seed collecting station 215, as well as for inserting a new (i.e., unfilled) seed particle collector and second directing member 266 into the assembly 270 (see FIG. 21).

After the seed particle collector 250 is removed from the seed collecting station 215 (for example, in connection with detaching and removing the second directing member 266), the seed particle collector and second directing member may be taken (e.g., by an operator) to a second directing member cleaning station 300, shown in FIG. 29. The cleaning station 300 may include a passageway cleaning mechanism 310 configured to dislodge any seed particles that may remain in the isolated passageways 262 of the second directing member 266 and transfer them to the corresponding collection cavity 252 of the seed particle collector 250 (see FIGS. 22, 27A, and 27B). In this regard, the cleaning station 300 may have various configurations.

With reference to FIGS. 29, 30A, and 30B, for example, the cleaning station 300 may include rods 320, each rod being configured to fit into a corresponding isolated passageway 262 of the second directing member 266 to push seed particles into the corresponding collection cavity 252. Once the seed particle collector 250 and second directing member 266 are in place in the cleaning station 300, a pneumatic or other type of actuator 325 may be used to lower an array of rods 320 into the passageways 262.

For example, the array of rods may be configured to substantially match the configuration of the openings of the passageways 262 (e.g., to correspond with the number, spacing, and dimensions of the passageways). The rods 320 may be made of a flexible material that can be guided along the passageways 262 of the second directing member 266, such as Delrin® plastic material. In addition, as shown in FIG. 30B, the ends 322 of the rods 320 may be domed or otherwise configured to urge seed particle debris towards the corresponding collection cavities 252. Thus, through the action of the rods 320 being lowered into corresponding passageways 262, the passageways can be cleared of seed particle debris in preparation for use in subsequent seed breaking and collecting operations, and the seed particle debris can be added to the seed particles in the collection cavities 252 to be used for analysis, reducing waste.

To detach the seed particle collector 250 from the second directing member 266, for example after the second directing member has been cleared of seed particle debris at the cleaning station 300, the seed particle collector and second directing member may be moved (e.g., by an operator) to a seed particle collector removal station 350. The removal station 350 (shown in FIG. 31 without the seed particle collector 250 and second directing member 266 installed) may be configured to receive the seed particle collector and second directing member to facilitate the detachment of the seed particle collector from the second directing member, as shown in FIG. 32.

In this regard, the removal station 350 may be equipped with clamps 360 configured to hold the seed particle collector 250 in place, for example by pushing the seed particle collector against one or more fixed ends 362. The clamps 360 may be moved into position by an operator, for example, through the use of handles 365.

Once the seed particle collector 250 is in place, the operator may then unsecure clamps 270 that hold the seed particle collector to the second directing member 266. In this way, the second directing member 266 may be removed from the seed particle collector 250, and the seed particle collector may be unclamped from the removal station 350 and transported to another location for further processing and/or analysis of the seed particles container therein.

In order to prepare for subsequent seed breaking and collecting operations, one or more of the components of the system 200 may be cleaned to avoid having seed particles from one operation contaminate subsequent operations involving other seeds. For example, after the seed particles have been crushed and transferred from the seed container 220 to the seed particle collector 250 at the seed collecting station 215 or the seed container has otherwise been emptied of the seed particles, the used seed container may be cleaned for subsequent use. In this regard, the used seed container 220 may be taken to a container cleaning station 400, shown in FIG. 33. The container cleaning station 400 may be configured to receive the seed container 220 within an enclosure 410 having an access panel 420, such that once the seed container is placed inside, the operator may be protected from the operation of the cleaning station 400.

Referring to FIG. 34, in which the enclosure 410, access panel 420, and various other components are removed for ease of explanation, the seed container 220 may be held in place within the enclosure 410 using one or more clamps 430. In the depicted embodiment, the seed container 220 is placed such that the open ends of each isolated compartment 222 (not visible) are facing downward. As shown in FIGS. 35-37, once in position, an array 440 of air nozzles 442 corresponding to the number of isolated compartments 222 in a row of the seed container 220 may be passed along the seed container, such that compressed air is blown into each isolated compartment in one row substantially simultaneously, and then the array of air nozzles is moved to the next row to blow air into the corresponding isolated compartments. In this way, a reduced number of air nozzles 442 may be used to clean a larger number of isolated compartments 222. In some embodiments, however, the number of air nozzles 442 need not correspond to the number of compartments 222 (for example, fewer air nozzles may be provided), and the array 440 may be movable along each row to clean all of the compartments.

Regardless, the array 440 may be configured to ride along a track 450 (shown in FIG. 37), such that an operator may move the array back and forth past the various rows of isolated compartments 222 by moving handle arm 455. Seed particle debris that is cleared from the isolated compartments 222 may then fall (or be vacuumed) into a receptacle 460 for proper disposal (shown in FIG. 35).

Just as the seed container 220 can be cleaned between seed breaking and collecting operations, the force applying member 232 (shown, for example, in FIGS. 18 and 19) can also be cleaned to allow for re-use of the seed container without causing cross-contamination between seed batches. Turning to FIGS. 38 and 39, in some embodiments, for example, the system 200 includes a protrusion cleaning station 500 that has at least one cleaning member. In the depicted embodiment, the protrusion cleaning station 500 includes three cleaning members: a first brush 510, a second brush 520, and an air knife 530.

The protrusion cleaning station 500 may be configured to move into alignment with the protrusions 236 of the force applying member 232 to remove seed particles from the protrusions following contact between the protrusions and the seeds or seed particles. For example, the cleaning members 510, 520, 530 may be disposed on an extension 540 of the platform 225 or may otherwise be connected to the platform, such that the transport mechanism 700 (shown in FIG. 13) that is configured to automatically moved the seed container 220 (via the platform) from station to station is also configured to move the cleaning station 500 into alignment with the protrusions 236. In other embodiments, however, the force applying member 232 may be moved into alignment with the cleaning station 500, or the cleaning station may be located remotely from the platform 225 and/or transport mechanism 700 and may be moved into alignment with the protrusions 236 of the force applying member independently of the system 200 (for example, manually by an operator). The cleaning station 500 may, in some cases, also include a shield 560 that separates the cleaning members 510, 520, 530 from the platform 225. The shield 560 may be configured to close off the seed breaking station when the force applying member is in operation for safety reasons.

Referring to FIG. 39, the first and second brushes 510, 520 may be configured substantially similarly to each other, or they may have different dimensions and be made of different materials, as shown, so as to reach and clean seed particles at different locations on the protrusions 236. For example, one of the first and second brushes 510, 520 may be made of bronze or some other stiff material to remove seed particles that may be stuck to the protrusions 236 and require more force to remove, whereas the other of the brushes may be made of a more flexible material, such as nylon, to enable the brush to flex and reach around the protrusions and remove particles that may be in more difficult-to-reach locations. Similarly, one of the brushes 510 may be longer than the other 520 so that the brushes, in cooperation, may reach seed particles at different locations on the protrusions 236.

The air knife 530 may be connected to a compressed air supply and may be configured to generate a sheet of air 550 for "scraping" seed particles from the protrusions 236. In some cases, as shown in FIG. 39, the air knife 530, may be disposed at an angle, such that the sheet of air 550 hits the protrusions 236 at the same angle. The angle may, in some cases, be adjustable to allow an operator to configure the cleaning station 500 for optimal cleaning of the protrusions 236.

FIG. 40 shows the cleaning station 500 as it approaches alignment with the protrusions 236 (i.e., moving in the direction shown by the arrow). As the cleaning station 500 continues moving in the direction of the arrow, the sheet of air 550 generated by the air knife 530 will engage the leftmost row of protrusions 236 (with respect to the view shown in the figure) first. As the air knife 530 passes from the leftmost row of protrusions 236 to the next row, the second brush 520 will engage the leftmost row, followed by the first brush 510. In this way, the cleaning members 510, 520, 530 can sequentially engage each row of protrusions 236 as the cleaning station 500 moves from one end of the force applying member 232 to the other. In some embodiments, the cleaning station 500 may be configured to make multiple trips along the force applying member 232. For example, the cleaning station 500 may be configured to pass back and forth along the protrusions 236 three times before returning to the idle position shown in FIG. 38.

Turning now to FIG. 41, in some embodiments, the seed collecting station 215 may include a directing member cleaning mechanism 600 that is configured to substantially clear each isolated passageway 262 (for example, the isolated passageways of the first directing member 264) of seed particle debris. The directing member cleaning mechanism 600 may, for example, include an array 610 of air nozzles 620 that are each configured to provide a stream of compressed air into each corresponding portion of the passageway 262 of the first directing member 264. For example, if the first directing member 264 includes eight passageways 262 in each corresponding row, the array 610 may include eight air nozzles 620 that are spaced so as to be substantially aligned with the passageways, although fewer air nozzles may be provided, as described below.

Thus, as shown, once the second directing member 266 and seed particle collector 250 (shown in FIG. 24) are removed from the assembly 270 for further processing and the seed container 220 is detached from the first end 261 of the first directing member 264 (see FIG. 25), but before the first directing member is rotated back to the start position shown in FIG. 21, the directing member cleaning mechanism 600 may be activated to clean the first directing member. In this regard, the array 610 of air nozzles 620 may be moved (for example, via a track 630 along the first end 261 of the first directing member 264) from one row of passageways 262 to the next so that compressed air can be focused into each passageway in turn. If the number of air nozzles 620 provided on the array 610 is smaller than the number of passageways 262 in a row (for example, if only four air nozzles are provided), the array may also be configured to move in a direction perpendicular to the length of the track 630, so as to clear all eight passageways with the four nozzles (for example) before moving along the track to the next row of passageways.

The directing member cleaning mechanism 600 may be configured to pass along the rows of passageways 262 any number of times, according to the operator's preferences. For example, depending on the type of seed being processed through the system and the resulting tenacity of the seed particle debris, the cleaning mechanism 600 may be configured to provide the streams of compressed air into each passageway 262 twice, three times, or more. In this way, the directing member 260 may transfer subsequent batches of seed particles from the seed container to the seed particle collector without significant risk of cross-contamination from previous batches.

Alternatively or in addition to the array 610 of air nozzles 620, a vacuum mechanism (not shown) may be provided to pull the seed particle debris from the passageways 262 of the directing member 260 (e.g., the passageways of the first directing member 264). The vacuum mechanism may further be configured to act on other components or stations of the system 200 to clear such components of debris. For example, the vacuum mechanism may be in communication with the seed breaking station 210 to clear the area of debris resulting from seed breaking operations.

In accordance with various embodiments of the present invention, the number of seed particles and the size of the seed particles upon breaking the seeds may vary depending on the requirements of the application. For example, in some embodiments each seed may be broken into two seed particles, however in other embodiments each seed may be broken into a plurality of seed particles. Factors that may influence the number and/or size of the seed particles may include, but need not be limited to, the degree and manner of force applied by the force applying member, the shape of the force applying member and/or the shape of the protrusions of the force applying member, and/or the characteristics (such as the type of material and strength and deformation characteristics thereof) of the seed container and/or a lower plate, including the characteristics of the first layer of the seed container and/or the characteristics of a backing portion of the seed container. Other factors that may influence the number and/or size of seed particles may include the physical properties of the seed and/or the characteristics of and/or the number of strokes applied to a seed by the force applying member. In addition, various factors may influence the consistency of the size of the seed particles and the degree of the force necessary to generate consistent seed particles. For example, in some embodiments it has been determined that pre-drying the seeds prior to subjecting the seeds to a force may produce seed particles having more consistent sizes and may reduce the force necessary to generate the consistent seed sizes. It should be noted that in various embodiments, the temperature and duration of pre-drying may be influenced by type, size, and/or oil content of the seed.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of preparing a representative seed sample for analysis, the method comprising:
   receiving a seed container having a plurality of isolated compartments, the seed container being operatively coupled to a seed particle collector, the seed particle collector having a plurality of collection cavities, each respective isolated compartment of the seed container being positioned in communication with a corresponding collection cavity of the seed particle collector, at least one isolated compartment of the plurality of isolated compartments having a seed therein;
   applying a force to the seed in the at least one isolated compartment by pressing a force applying member into the seed to break the seed into two or more seed particles; and
   directing the seed particles of the at least one isolated compartment into at least one corresponding collection cavity of the seed particle collector.

2. The method of claim 1, wherein the force applying member comprises a plurality of protrusions, and wherein applying a force to the seed comprises pressing at least one protrusion of the plurality of protrusions into direct contact with the seed in the at least one isolated compartment to break the seed into the seed particles.

3. The method of claim 1, wherein applying a force to the seed comprises applying force to the seed and then intermittently applying force to the resulting seed particles to encourage further breakage of the seed.

4. The method of claim 3, further comprising intermittently applying a vibratory action to the seed container to encourage breakage of the seed into the seed particles.

5. The method of claim 1, wherein the at least one isolated compartment having a seed therein comprises a plurality of selected isolated compartments having a seed therein, and wherein the step of directing the seed particles of the at least one isolated compartment into the at least one corresponding collection cavity of the seed particle collector comprises directing the seed particles of the plurality of selected isolated compartments into a plurality of corresponding collection cavities of the seed particle collector.

6. The method of claim 1, wherein the seed particles are directed into the at least one corresponding collection cavity of the seed particle collector using a seed particle directing member, wherein the seed particle directing member comprises a plurality of channels, each channel of the plurality of channels being configured to provide an isolated passageway between a respective isolated compartment of the seed container and a corresponding collection cavity of the seed particle collector.

7. The method of claim 6, further comprising rotating the seed particle directing member together with the seed container and the seed particle collector to encourage transfer of the seed particles from the seed container through the seed particle directing member and into the seed particle collector.

8. The method of claim 7, further comprising applying a vibratory action to the seed particle directing member to influence transfer of the seed particles from the seed container through the seed particle directing member and into the seed particle collector.

9. The method of claim 6, further comprising removing the seed particle collector from the seed particle directing member and substantially clearing the at least one isolated passageway of seed particle debris.

10. A method of preparing a representative seed sample for analysis, the method comprising:
receiving a seed container having at least one isolated compartment, the isolated compartment having a seed therein;
applying a force to the seed in the isolated compartment by pressing a force applying member into the seed to break the seed into two or more seed particles; and
directing the seed particles of the isolated compartment into a corresponding collection cavity of a seed particle collector,
wherein the seed particles are directed into the corresponding collection cavity of the seed particle collector using a seed particle directing member that comprises at least one channel configured to provide an isolated passageway between the isolated compartment of the seed container and the corresponding collection cavity of the seed particle collector.

11. The method of claim 10, wherein the force applying member comprises at least one protrusion, and wherein applying a force to the seed comprises pressing the protrusion into direct contact with the seed in the isolated compartment to break the seed into the seed particles.

12. The method of claim 10, wherein applying a force to the seed comprises applying force to the seed and then intermittently applying force to the resulting seed particles to encourage further breakage of the seed.

13. The method of claim 12, further comprising intermittently applying a vibratory action to the seed container to encourage breakage of the seed into the seed particles.

14. The method of claim 10, further comprising rotating the seed particle directing member together with the seed container and the seed particle collector to encourage transfer of the seed particles from the seed container through the seed particle directing member and into the seed particle collector.

15. The method of claim 14, further comprising applying a vibratory action to the seed particle directing member to influence transfer of the seed particles from the seed container through the seed particle directing member and into the seed particle collector.

16. The method of claim 10, further comprising removing the seed particle collector from the seed particle directing member and substantially clearing the isolated passageway of seed particle debris.

* * * * *